US012624397B2

(12) United States Patent
Baum et al.

(10) Patent No.:  US 12,624,397 B2
(45) Date of Patent:     May 12, 2026

(54) BIOMARKERS ASSOCIATED WITH ANTI-IL-36R ANTIBODY TREATMENT IN GENERALIZED PUSTULAR PSORIASIS

(71) Applicant: Boehringer Ingelheim International GmbH, Ingelheim am Rhein (DE)

(72) Inventors: Patrick Baum, Warthausen (DE); Ahmed Karim Farag, Biberach (DE); Sudha Visvanathan, Hartsdale, NY (US)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 1057 days.

(21) Appl. No.: 17/691,486

(22) Filed: Mar. 10, 2022

(65) Prior Publication Data

US 2022/0290239 A1     Sep. 15, 2022

Related U.S. Application Data

(60) Provisional application No. 63/255,148, filed on Oct. 13, 2021, provisional application No. 63/160,135, filed on Mar. 12, 2021.

(51) Int. Cl.
*C12Q 1/6883*     (2018.01)
*C07K 16/28*     (2006.01)
*G01N 33/564*     (2006.01)
*C12Q 1/6869*     (2018.01)

(52) U.S. Cl.
CPC ........ *C12Q 1/6883* (2013.01); *C07K 16/2866* (2013.01); *G01N 33/564* (2013.01); *C07K 2317/24* (2013.01); *C12Q 1/6869* (2013.01); *C12Q 2600/158* (2013.01); *G01N 2800/205* (2013.01); *G01N 2800/52* (2013.01)

(58) Field of Classification Search
CPC ............... A61P 17/06; C07K 16/2866; C07K 2317/24; C12Q 1/6869; C12Q 1/6883; C12Q 2600/106; C12Q 2600/136; C12Q 2600/158; G01N 2800/205; G01N 2800/52; G01N 33/564; G01N 33/6893
See application file for complete search history.

(56) References Cited

U.S. PATENT DOCUMENTS

| | | | |
|---|---|---|---|
| 5,595,756 | A | 1/1997 | Bally et al. |
| 6,416,973 | B1 | 7/2002 | Bakker et al. |
| 6,953,843 | B2 | 10/2005 | Bakker et al. |
| 7,332,574 | B2 | 2/2008 | Bakker et al. |
| 8,034,771 | B2 | 10/2011 | Sims et al. |

(Continued)

FOREIGN PATENT DOCUMENTS

| | | |
|---|---|---|
| CN | 107362351 A | 11/2017 |
| EP | 1003861 A2 | 5/2000 |

(Continued)

OTHER PUBLICATIONS

Clinical Trials "History of Changes for Study: NCT03135548, Initial Dosing of BI 655130 in Palmoplantar Pustulosis Patients" (2020) clinicaltrials.gov, 5 pgs.

(Continued)

*Primary Examiner* — Jennifer Wecker
(74) *Attorney, Agent, or Firm* — Wendy M. Gombert

(57)     ABSTRACT

This invention generally relates to biomarkers associated with anti-IL-36R antibody treatment in generalized pustular psoriasis (GPP). The invention also relates to methods of using the biomarkers disclosed.

2 Claims, 10 Drawing Sheets

Specification includes a Sequence Listing.

(56) References Cited

U.S. PATENT DOCUMENTS

| | | | |
|---|---|---|---|
| 8,481,021 | B2 | 7/2013 | Sims et al. |
| 9,023,995 | B2 | 5/2015 | Brown et al. |
| 9,334,320 | B2 | 5/2016 | Okun et al. |
| 10,414,821 | B2 | 9/2019 | Liu |
| 10,526,410 | B2 | 1/2020 | Bowers |
| 11,730,812 | B2 | 8/2023 | Denkinger |
| 2004/0110930 | A1 | 6/2004 | Reinl et al. |
| 2004/0132085 | A1 | 7/2004 | Bakker et al. |
| 2004/0177391 | A1 | 9/2004 | Bakker et al. |
| 2005/0084900 | A1 | 4/2005 | Bakker et al. |
| 2007/0041905 | A1 | 2/2007 | Hoffman et al. |
| 2007/0071675 | A1 | 3/2007 | Wu et al. |
| 2008/0171035 | A1 | 7/2008 | Bakker et al. |
| 2008/0292623 | A1 | 11/2008 | Bakker et al. |
| 2009/0263403 | A1 | 10/2009 | Bakker et al. |
| 2010/0129374 | A1 | 5/2010 | Bakker et al. |
| 2010/0150945 | A1 | 6/2010 | Bigler et al. |
| 2010/0221252 | A1 | 9/2010 | Bigler et al. |
| 2011/0110852 | A1 | 5/2011 | Miller et al. |
| 2011/0159011 | A1 | 6/2011 | Carrier et al. |
| 2012/0121580 | A1 | 5/2012 | Bhambhani et al. |
| 2012/0177647 | A1 | 7/2012 | Bigler et al. |
| 2012/0244158 | A1 | 9/2012 | Brige et al. |
| 2013/0186797 | A1 | 7/2013 | Walsh et al. |
| 2013/0236471 | A1 | 9/2013 | Brown et al. |
| 2017/0355756 | A1 | 12/2017 | Julien et al. |
| 2018/0094065 | A1 | 4/2018 | Bowers |
| 2018/0273627 | A1 | 9/2018 | Boecher et al. |
| 2019/0028285 | A1 | 1/2019 | Cheng |
| 2019/0284273 | A1 | 9/2019 | Boecher et al. |
| 2019/0284285 | A1 | 9/2019 | Thoma et al. |
| 2020/0015462 | A1 | 1/2020 | Murphy |
| 2020/0017592 | A1 | 1/2020 | Fairhurst et al. |
| 2020/0207862 | A1 | 7/2020 | Baum et al. |
| 2020/0282053 | A1 | 9/2020 | Denkinger et al. |
| 2020/0402998 | A1 | 12/2020 | Cho |
| 2022/0073628 | A1 | 3/2022 | Fine et al. |
| 2022/0119538 | A1 | 4/2022 | Thoma et al. |
| 2022/0256258 | A1 | 8/2022 | Fitzgerald et al. |
| 2022/0281987 | A1 | 9/2022 | Hall et al. |
| 2022/0290239 | A1 | 9/2022 | Baum et al. |
| 2022/0402998 | A1 | 12/2022 | Liu et al. |

FOREIGN PATENT DOCUMENTS

| | | |
|---|---|---|
| EP | 1627927 A2 | 2/2006 |
| EP | 2152750 A1 | 2/2010 |
| EP | 2176294 A1 | 4/2010 |
| EP | 2337799 A2 | 6/2011 |
| JP | 2009521933 A | 6/2009 |
| JP | 2016531123 A | 10/2016 |
| JP | 2017114829 A | 6/2017 |
| JP | 2018512157 A | 5/2018 |
| JP | 2020512344 A | 4/2020 |
| KR | 20180098625 A | 9/2018 |
| NO | 9906557 A2 | 2/1999 |
| NO | 2010025369 A2 | 3/2010 |
| WO | 9856418 A1 | 12/1998 |
| WO | 9906577 A2 | 2/1999 |
| WO | 2004091658 A1 | 10/2004 |
| WO | 2008033333 A2 | 3/2008 |
| WO | 2008133857 A1 | 11/2008 |
| WO | 2009006112 A1 | 1/2009 |
| WO | 2013074569 A1 | 5/2013 |
| WO | 201616842 A1 | 2/2016 |
| WO | 16168542 A1 | 10/2016 |
| WO | 2016168542 A1 | 10/2016 |
| WO | 2017117311 A1 | 7/2017 |
| WO | 2018183173 A1 | 10/2018 |
| WO | 2019177883 A2 | 9/2019 |
| WO | 2019177888 A1 | 9/2019 |
| WO | 2020136101 A1 | 7/2020 |
| WO | 2020185479 A1 | 9/2020 |

OTHER PUBLICATIONS

Clinical Trials "History of Changes for Study: NCT03782792, A Study to Test BI 655130 in Patients iwth Flare-up of a Skin Disease called Generalized Pustular Psorasis" (2018) clinicaltrials.gov, 6 pgs.

International Search Report PCT/EP2019/086521 mailed Apr. 6, 2020.

Su, Zhi et al. "IL-36 receptor antagonistic antibodies inhibit inflammatory responses in preclinical models of psoriasiform dermatitis" (2019) Experimental Dermatology, 28, 113-120.

Clinical Trials "BI655130 Single Dose in Generalized Pustular Psoriasis" (2018) Identifier: NCT02978690, 6 pgs.

Clinical Trials "This Study Tests How BI 655130 Works in Patients with Active Ulcerative Colitis. The Study also Tests how well BI 655130 is Tolerated and Whether it Helps the Patients" (2020) NCT03100864, 28 pgs.

Russell, SE et al. "IL-36a expression is elevated in ulcerative colitis and promotes colonic inflammation" (2016) Mucosal Immunology, vol. 9, No. 5, 1193-1204.

Ding, Liping et al. "IL-36 cytokines in autoimmunity and inflammatory disease" (2018) Oncotarget, vol. 9, No. 2, 2895-2901.

Nishida, Atsushi et al. "Increased Expression of Interleukin-36, a Member of the Interleukin-1 Cytokine Family, in Inflammatory Bowel Disease" (2016) Inflamm Bowel Dis, vol. 22, No. 2, 303-314.

Andoh, Akira et al. "Increased Expression of Interleukin-36 in the Inflamed Mucosa of Inflammatory Bowel Disease" Abstract 1812, (2015) The American Journal of Gastroenterology, vol. 110, Supplement 1, S770.

Johnston, Andrew et al. "IL-1 and IL-36 are dominant cytokines in generalized pustular psoriasis" (2017) J Allergy Clin Immunol, 109-120.

Tsai, Ya-Chu et al. "Anti-interleukin and interleukin therapies for psoriasis: current evidence and clinical usefulness" (2017) Therapeutic Advances in Musculoskeletal Disease, vol. 9 (11), 277-294.

Body Mass Index Table from www.nhlbi.nih.gov/health/educational/lose_wt/BMI/bmi_tbl.pdf <http://www.nhlbi.nih.gov/health/educational/lose_wt/BMI/bmi_tbl.pdf>, viewed Sep. 16, 2021.

Wong, Chi Heem et al. "Estimation of clinical trial success rates and related parameters" (2019) Biostatistics, 20, 2, 273-286.

Clinical Trials "A Study in Patients with Atopic Eczema to Test How Effective BI 655130 Is and How Well It Is Tolerated" (2021) Last Update Posted, NCT03822832, 11 pgs.

Nolan, S. et al. "505 Therapeutic activity of an anti-IL36R blocking antibody in inhibiting atopic dermatitis-like skin Inflammation in mice" (2019) Journal of Investigative Dermatology, Society for Investigative Dermatology (SID) 2019, Meeting Abstract Supplement, 2 pgs.

Patrick, Garrett et al. "Epicutaneous Staphylococcus aureaus induces IL-36 to enhance IgE production and ensuing allergic disease" (2021) The Journal of Clinical Investigation, 1-15.

Puar, Neha et al. "New treatments in atopic dermatitis" (2020) Annals Allergy Asthma Immunology, 126, 21-21.

International Search Report PCT/US2021/032713 mailed Aug. 30, 2021, 12 pgs.

International Search Report PCT/US2020/021059 mailed on Jun. 23, 2020.

Anonymous Anti-IL36 gamma/IL—1 F9 antibody (OT12F4) (ab156783), Jan. 1, 2019, XP055650144, 6 pgs.

Wang, Wei et al. "Antibody Structure, Instability and Formulation" (2007) Journal of Pharmaceutical Sciences, vol. 96, No. 1, 1-26.

Boehringer Ingelheim "Boehringer Ingelheim R&D pushes to Transcend Disease Boundaries" (2018) Business Wire, 4 ogs.

Lacy, et al. "Correlation between Antibody Affinity and Activity: Understanding the Molecular Basis for a Picomolar to Femtomolar Increase in Affinity" (2009) Abstract, 1621-Pos, Board B465, vol. 96, Issue 3, S1, 317a-318a.

Chang, Byeong S. et al. "Practical Approaches to Protein Formulation Development" (2022) Kluwer Academic/ Plemum publishers, 1-25.

(56)                References Cited

OTHER PUBLICATIONS

Bachelez, Herve et al. "Inhibition of the Interleukin-36 Pathway for the Treatment of Generalized Pustular Psoriasis" (2019) The New England Journal of Medicine, 380: 10, 981-983.

Satoh T K et al: "Are neutrophilic dermatoses autoinflammatory disorders?" (2018) The British Journal of Dermatology, vol. 178, No. 3, pp. 603-613.

Marzano Angelo V. et al: "Mechanisms of Inflammation in Neutrophil-Mediated Skin Diseases", (2019) Frontiers in Immunology, vol. 18, 2019, p. 1859.

Mrowietz Ulrich et al: "Spesolimab, an Anti-Interleukin-36 Receptor Antibody, in Patients with Palmoplantar Pustulosis: Results of a Phase IIa, Multicenter, Double-Blind, Randomized, Placebo-Controlled Pilot Study", (2021) Dermatology and Therapy, vol. 11, No. 2, 571-585.

International Search Report PCT/US2021/041734 mailed Nov. 11, 2021, 4 pgs.

Clinical Trials, Interleukin-1 receptor-like 2 isoform a precursor, downloaded from https://ncbi.nlm.nlh.gov/protein/NP_003845.2?report+girevhist on Sep. 21, 2022 2022.

Elias, IL-36 in chronic inflammation and fibrosis, JCI, vol. 131, 2021, 14 pages.

Melton, Interleukin-36 Cytokine/Receptor Signaling, Int. J. of Molecular Sci., vol. 21, 2020, 22 pages.

Neufert, Rationale for IL-36 receptor antibodies in ulcertaive colitis, Expert opinion on Biological Therapy, vol. 20, 2020, 5 pages, https://doi.org/10.1080.14712598.2020.1695775.

Scheibe, Inhibiting Interleukin 36 receptor signaling reduces fibrosis in mice with chronic intestinal inflammation, Gastroenterology, vol. 156, 2019, 27 pages.

International Search Report and Written Opinion for PCT.US2022/074888 mailed Nov. 29, 2022.

Kang, Rapid Formulation Development for Monoclonal Antibodies, BioProcess Chem., vol. 14, 2016, 4 pages.

Li, Spinal II-36/II-36R participates in the maintenance of chronic inflammatory pain through adtroglial JNK pathway, GLIA, vol. 67, 2019, Retrieved from the internet: URL: https://api.wiley.com/onlinelibrary.tdm/v1articles/10/1002Fglia.23552.

Alvarez, Imiquimod Treatment causes systemic disease in mice resembling generalized pustular psoriasis in an IL-1 and IL-36 Dependent Manner, GLIA, vol. 1, 2016, Retrieved from the Internet, URL:http://downloads.hindawi.com/journals/mi2016/6756138/XML.

Ratnarajah, Spesolimab, a novel treatment for pustular psoriasis, Journal od cutaneous med and surgery, vol. 24, 2020, Retrieved from the internet, URL:http://jouranls.sagepub.com/doi/full-XML/10.1177/1203475419888862.

Ly, Diagnosis and screening of patients with generalized pustular psoriasis, Psoriasis, Targets and Therapy, vol. 9, 2019, p. 37-42.

Vajdos, Comprehensive Functional Maps of the Antigen binding site of an Anti-ErbB2 Antibody obtained with shotgun Scanning Mutagenesis, J. Mol. Biol., vol. 320, 2002, p. 415-428.

Brown, Tolerance to single, but not multiple, amino acid replacements in antibody Vh CDR2, J. Immunol., vol. 320, 1996, p. 3285-3291.

Waiker, Imperfect Gold Standards for Kidney Injury Biomarker Evaluation, J. Am. Soc. Nephrol. Vol. 23, 2012, p. 13-21.

Ganesan, Generation and functional characterization of anti-human and anti-mouse IL-36R antagonist monoclonal antibodies, MABS, vol. 9, 2017, p. 143-154.

Kazumitsu, The majority of generalized pustular psoriasis without psoriasis vulgaris is caused by deficiency of interleukin-36 receptor antagonist, vol. 133, 2013, p. 514-521.

A study to test how effective and safe different doses of BI 655130 are in patients with a moderate to severe form of the skin disease palmoplantar pustulosis. ClinicalTrials.gov identifier: NCT4015518. Jul. 9, 2019. Accessed May 19, 2023. https://clinicaltrials.gov/ct2/history/NCT04015518?V_5=V(Year2019).

Freitas, Screening and Treatment of Patients with palmoplantar Pustolosis (PPP): A review of current practices and recommendations. Clinical Cosmet. Invest. Dermatol., vol. 13, 2020, p. 561-578.

Walpole, The weight of nations, BMC Public Health, vol. 12, 2012, 6 pages.

Edwards, The remarkable flexibility of the human antibody repertoire, J, Mole. Biol., vol. 1, 2003, p. 103-118.

Kussie, A single engineered amino acid substitution changes antibody fine specificity, J. Immunol., vol. 1, 1994, p. 146-52.

Anonymous, A study in patients with atopic eczema to test how effective BI655130 is and how well it is tolerated, Retrieved from the internet, http:/clinicaltrials.gov.ct2/show/record/NCT3822832/ retrieved Aug. 16, 2021.

Clinical Trials, A study in patients with Mild or moderate Ulcerative colitis who take a TNF inhibitor, History of changes for study, NCT103123120, Oct. 15, 2021.

International Report on Patentability for PCT/US2022/019742 received Sep. 21, 2023.

Clinical Trials, A study in patients with atopic eczema to test how effective BI 655130 is and how well it is tolerated, 2019; NCT03822832, 87 pages.

Berke, Atopic Dermatitis, Americam Family Physician, vol. 86, 2012, p. 35-42.

Costanzo, Pustular psoriasis with a focus on generalized pustualr psoriasis, Italian J. of Dermatology and Venereology, vol. 157, 2022, p. 489-96.

Puig, Generalized pustular Psoriasis: a global delphi consensus on clinical course, diagnosis, treatment goals, JEADV, vol. 10, 2022, 16 pages.

Alavi, Speso for hidradentitis supparativia, J. Am. Acad Dermatol, vol. 89, 2023, 1 page.

Belato, Response to Interleukin-36 in hidradentitis suurativa, British J. of Dermatology, vol. 176, 2018, 1 page.

Gouin, Trangenic Kallikrein 14 mice display major hair shaft defects associated with desmoglein 3 and 4 degradation, abnormal epidermal differentiation, J. Invest Dermatol., vol. 140, 2020, p. 1184-1194.

Speso entryin IUPHAR/BPS Guide to Phamra, www.guideto[harmacology.org/GRAC/ligandDispalyforward?tab=clinical&ligandld=12169; accessed Jan. 26, 2024.

Hessam, Interleukin-26 in hidradentits suppurativa, Brit. J. Dermatol, vol. 178, 2018, p. 591-592.

Malik, Ichthyosis molecular fingerprinting shows profound TH17 skewing and a unique barrier genomic signature, J. Allergy Clin Immunol., vol. 143, 2019, p. 604-618.

Navarini, Neutrophilic dermatoses and autoinflammatory diseases with skin involvement, Smin Immunopathol, vol. 38, 2016, p. 45-56.

Polesie, Secukinumab in the treatment of generalized pustular psoriasis, acta derm veneral, vol. 97, 2017, p. 124-125.

Tsai, Anti-interleukin and interleukin therapies for psoriasis, Ther. Adv. Muscoloskel. Dis. Vol. 9, 2017, p. 277-294.

Kimball, Adalimumab for the treatment of moderate to severe hidradentitis Suppurativa, Annals of internal Medicine, vol. 157, 2012, 19 pages.

Wark, The microbiome in Hidradentitis Supparativa, A review, Dermatol., Thera., vol. 11, 2021, 14 pages.

Zouboulis, Hidradenitis Suppurativa, Dermatology, vol. 231, 2015, p. 184-190.

Revillet, Bacterial Pathogens Associated with Hidradenitis Suppurativa, Emerging Infectious Diseases, vol. 20, 2014, 9 pages.

Frew, The effect of subcutaneous brodalumab on clinical disease activity in hidraenitis suppurativa, J. Am. Acad Derma., vol. 5, 2020, 15 pages.

Glatt, Efficacy and Safety of Bimekizumab in Moderate to severe Hidradenitis Suppurativa, vol. 157, 2021, 10 pages.

Li, Construction strategies for developing expression vectors for recombinant monoclonal antibody production in CHO cells, Molecular Biology Reports, vol. 45, 2018, 6 pages.

Byrd, Neutrophil extracellular traps, B cells, and type 1 interferons contribute to immune dysregulation in hidradenitis suppurativa, Science Translational Med., vol. 508, 2021, 13 pages.

(56) References Cited

OTHER PUBLICATIONS

UCB announcement, UCB Annoucement Positive Phase 3 studies for Bimekizumab in Hidradenitis Suppurativa, last updated Dec. 2022.

Robins, Estimation of a common effect parameter from sparse follow-up data, Biometrics, vol. 51, 1985, 15 pages.

Crommelin, Formulation of Biologics including Biopharmaceutical Considerations, Utrect Institute, vol. 10, 2019, 21 pages.

Flood, Biologic Treatment for Hidradenitis Suppurativa, Am. J. of Clinical Derma., vol. 20, 2019, 14 pages.

Phan, Global prevalence of hidradenitis suppurativa and geograhical variation, Biomedical Derma., vol. 10, 2020, 6 pages.

Highet, Streptoccus milleri causing treatable infection in perineal hidradenitis suppurativa, British J. of Derma., vol. 103, 9 pages.

Zouboulis, Development and validation of the International Hidradenitis Suppurativa severity score system, British J. of Derma., vol. 177, 2017, 9 pages.

Revillet, The microbiological landscape of Anaerobic infections in Hidradenitis Suppurativa, Clinical Infectious Diseases, vol. 65, 2017, 10 pages.

Yellen, Measuring fatigue and other anemia related symptoms with the functional assessment of cancer therapy, J. of Pain and Symptom management, vol. 13, 1997, 12 pages.

Zouboulis, European S1 guideline for the treatment of hidradenitis suppurativa, JEADV, vol. 10, 26 pages.

Kimball, HiSCR a novel clinical endpoint to evaluate therapeutic outcomes in patients with hidradenitis suppurativa, JEADV, vol. 10, 2016, 6 pages.

International Search Report and Written Opinion for PCT/US2022/019743 mailed Oct. 21, 2022.

Baliwag, Cytokines in psoriasis, Cytokine, vol. 73, 2015, 9 pages.

Baum, Generalized Pustular psoriasis and palmoplantar pustulosis both slow upregulation of the IL-36, neutrophil chemokine, and innate pathways that are modulated by spesolimab, and anti-IL-36 receptor antibody treatment, Journal of Investigative Dermatology, Adaptive and Auto-Immunity, www.jidonline.org., vol. 140, 2020, p. S5.

Baum, Treatment with spesolimab, an anti-interleukin-36 receptor antibody, in patients with generalized pustular psoriasis, ESDR 2019 Annual Meeting, Retrieved from Internet: URL:https://www.sciencedirect.com/science/article/pii/S0022202X19322444/pdfft?md5=main.pdf on Jun. 23, 2022, 1 page.

Baum, Pustular psoriasis: molecular pathways and effects of spesolimab in generalized pustular psoriasis, Journal of Allergy and clinical immunology, vol. 149. 2021, p. 1402-1412.

Brenner, Gernalized pustular psoriasis induced by systemic glucocorticosteroids, Bristish Journal of Dermatology, vol. 161, 2009, p. 964-963.

Yuan, Biology of IL-36 Signaling and its role in systemic Inflammatory Diseases, Frontiers in Immunology, vol. 10, 2019, p. 2532.

Zeng, Integrated analysis of gene expression profiles identifies transciption factors potentially involved in psoriasis pathogenesis, J. of Cellular Biochem., vol. 120, 2019, p. 12582-12594.

Tortola, Psoriasiform dermatitis is driven by IL-36-mediated DC-keratinocyte crosstalk, The J. of Clinical Investigation, vol. 122, 2012, p. 3965-3976.

Foster, IL-36 promotes myeloid cell infiltration activation and inflammatory activity in skin, The j. of immunolgy, vol. 192, 2014, p. 6053-6061.

Swindell, 7th International Congress of psoriais: from gene to clinic: The Queen Elizabeth II Conference Centre, London, UK, Dec. 11-13, 2014, British Journal of Dermatology, vol. 171, 2014, 20 pages.

Arend, William P. et al. "IL-1, IL-18, and IL-33 families of cytokines" Immunological Reviews (2008) vol. 223, pp. 20-22.

Blumberg, Hal et al. "IL-1RL2 and Its Ligands Contribute to the Cytokine Network in Psoriasis" The Journal of Immunology (2010) vol. 185, pp. 4354-4362.

Blumberg, Hal et al. "Opposing activities of two novel members of the IL-1 ligand family regulate skin inflammation" The Journal of Experimental Medicine (2007) vol. 204, No. 11, pp. 2603-2614.

Born, Teresa et al. "Identification and characterization of two members of a novel class of the interleukin-1 receptor (IL-1R) family. Delineation of a new class of IL-1R-related proteins based on signaling" The Journal of Biological Chemistry (2000), vol. 275, pp. 29946-29954.

Bowie, James U. et al. "Deciphering the Message in Protein Sequences: Tolerance to Amino Acid Substitutions" Science (1990) vol. 247, pp. 1306-1310.

Burgess, Wilson H. et al. "Possible Dissociation of the Heparin-binding and Mitogenic Activities of Heparin-binding (Acidic Fibroblast) Growth Factor-1 from its Receptor-binding Activities by Site-directed Mutagenesis of a Single Lysine Residue" Journal of Cell Biology, (1990) vol. 111, pp. 2129-2138.

Chustz, Regina T. et al. "Regulation and Function of the IL-1 Family Cytokine IL-1F9 in Human Bronchial Epithelial Cells" Am J Respir Cell Mol Biol (2011) vol. 45, pp. 145-153.

Creative Diagnostics "Mouse anti-IL1RL2 Monoclonal Antibody" Product Information. Gene ID 8808. mRNA Ref Seq NM_003854. (2004).

Debets, Reno et al. "Two Novel IL-1 Family Members, IL-1d and IL-1e Function as an Antagonist and Agonist of NF-κb Activation Through the Orphan IL-1 Receptor-Related Protein 21" The Journal of Immunology (2001) vol. 167, pp. 1440-1446.

Dinarello, Charles A. "Immunological and Inflammatory Functions of the Interleukin-1 Family" The Annual Review of Immunology (2009) vol. 27, pp. 519-550.

Dinarello, Charles et al. "IL-1 family nomenclature" Nature Immunology (2010) vol. 11, pp. 973-974.

International Search Report for PCT/US2012/064933 filed Nov. 14, 2012, mailed Feb. 7, 2013.

Johnston, Andrew et al. "IL-1F5, -F6, -F8, and -F9: A Novel IL-1 Family Signaling System that is Active in Psoriasis and Promotes Keratinocyte Antimicrobial Peptide Expression" The Journal of Immunology (2011) vol. 186, pp. 2613-2622.

Azar, Eliane et al. "Transforming Growth Factor a: Mutation of Aspartic Acid 47 and Leucine 48 Results in Different Biological Activities" Molecular and Cellular Biology (1988) vol. 8, No. 3, pp. 1247-1252.

Lingel, Andreas et al. "Structure of IL-33 and its Interaction with the ST2 and IL-1RAcP Receptors—Insight into Heterotrimeric IL-1 Signaling Complexes" Structure (2009) vol. 17, pp. 1398-1410.

Lovenberg, Timothy W. et al. "Cloning of a cDNA encoding a novel interleukin-1 receptor related protein (IL1R-rp2)" Journal of Neuroimmunology, (1996) vol. 70, pp. 113-122.

Magne, David et al. "The new IL-1 Family Member IL-1F8 stimulates production of inflammatory mediators by synovial fibroblasts and articular chondrocytes" Arthritis Research & Therapy (2006) vol. 8:R80, 11 pgs.

Marrakchi, Slaheddine et al. "Interleukin-36-Receptor Antagonist Deficiency and Generalized Pustular Psoriasis" New England Journal of Medicine (2011) vol. 365 pp. 620-628.

McMahan, Catherine J. et al. "A Novel IL-1 receptor, cloned from B cells by mammalian expression, is expressed in many cell types" EMBO Journal (1991) vol. 10, No. 10, pp. 2821-2832.

NCBI Gene databases (IL1RL2 interleukin 1 receptor-like 2 [*Homo sapiens* (human)]; http:www.ncbi.nlm.nib.gov/gene/8808; downloaded May 18, 2014, 8 pgs.

Ramadas, Ravisankar A. et al. "IL-36a Exerts Pro-Inflammatory Effects in the Lungs of Mice" PLOS one (2012) vol. 7, Issue 9, e45784, 17 pgs.

Ramadas, Ravisankar A. et al. "Interleukin-1 Family Member 9 Stimulates Chemokine Production and Neutrophil Influx in Mouse Lungs" Am J Respir Cell Mol Biol (2011) vol. 44, pp. 134-145.

Tortola, Luigi et al. "Psoriasiform dermatitis is driven by IL-36-mediated DC-keratinocyte crosstalk" The Journal of Clinical Investigation (2012) vol. 122, No. 11, pp. 3965-3976.

Towne, Jennifer E. et al. "Interleukin (IL)-1F6, IL-1F8, and IL-1F9 Signal through IL-1Rrp2 and IL-1RAcP to Activate the Pathway Leading to NF-κB and MAPKs*" The Journal of Biological Chemistry (2004) vol. 279, No. 14, pp. 13677-13688.

(56) References Cited

OTHER PUBLICATIONS

Towne, Jennifer E. et al. "Interleukin-36 (IL-36) Ligands Require Processing for Full Agonist (IL-36a, IL-36b, and IL-36g) or Antagonist (IL-36Ra) Activity" The Journal of Biological Chemistry (2011) vol. 286, No. 49, pp. 42594-42602.
Matsuba et al., "Preparation of Super-High Affinity Rabbit Monoclonal Antibodies Against Estradiol.: Application to Highly Sensitive Estradiol Measurement", TOSOH Research & Technol. Review. 2008, vol. 52, pp. 3-9.
Steidl et al., "In vitro affinity maturation of human GM-CSF antibodies by targeted CDR-diversification", Mol. Immunol, 2008, vol. 46, pp. 135-144.
Vajdos et al., "Comprehensive Functional Maps of the Antigenbinding Site of an Anti-Erb82 Antibody Obtained with Shotgun Scanning Mutagenesis", J. Mol. Biol., 2002, 320, pp. 415-428.
Brown et al., "Tolerance to Single, but Not Multiple, Amino Acid Replacements in Antibody VH CDR2", J. Immunol., 1996, 156, pp. 3285-3291.
International Search Report PCT/US2018/024296 mailed Jun. 22, 2018.
Guido, Rafael V.C. et al. "Virtual Screening and Its Integration with Modern Drug Design Technologies" (2008) Current Medicinal Chemistry, vol. 15, 37-46.
Aagaard, Lars et al. "RNAi therapeutics: Principles, prospects and challenges" (2007) Advanced Drug Delivery Reviews, vol. 59, 75-86.
Warzocha, Krzysztof et al. "Antisense Strategy: Biological Utility and Prospects in the Treatment of Hematological Malignancies" (1997) Leukemia and Lymphoma, vol. 24, 267-281.
McKeague, Maureen et al. "Challenges and Opportunities for Small Molecule Aptamer Development" (2012) Journal of Nucleic Acids, Article ID: 748913, 20 pgs.
Clark, James D. et al. "Discovery and Development of Janus Kinase (JAK) Inhibitors for Inflammatory Diseases" (2014) American Chemical Society, 5023-5038.
Scheibe, Kristina et al. "Inhibiting Interleukin 36 Receptor Signaling Reduces Fibrosis in Mice with Chronic Intestinal Inflammation" (2019) Gastroenterology, vol. 156, No. 4, 1082-1097.
International Search Report for PCT/US2019/021296 mailed Feb. 27, 2020.
Qin, Jian-Zhong et al. "Role of NF-κB in the Apoptotic-resistant Phenotype of Keratinocytes" (1999) vol. 274, No. 53, 37957-37964.
Clinical Trials "A Study to Evaluate the Efficacy and Safety of ANB019 in Subjects With Palmoplantar Pustulosis (PPP)" NCT03633396, (2019) clinicaltrails.gov, 8 pgs.
Bachelez, Trial of Spesolimab for Generalized Pustular Psoriasis, New England Journal of Medicine, 2021, vol. 385, p. 2431-2440.
Burden, The Generalized Pustular Psoriasis Physician Global Assessment score, Research Letters, downloaded from https://academic. oupcom/bjd/article/189/1/138/7131301 by guest on May 6, 2024.
International Search Report and Written Opinion for PCT/US2024/018981 mailed Jul. 17, 2024.
Bai, Treatment of Netherton syndrome with spesolimab, JEADV, 2024, vol. 10, p. 1-2.
Bork, Powers and Pitfalls in Sequence Analysis: The 70% Hurdle, Genome Res., 2000, vol. 10, p. 398-400.
Skolnick, From genes to protein structure and function: novel applications of computational approaches in the genomic era, Tibtech, 2000, vol. 18, 6 pages.
Kulmanov, DeepGO: predicting protein functions from sequence and interaction using a deep ontology-aware classifier, Bioinformatics, 2018, vol. 34, p. 660-668.
Ma, "Rapid Response to Spesolimab in a patient with severe refractory pyoderma gangenosum", Clin. Exp. Dermatol., vol. 49, 2024, p. 82-84.
ClinicalTrials.gov., "A study to test Whether BI 655130 (Spesolimab) prevents Flare-ups in patients with generalized Pustular Psoriasis", NCT04399837, Dec. 14, 2023, 15 pages.

WHO Drug Information, International Nonproprietary Names for Pharmaceutical Substances (INN), Recommended International Proprietary Names 81, vol. 33, No. 1, 2019, p. 1-4.
Walpole, The weight of nations: an estimation of adult human Biomass, BVMC Public Health, 2012, vol. 12, p. 1-6.
Fukaura, Targeting IL-36 in Inflammatory Skin Diseases, BioDrugs, 2023, vol. 37, p. 279-293.
Anaptysbio Reports Harp Phase 2 Top-line Data of Imsidolimab in Moderate -to-severe hidradenitis suppurativa, AnatysBio Reports, Inc., Aug. 31, 2022, p. 1-5.
Burden, Clinical Disease Measures in Generalized Pustular Psoriasis, American Journal of Clinical Dermatology, 2022, vol. 23, Supp. 1, p. 539-550.
Khan, Adjustable Locks and Flexible keys, The Journal of immunology, vol. 192, 2014, p. 5398-5405.
Poosarla, Computational de novo Design of antibodies binding to a peptide with high affinity, Biotechnol. Bioeng., vol. 114, 2017, p. 1331-1342.
Goel, Plasticity within the antigen-Combining Site may manifest as molecular minicry in the humoral immune response, The Journal of immunology, vol. 173, 2004, p. 7358-7367.
Vattekatte, Discrete analysis of camelid variable domains, PeerJ, DOI: 10.7717/peerj.8408, eCollection 2020, 28 pages.
Abstract cited herein for CN107362351, Shanghai Children's, dated Nov. 21, 2017, 10 pages.
Uchiyama, Liquid Formulation for antibody drugs, Biochemica Acta, vol. 1844, No. 11, 2014, p. 2041-2052.
Daugherty, Formulation and delivery issues for monoclonal Antibody therapeutics, Current trends in Monocl. Antib. Devel. and Manufact., Chapter 8, 2010, p. 103-129.
Whitaker, A formulation Development Approach to Identify and Select Stable Ultra High Concetration Monoclonal Antibody Formulations with Reduced Viscosities, J. of Pharm. Sci., vol. 106, No. 11, 2017, p. 3230-3241.
Morita, et al., Efficacy and safety of subcutaneous speso for the prevention of generalized pustular psoriasis flares: an international mutlicentre, randomised, placebo controlled trial, The Lancet, vol. 202, 2023, p. 1541-1551.
Baum et al., Pustualr Psoriasis: Molecular pathways and effects of speso in generalized pustular psoriasis, J. of Allergy and Clinical Immunology, vol. 149, 2022, p. 1402-1412.
Alatas et al., Blood microDNA expressions in patients with mild to moderate psoriasis and the relationship between microRNAs and psoriasis activity: Anais Brasileiros de Fermatologica, vol. 95, 2020, p. 702-707.
Delic et al., Integrated microRNA/mRNA expression profiling of the skin of psoriasis patients, J. of Dermatological Science vol. 97, 2010, p. 9-20.
Raaby et al., Changes in mRNA expression precede changes in micro RNA expression in lesional psoriatic skin during treatment with adalimumab, British J. of Dermatology, vol. 173, 2015, p. 436-442.
Morita et al., Design of Effisayil (TM) 2: a Randomised, Double-Blind, Placebo-Controlled Study of Speso in preventing Flares in patients with generalized Pustualr Psoriasis, Dermatology and Therapy, vol. 13, 2022, p. 347-359.
International Search Report for PCT/EP2024/065694 mailed Mar. 15, 2025.
Harusato, IL-36y signaling controls the induced regulatory T-cell Th9 cell balance via NFκB activation and STAT transcription factors, Mucosal Immunolgoy, vol. 10, 2017, 13 pages.
Marrakechi, Interleukin-36-Receptor Antagonist Deficieny and Generalized Pustular Psoriasis, The N. E. Journal of Medicine, vol. 365, 2011, 9 pages.
Marrakechi, Inhibition of the Interleukin-36 Pathway for the treatment of Generalized Pustular Psoriasis, The New England Journal of Medicine, vol. 380, 2019, 3 pages.
Taylor, A transgenic mouse tat expresses a diversity of human sequence heavy and light chain immunoglobulins, Nucleic Acids Research, vol. 20, 1992, p. 6287-6295.
Rankin, Case report of hidradenitis suppurativa, SAGE Medical Case reports, vol. 9, 2021, 4 pages.

(56) References Cited

OTHER PUBLICATIONS

Cella, Validation of the Functional assessment of chronic illness therapy fatigue scale relative to other instumentation in patients with rheumatoid arthritis, J. of Rheumatology, vol. 32, 2015, 9 pages.

Woodworth, Standardizing assessment and reporting of adverse effects in rheumatology clinical trials II, J. of Rheumatology, vol. 34, 2007, 15 pages.

Calabrese, Opportunistic infections and biologic therapies in immune-mediated inflammatory diseases, Research gate, Annals of Rheumatic Diseases, vol. 10, 2015, 12 pages.

Moltrasio, Hidradenitis Suppurativa, A perspective on genetic factors involved in the disease, Biomedicines, vol. 10, 2022, 14 pages.

Greenland, Estimation of a common effect parameter from a sparse foll up data, Biometrics, vol. 41, 1985, 15 pages.

Anon, Research Letter, British J. of Derma., vol. 173, 2015, 4 pages.

Krueger, Hidradenitis suppurativa, new insights into disease mechanisms, Br. J. Derma., vol. 190, 2023, 14 pages.

Hessam, Interleukin-36 in hidradenitis suppurativa, evidence for a distinctive proinflammatory role and a key factor in the development of an inflammatory loop, B. Journal of Derma., vol. 178, 2018, 1 page.

Scala, Hidradenitis Suppurativa, Where we are and where we are going, Cells, vol. 10, 2021, 19 pages.

Zouboulis, Hidradenitis Suppurativa Acne Inversa: criteria for diagnosis, Dermatology, vol. 231, 2015, 7 pages.

Ring, The Follicular skin microbiome in patients with Hidradenitis Suppurativa and healthy controls, JAMA derma., vol. 153, 2017, 20 pages.

Towne, Interleukin (IL)-1F6, IL-1F8, and IL-1F9 signal through IL-1Rrp2 and IL-1RacP to activate the pathway leading to NF-KB and MAPKs*, The J. of Biological Chem, vol. 14, 2004, 12 pages.

Sarkissian, Identification of Biomarkers and critical Eval. of Biomarker validation in Hidradentitis Suppurativa, JAMA Derma., vol. 158, 2022, 27 pages.

Towne, Interleukin-36 (IL 36) ligands require processing for full agonist, J. of Biological Chemistry, vol. 286, 2011, 9 pages.

Gao, Inversa acne a case report and ID of the locus at Chromosome 1p21.2-1q25.3, J. of investigative Derma., vol. 136, 2006, 5 pages.

Suzuki, Phosphorylation in Epidermal Stem cells, vol. 132, 2012, p. 2459-2461.

Dinarello, A clinical Perspective of IL-1B as the gatekeeper of inflammation, Euro. J. of Immunology, vol. 41, 2011, 15 pages.

Webster, The Functional Assessment of Chronic Illness Therapy Measurement system, Bio Med Central, vol. 79, 2003, 7 pages.

Di Caprio II-36 cytokines are increased in acne, Arch. Dermatol. Res., vol. 10, 2017, 6 pages.

Van Straalen, Contribution of genetics to the susceptibility to hidradenitis suppurativa in a large, cross sectional dutch twin cohort, JAMA derma, vol. 156, 2020, 4 pages.

Navrazhina, Epithelialized tunnels are a source of inflammation in hidradenitis suppurativa, J. Allergy Clin. Immunol., vol. 12, 2020, 12 pages.

Thomi, Increeased expression of the interleukin-36 cytokines in lesions of hidradenitis suppurativa, JEADV, vol. 31, 2017, 6 pages.

Jorgensen, Clinical, microbiological, immunological and imaging characteristics of tunnels and fistulas in hidradenitis suppurativa, Experimental Dermatology, vol. 29, 2019, 6 pages.

Revillet, Bacterial pathogens associated with Hidradenitis Suppurativa, France, Emerginv infectious diseases, vol. 20, 2014, 9 pages.

Winthrop, Opportunistic infections and biologic therapies in immune mediated inflammatory diseases, vol. 1, 2015, 12 pages.

Bonnekoh, Spectrum of genetic autoinflammatory diseases presenting with cutaneous symptoms, Acta Derm Venereol., vol. 100, 2020, p. 140-151.

Bai, Studies of mouse models of allergic disease, Chinese Journal of Comparative Medicine, vol. 2, 2020, 7 pages, Abstract only.

Anon, Anaptybio Reports Harp Phase 2 top-line data of imsidolimab in moderate to severe hidradenitis suppurativa, Anaptysbio, 2016, 6 pages.

Weiss, Neutrophilic Dermatoses, Current Dermatology Reports, vol. 11, 2022, 14 pages.

Hunt, The current clinical trial landscape for hidradenitis suppurativa, vol. 13, 2023, 17 pages.

Ferrante, Safety and tolerability of speso in patients with ulcertaive colitis, Exp. Opinion on drug safety, vol. 2, 2023, 12 pages.

Bissonnette, Speso, an anti-interleukin-36 receptor antibody, in patients with moderate ro severe atopic dermatitis, JEADV, vol. 10, 2022, 9 pages.

Guenin, Spesolimab use in treatment of pyoderma gangrenosum, JAAD, vol. 10, 2023, 5 pages.

Alavi, Pyoderma Gangroenosum,Am. J. Clin. Dermatol, vol. 18, 2017, 18 pages.

Mrowietz, Spesolimab, an anti-interleukin-36 receptor antibody, Dermatol. Ther., 2020, 15 pages, published online https://doi/org/10.1007/s13555-021-00504-0.

Oji, Revised nomenclature and classification of inherited ichthyoses, Results of the first ichythyosis Consensus Conference in Sores, 2009, J. Americ. Acad. of Dermatology, vol. 63, 2010, p. 607-641.

Saunte, Diagnostic delay in hidradenitis suppurative is a global problem, Br. J. Dermatol. vol. 173, 2015, p. 1546-1549.

Pink, Mutations in the y-secretase genes NCSTN, PSENEN, and PSEN1 underlie rare forms of hidradentitis suppurativa, J. Invest Dermatol., vol. 132, 2012, p. 2459-2461.

Nomura, A novel NCSTN mutation alone may be sufficient for the devleopment of familial hidradenitis suppurativa, J. Dermatol. Sci., vol. 74, p. 180-182.

Finlay, Dermatology Life Quality index -a simple practical measure for routine clinical use, Clin. Exp. Dermaol., vol. 19, 1994, p. 210-216.

Guet-Recillet, The microbiological landscape of anaerobic infections in hidradenitis suppurativa: A Prospective metageonic Study, vol. 65, 2017, p. 282-291.

Guet-Revillet, Bacterial pathogens associated with hidradenitis suppurativa, France, E, erg. Infect Dis., vol. 20, 2014, p. 1990-1998.

Hurley, Axillary Hyperhidrosis, Apocrine Bromhidrosis, Hidradentitis Suppurativa, and Familal Benign Pemphigus: Surgical Approach, Roenigk & Roenigk's Dermatologic Surgery, Principles and Practice, 2nd Ed., NY, 1996, p. 623-645.

International report on Patentability for PCT/US2024/018981 mailed Sep. 18, 2025.

z-SCORE NORMALIZED EXPRESSION INTENSITIES 4          2          0          -2          -4

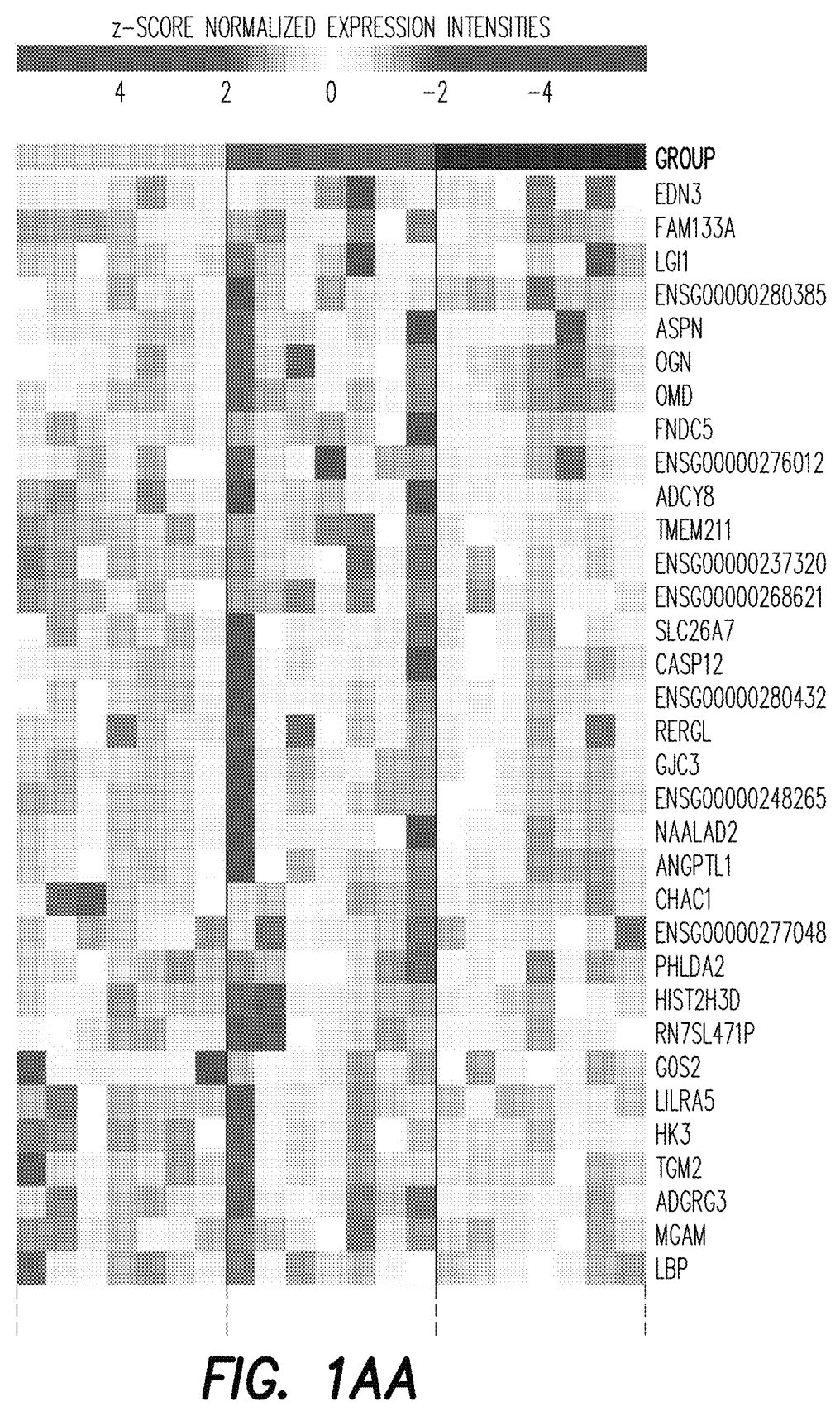

GROUP
EDN3
FAM133A
LGI1
ENSG00000280385
ASPN
OGN
OMD
FNDC5
ENSG00000276012
ADCY8
TMEM211
ENSG00000237320
ENSG00000268621
SLC26A7
CASP12
ENSG00000280432
RERGL
GJC3
ENSG00000248265
NAALAD2
ANGPTL1
CHAC1
ENSG00000277048
PHLDA2
HIST2H3D
RN7SL471P
G0S2
LILRA5
HK3
TGM2
ADGRG3
MGAM
LBP

FIG. 1AA

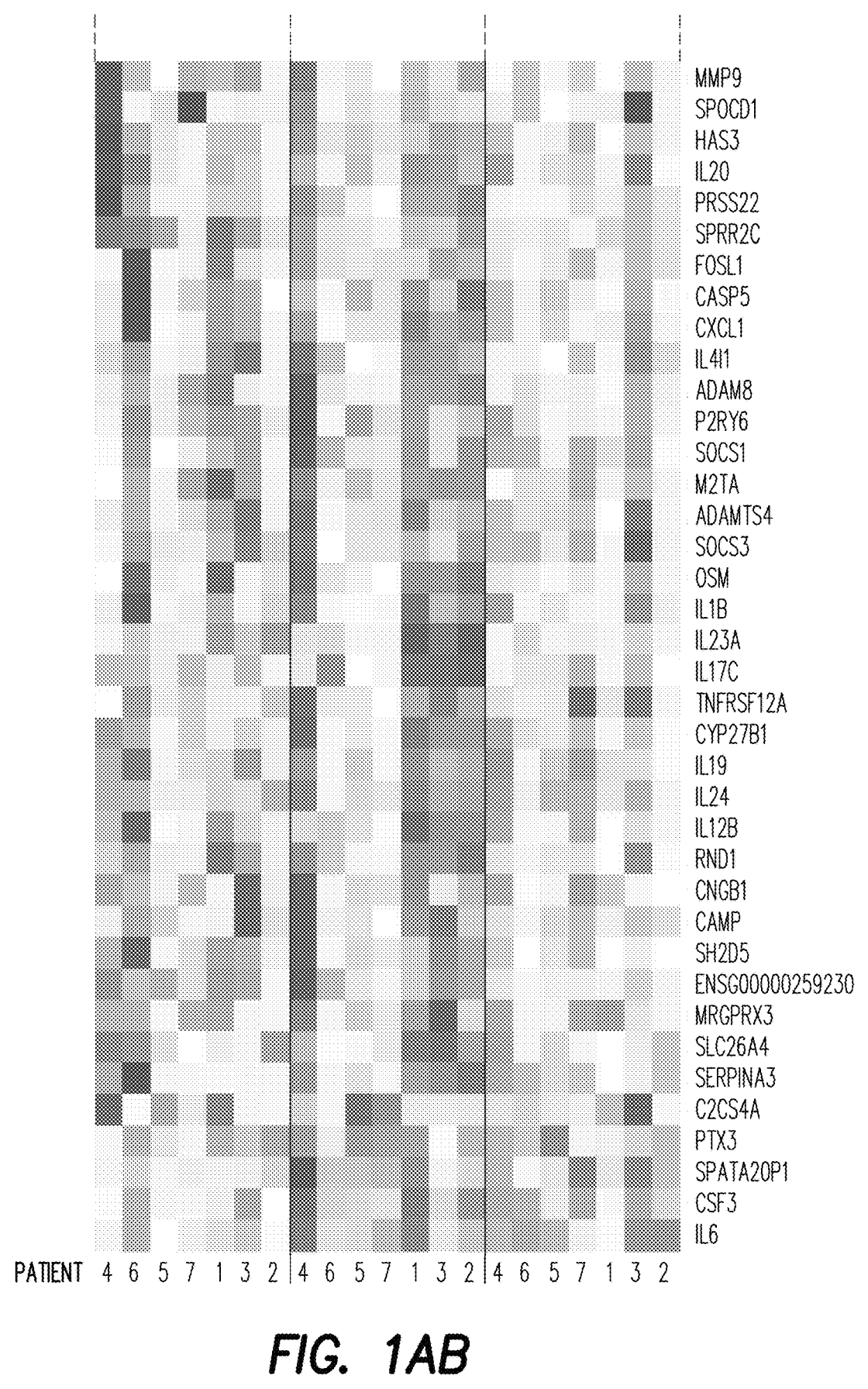

MMP9
SPOCD1
HAS3
IL20
PRSS22
SPRR2C
FOSL1
CASP5
CXCL1
IL4I1
ADAM8
P2RY6
SOCS1
M2TA
ADAMTS4
SOCS3
OSM
IL1B
IL23A
IL17C
TNFRSF12A
CYP27B1
IL19
IL24
IL12B
RND1
CNGB1
CAMP
SH2D5
ENSG00000259230
MRGPRX3
SLC26A4
SERPINA3
C2CS4A
PTX3
SPATA20P1
CSF3
IL6

PATIENT  4 6 5 7 1 3 2 | 4 6 5 7 1 3 2 | 4 6 5 7 1 3 2

FIG. 1AB

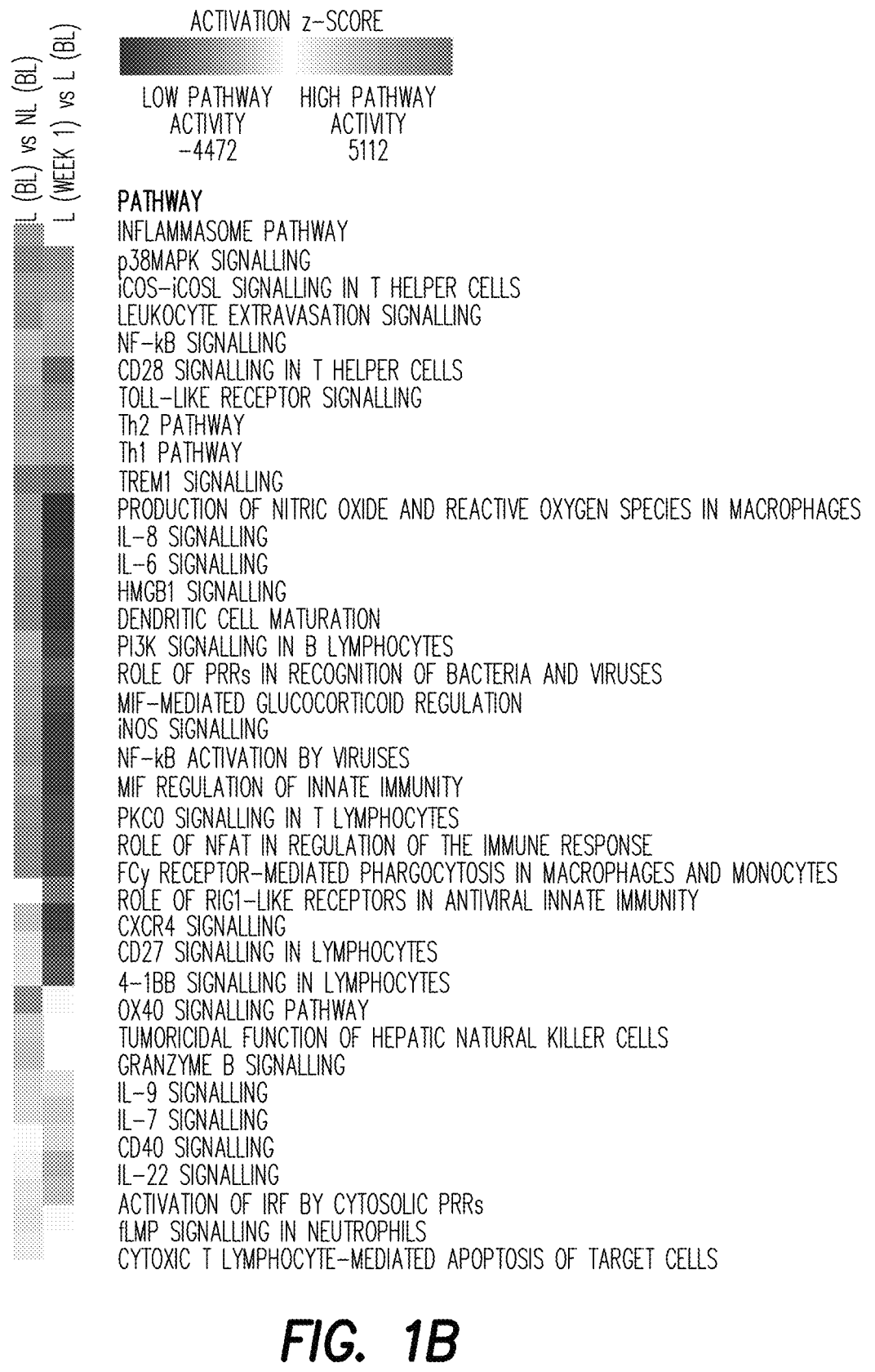

ACTIVATION z-SCORE

LOW PATHWAY      HIGH PATHWAY
  ACTIVITY          ACTIVITY
   -4472             5112

PATHWAY
INFLAMMASOME PATHWAY
p38MAPK SIGNALLING
iCOS-iCOSL SIGNALLING IN T HELPER CELLS
LEUKOCYTE EXTRAVASATION SIGNALLING
NF-kB SIGNALLING
CD28 SIGNALLING IN T HELPER CELLS
TOLL-LIKE RECEPTOR SIGNALLING
Th2 PATHWAY
Th1 PATHWAY
TREM1 SIGNALLING
PRODUCTION OF NITRIC OXIDE AND REACTIVE OXYGEN SPECIES IN MACROPHAGES
IL-8 SIGNALLING
IL-6 SIGNALLING
HMGB1 SIGNALLING
DENDRITIC CELL MATURATION
PI3K SIGNALLING IN B LYMPHOCYTES
ROLE OF PRRs IN RECOGNITION OF BACTERIA AND VIRUSES
MIF-MEDIATED GLUCOCORTICOID REGULATION
iNOS SIGNALLING
NF-kB ACTIVATION BY VIRUISES
MIF REGULATION OF INNATE IMMUNITY
PKCO SIGNALLING IN T LYMPHOCYTES
ROLE OF NFAT IN REGULATION OF THE IMMUNE RESPONSE
FCy RECEPTOR-MEDIATED PHARGOCYTOSIS IN MACROPHAGES AND MONOCYTES
ROLE OF RIG1-LIKE RECEPTORS IN ANTIVIRAL INNATE IMMUNITY
CXCR4 SIGNALLING
CD27 SIGNALLING IN LYMPHOCYTES
4-1BB SIGNALLING IN LYMPHOCYTES
OX40 SIGNALLING PATHWAY
TUMORICIDAL FUNCTION OF HEPATIC NATURAL KILLER CELLS
GRANZYME B SIGNALLING
IL-9 SIGNALLING
IL-7 SIGNALLING
CD40 SIGNALLING
IL-22 SIGNALLING
ACTIVATION OF IRF BY CYTOSOLIC PRRs
fLMP SIGNALLING IN NEUTROPHILS
CYTOXIC T LYMPHOCYTE-MEDIATED APOPTOSIS OF TARGET CELLS

L (BL) vs NL (BL)
L (WEEK 1) vs L (BL)

FIG. 1B

VISIT 12-VISIT 3
LOG²(CPM+0.5)

BL (DAY 1)
WEEK 1 DAY 7
WEEK 2
WEEK 4

2
1
0
-1
-2 z-SCORE NORMALIZED
EXPRESSION INTENSITIES

← MMP9

S100A8
S100A9
S100A12

IL10

CD177

BIOMARKERS ASSOCIATED WITH ANTI-IL-36R ANTIBODY TREATMENT IN GENERALIZED PUSTULAR PSORIASIS

SEQUENCE LISTING

The instant application contains a Sequence Listing which has been submitted electronically in ASCII format and is hereby incorporated by reference in its entirety. Said ASCII copy, created on Feb. 17, 2022 is named 09-0718-US-3-2022-03-10-SL.txt and is 146,122 bytes in size.

TECHNICAL FIELD OF THE INVENTION

This invention generally relates to biomarkers associated with anti-IL-36R antibody treatment in generalized pustular psoriasis (GPP). More specifically, the invention relates to biomarkers associated with spesolimab treatment in GPP. The invention also relates to methods of using the biomarkers disclosed herein.

BACKGROUND OF THE INVENTION

Pustular psoriasis comprises a spectrum of severe chronic or relapsing inflammatory skin conditions with recurrent or persistent eruptions of painful neutrophilic sterile pustules. Patients with pustular psoriasis can present with different clinical phenotypes and a predominant recognised subtype is generalized pustular psoriasis (GPP). GPP is a rare disease characterised by episodes of widespread eruption of macroscopically visible pustules and may be accompanied by systemic inflammation. It is associated with significant morbidity and can be life-threatening without appropriate treatment.

Several studies in GPP have reported overexpression of interleukin-36 (IL-36) in skin lesions and loss-of-function mutations in the gene encoding for the IL-36 receptor (IL-36R) antagonist (IL36RN), as well as mutations in other genes with functional connection with the IL-36 pathway, among others, namely CARD14, APS1S3 and SERPINA3. IL36RN mutations alter the normal function of the IL-36 receptor antagonist, leading to reduced inhibition of the IL-36R pathway due to an imbalanced competitive binding against IL-36a, IL-36P and IL-36γ. This in turn leads to induction of the downstream inflammatory cascade and recruitment of neutrophils, in addition to other innate and adaptive immune cells. IL36RN mutations have been reported in 10-82% of patients with GPP, and an earlier age of onset has been described in patients with GPP who have defective IL36RN mutations. Furthermore, a study investigating the impact of different IL36RN mutations on IL-36Ra protein expression and regulatory function showed that null mutants tend to be preferentially associated with GPP, whereas hypomorphic mutations were found in GPP.

The key role of the IL-36 axis in GPP is further supported by studies demonstrating significant contributions for IL-17A, IL-23, tumour necrosis factor (TNF), IL-1, IL-36 and type 1 interferon in the pathogenesis of GPP lesions. Among the upregulated genes, predominance of IL-1- and IL-36-related transcripts was reported. In addition, strong expression of IL-36a and IL-36γ in keratinocytes proximal to neutrophilic pustules have also been detected in GPP lesions.

Overall, there is sufficient evidence to suggest that the blockade of IL-36R signalling is an appealing targeted therapeutic approach for patients with GPP. Previously, blockade of IL-36R signalling with a single intravenous dose of 10 mg/kg spesolimab, a novel humanised anti-IL-36R monoclonal antibody, in a proof-of-concept Phase I, multicentre, single-arm, open-label study (ClinicalTrials.gov identifier: NCT02978690) showed rapid skin and pustular clearance in patients presenting with an acute GPP flare. However, the inflammatory circuits and cellular interactions driving the pathogenesis of GPP are not yet fully elucidated, and the mechanisms by which these are disrupted by IL-36R blockade are unknown.

There is therefore a need for improved means to follow the efficacy of treatment options against GPP, identify patients that will most benefit from these treatments in GPP, and to determine and adjust the dosages of therapies for patients as may be needed.

SUMMARY OF THE INVENTION

The present invention addresses the above needs and provides biomarkers associated with anti-IL-36R antibody treatment in generalized pustular psoriasis (GPP).

In one embodiment, the present invention provides a method for detecting the presence or absence of a beneficial response in a patient after administration of an anti-interleukin 36 receptor antibody (anti-IL-36R antibody) (e.g., spesolimab), comprising: a) obtaining a biological sample from the patient; b) measuring in said sample the level of expression of one or more biomarkers; c) comparing the level to control value of the level of the biomarkers; and d) determining whether or not the difference in levels between the sample and the control reflects a beneficial response in the patient, wherein the one or more biomarkers comprise genes/proteins associated with the pro-inflammatory mediators (TNF, IL1B, IL6), neutrophil recruitment mediators (CXCL1, CXCL2, CXCL3, CXCL5, CXCL6, CXCL8, CXCR1, CXCR1, CXCR2), neutrophil-expressed transcripts (NCF1, NCF2, NCF4, ELANE) or in keratinocyte activation, differentiation and mediated inflammation transcripts (IL36A, IL36G, IL17C, IL19, IL20, IL22, IL24). In a related embodiment, the one or more biomarkers comprise the genes or proteins listed in Tables 1 and 2.

In one embodiment, the presence or absence of a beneficial response in the patient is detected prior to and after administration of an anti-IL36R antibody or spesolimab.

In one embodiment, the control value of the value of a patient treated with a placebo. In one embodiment, the control value of the value of a patient treated with a placebo and the difference is the difference between the sample from a patient treated with an anti-IL36R antibody or spesolimab and the placebo.

In one embodiment, the level of the gene or the protein of said one or more biomarker is measured. In one embodiment, the patient suffers from GPP.

In one embodiment, the control value is calculated using samples from subjects that do not suffer from GPP. In one embodiment, the control value, for example the placebo value, is determined using samples from known GPP patients, for example from placebo-treated GPP patients. In one embodiment, the control value is determined using at least one previous sample taken from the patient.

In one embodiment, the method further comprises continuing the administration of the anti-IL-36R antibody to the patient if the difference in levels between the sample and the control reflects a beneficial response in the patient. In one embodiment, the method further comprises continuing the administration of the anti-IL-36R antibody to the patient if the difference in levels from a patient treated with the antibody versus the placebo reflects a beneficial response in the patient.

In a further embodiment, the present invention provides a method of determining whether a potential therapeutic agent is efficacious in the treatment of GPP comprising: a) obtaining a first biological sample from a GPP patient prior to being treated with the potential therapeutic agent; b) treating the GPP patient with the potential therapeutic agent; c) obtaining a second biological sample from the GPP patient after being treated with the potential therapeutic agent; d) measuring in said first and second sample the levels of expression of one or more biomarkers; and e) comparing the biomarker levels in the second sample to the levels in the first sample, wherein changes in biomarker levels in the second sample than in the first sample indicate that the potential therapeutic agent is efficacious, and further wherein the one or more biomarkers comprise genes associated with pro-inflammatory mediators (TNF, IL1B, IL6), neutrophil recruitment mediators (CXCL1, CXCL2, CXCL3, CXCL5, CXCL6, CXCL8, CXCR1, CXCR1, CXCR2), neutrophil-expressed transcripts (NCF1, NCF2, NCF4, ELANE) or in keratinocyte activation, differentiation and mediated inflammation transcripts (IL36A, IL36G, IL17C, IL19, IL20, IL22, IL24). In a related embodiment, the one or more biomarkers comprise the genes or proteins listed in Tables 1 and 2.

In one embodiment, said step e) comprises comparing the biomarker levels in the second sample to the levels in the first sample, wherein changes in biomarker levels in the second sample than in the first sample and correlation with improvement in a clinical efficacy measure, e.g., GPPASI scores in case of GPP indicates the potential therapeutic agent is efficacious.

In one embodiment, the method further comprises continuing the treatment of the patient if biomarker levels in the second sample change (e.g., are higher or lower) as compared to the first sample.

In a further embodiment, the present invention provides a method of treating GPP in a subject comprising: determining whether to initiate treatment of the subject, modify the treatment dose, modify the dosing interval, or discontinue treatment, based on the method of any of the preceding claims.

In a further embodiment, the present invention provides a method of monitoring patient response to a GPP treatment comprising:

a) obtaining a first biological sample from the patient;
b) measuring the level of one or more biomarkers in said first biological sample, wherein said one or more biomarkers comprise genes/proteins associated with pro-inflammatory mediators (TNF, IL1B, IL6), neutrophil recruitment mediators (CXCL1, CXCL2, CXCL3, CXCL5, CXCL6, CXCL8, CXCR1, CXCR1, CXCR2), neutrophil-expressed transcripts (NCF1, NCF2, NCF4, ELANE) or in keratinocyte activation, differentiation and mediated inflammation transcripts (IL36A, IL36G, IL17C, IL19, IL20, IL22, IL24) or wherein said one or more biomarkers comprise the genes or proteins listed in Tables 1 and 2;
c) administering a treatment compound to the patient;
d) obtaining a second biological sample from the patient;
e) measuring the level of said one or more biomarkers in said second biological sample; and
f) comparing the levels of the one or more biomarkers obtained from first and second biological samples;

wherein a change in the level of the one or more biomarkers in the second biological sample indicates an effective response. In one aspect, a change in the level of the one or more biomarkers in the second biological sample and correlation with improvement in a clinical efficacy measure, e.g., GPPASI scores in case of GPP indicates an effective response.

In a further embodiment, the present invention provides a method for monitoring patient compliance with a drug treatment protocol for GPP comprising:

a) obtaining a biological sample from said patient;
b) measuring the level of one or more biomarkers, wherein the one or more biomarkers comprise genes/ proteins associated with pro-inflammatory mediators (TNF, IL1B, IL6), neutrophil recruitment mediators (CXCL1, CXCL2, CXCL3, CXCL5, CXCL6, CXCL8, CXCR1, CXCR1, CXCR2), neutrophil-expressed transcripts (NCF1, NCF2, NCF4, ELANE) or in keratinocyte activation, differentiation and mediated inflammation transcripts (IL36A, IL36G, IL17C, IL19, IL20, IL22, IL24) or wherein said one or more biomarkers comprise the genes or proteins listed in Tables 1 and 2; and
c) determining if the level is changed in the patient sample compared to the level in a control untreated sample;
wherein a change in the level indicates patient compliance with said drug treatment protocol.

In one embodiment, in any one of the methods above, the level of the one or more biomarkers in the second biological sample is changed by at least about 20%, 25%, 30%, 35%, 40%, 45%, 50%, 55%, 60%, 65%, 65%, 70%, 75%, 80%, 85%, 90%, or 95% or more as compared to the level in the first biological sample.

In one embodiment, in any one of the methods above, the biological sample is a skin biopsy, blood, plasma or serum sample. In one embodiment, in any one of the methods above, the anti-IL-36R antibody is spesolimab. In one embodiment, in any one of the methods above, the levels of biomarkers are determined by RNA sequencing or ELISA or another protein assay. In one embodiment, the biomarkers are the differentially expressed genes in skin.

In one embodiment, the present invention further provides a method of selecting a patient, for example using a method disclosed herein. In one embodiment, the present invention further provides a method of enriching a patient population for patients expected to have a beneficial response after treatment with an anti-IL-36R antibody, for example using a method of the present invention. In one embodiment, the present invention further provides a method of enriching a patient population for patients expected to have a beneficial response prior to or early after treatment with an anti-IL-36R antibody, for example using a method of the present invention.

In one embodiment, in any one of the methods above, the anti-IL-36R antibody or an antigen binding fragment thereof as disclosed below.

In one embodiment, the anti-IL-36R antibody or antigen-binding fragment thereof comprises a) a light chain variable region comprising the amino acid sequence of SEQ ID NO: 26 (L-CDR1); the amino acid sequence of SEQ ID NO: 35, 102, 103, 104, 105 106 or 140 (L-CDR2); the amino acid sequence of SEQ ID NO: 44 (L-CDR3); and b) a heavy chain variable region comprising the amino acid sequence of SEQ ID NO: 53 (H-CDR1); the amino acid sequence of SEQ ID NO: 62, 108, 109, 110 or 111 (H-CDR2); the amino acid sequence of SEQ ID NO: 72 (H-CDR3).

In one embodiment, the anti-IL-36R antibody or antigen-binding fragment thereof comprises:

I. a) a light chain variable region comprising the amino acid sequence of SEQ ID NO: 26 (L-CDR1); the amino acid sequence of SEQ ID NO: 102 (L-CDR2); the amino acid sequence of SEQ ID NO: 44 (L-CDR3); and b) a heavy chain variable region comprising the amino acid sequence of SEQ ID NO: 53 (H-CDR1); the amino acid sequence of SEQ ID NO: 62, 108, 109, 110 or 111 (H-CDR2); the amino acid sequence of SEQ ID NO: 72 (H-CDR3).

II. a) a light chain variable region comprising the amino acid sequence of SEQ ID NO: 26 (L-CDR1); the amino acid sequence of SEQ ID NO: 103 (L-CDR2); the amino acid sequence of SEQ ID NO: 44 (L-CDR3); and b) a heavy chain variable region comprising the amino acid sequence of SEQ ID NO: 53 (H-CDR1); the amino acid sequence of SEQ ID NO: 62, 108, 109, 110 or 111 (H-CDR2); the amino acid sequence of SEQ ID NO: 72 (H-CDR3).

III. a) a light chain variable region comprising the amino acid sequence of SEQ ID NO: 26 (L-CDR1); the amino acid sequence of SEQ ID NO: 104 (L-CDR2); the amino acid sequence of SEQ ID NO: 44 (L-CDR3); and b) a heavy chain variable region comprising the amino acid sequence of SEQ ID NO: 53 (H-CDR1); the amino acid sequence of SEQ ID NO: 62, 108, 109, 110 or 111 (H-CDR2); the amino acid sequence of SEQ ID NO: 72 (H-CDR3).

IV. a) a light chain variable region comprising the amino acid sequence of SEQ ID NO: 26 (L-CDR1); the amino acid sequence of SEQ ID NO: 105 (L-CDR2); the amino acid sequence of SEQ ID NO: 44 (L-CDR3); and b) a heavy chain variable region comprising the amino acid sequence of SEQ ID NO: 53 (H-CDR1); the amino acid sequence of SEQ ID NO: 62, 108, 109, 110 or 111 (H-CDR2); the amino acid sequence of SEQ ID NO: 72 (H-CDR3).

V. a) a light chain variable region comprising the amino acid sequence of SEQ ID NO: 26 (L-CDR1); the amino acid sequence of SEQ ID NO: 106 (L-CDR2); the amino acid sequence of SEQ ID NO: 44 (L-CDR3); and b) a heavy chain variable region comprising the amino acid sequence of SEQ ID NO: 53 (H-CDR1); the amino acid sequence of SEQ ID NO: 62, 108, 109, 110 or 111 (H-CDR2); the amino acid sequence of SEQ ID NO: 72 (H-CDR3).

VI. a) a light chain variable region comprising the amino acid sequence of SEQ ID NO: 26 (L-CDR1); the amino acid sequence of SEQ ID NO: 140 (L-CDR2); the amino acid sequence of SEQ ID NO: 44 (L-CDR3); and b) a heavy chain variable region comprising the amino acid sequence of SEQ ID NO: 53 (H-CDR1); the amino acid sequence of SEQ ID NO: 62, 108, 109, 110 or 111 (H-CDR2); the amino acid sequence of SEQ ID NO: 72 (H-CDR3).

In one embodiment, the anti-IL-36R antibody or antigen-binding fragment thereof comprises:

(i) a light chain variable region comprising the amino acid sequence of SEQ ID NO: 77; and a heavy chain variable region comprising the amino acid sequence of SEQ ID NO: 87; or (ii) a light chain variable region comprising the amino acid sequence of SEQ ID NO: 77; and a heavy chain variable region comprising the amino acid sequence of SEQ ID NO: 88; or (iii) a light chain variable region comprising the amino acid sequence of SEQ ID NO: 77; and a heavy chain variable region comprising the amino acid sequence of SEQ ID NO: 89; or (iv) a light chain variable region comprising the amino acid sequence of SEQ ID NO: 80; and a heavy chain variable region comprising the amino acid sequence of SEQ ID NO: 87; or (v) a light chain variable region comprising the amino acid sequence of SEQ ID NO: 80; and a heavy chain variable region comprising the amino acid sequence of SEQ ID NO: 88; or (vi) a light chain variable region comprising the amino acid sequence of SEQ ID NO: 80; and a heavy chain variable region comprising the amino acid sequence of SEQ ID NO: 89; or (vii) a light chain variable region comprising the amino acid sequence of SEQ ID NO: 85; and a heavy chain variable region comprising the amino acid sequence of SEQ ID NO: 100; or (viii) a light chain variable region comprising the amino acid sequence of SEQ ID NO: 85; and a heavy chain variable region comprising the amino acid sequence of SEQ ID NO:101; or (ix) a light chain variable region comprising the amino acid sequence of SEQ ID NO: 86; and a heavy chain variable region comprising the amino acid sequence of SEQ ID NO: 100; or (x) a light chain variable region comprising the amino acid sequence of SEQ ID NO: 86; and a heavy chain variable region comprising the amino acid sequence of SEQ ID NO:101.

In one embodiment, the anti-IL-36R antibody or antigen-binding fragment thereof comprises:

i. a light chain comprising the amino acid sequence of SEQ ID NO: 115; and a heavy chain comprising the amino acid sequence of SEQ ID NO: 125; or ii. a light chain comprising the amino acid sequence of SEQ ID NO: 115; and a heavy chain comprising the amino acid sequence of SEQ ID NO: 126; or iii. a light chain comprising the amino acid sequence of SEQ ID NO: 115; and a heavy chain comprising the amino acid sequence of SEQ ID NO: 127; or iv. a light chain comprising the amino acid sequence of SEQ ID NO: 118; and a heavy chain comprising the amino acid sequence of SEQ ID NO: 125; or v. a light chain comprising the amino acid sequence of SEQ ID NO: 118; and a heavy chain comprising the amino acid sequence of SEQ ID NO: 126; or vi. a light chain comprising the amino acid sequence of SEQ ID NO: 118; and a heavy chain comprising the amino acid sequence of SEQ ID NO: 127; or vii. a light chain comprising the amino acid sequence of SEQ ID NO: 123; and a heavy chain comprising the amino acid sequence of SEQ ID NO: 138; or viii. a light chain comprising the amino acid sequence of SEQ ID NO: 123; and a heavy chain comprising the amino acid sequence of SEQ ID NO: 139; or ix. a light chain comprising the amino acid sequence of SEQ ID NO: 124; and a heavy chain comprising the amino acid sequence of SEQ ID NO: 138.

In one embodiment, the anti-IL-36R antibody is spesolimab, Antibody B1, Antibody B2, Antibody B3, Antibody B4, Antibody B5, Antibody B6, Antibody C1, Antibody C2, or Antibody C3.

In one embodiment, the anti-IL-36R antibody is an antibody as disclosed in WO2013/074569, WO2016/168542 or WO2020/018503, the content of each of which is incorporated heron by reference.

In another embodiment, the present invention relates to a composition comprising a biological sample from a patient with GPP and an agent for detecting absence or presence or level of one or more biomarkers comprise the genes or proteins listed in Tables 1 and 2. In a related embodiment, the agent is, for example, an antibody against any of the biomarkers listed in Table 1 and 2.

BRIEF DESCRIPTION OF THE FIGURES

FIG. 1A-1C shows the differentially expressed genes (DEGs) in GPP skin lesions after treatment with spesolimab. FIG. 1A shows a heatmap of 71 DEGs between lesional skin 1 week after treatment with spesolimab compared with baseline lesional skin (fold change ≥2, adjusted P≤0.05). FIG. 1B shows spesolimab treatment inverts over-activated pathways 1 week after treatment. Ingenuity Pathway Analysis of DEGs in lesional versus non-lesional skin at baseline and in lesional skin 1 week after treatment compared with baseline. FIG. 1C shows percent improvement of pathway/process representative marker genes (*P≤0.05). BL, baseline; DEG, differentially expressed gene; FCH, fold change; GPP, generalized pustular psoriasis; L, lesional; NL, nonlesional.

FIG. 2A shows a heatmap of changes in clinical scores and immunohistochemical biomarkers from baseline to Week 1 in each patient following spesolimab treatment. Red cells denote percent change from baseline 100; grey cells denote missing values. FIG. 2B shows the changes in expression of neutrophil elastase, IL-36γ, CD3, CD11c and lipocalin-2 expressed in GPP lesions before (baseline) and after (Weeks 1 and 4) treatment with spesolimab. Representative histopathology is shown. BL, baseline; D, dermis; E, epidermis; GPP, generalized pustular psoriasis; GPPASI, Generalized Pustular Psoriasis Area and Severity Index.

FIG. 3A shows the changes (adjusted P≤0.05, fold change ≥2) in selected genes in blood of patients with GPP (n=7) after spesolimab treatment throughout Week 1 (Visits 2-9), Week 2 (Visit 10) and Week 4 (Visit 12). FIG. 3B shows the Ingenuity Pathway Analysis of DEGs in blood at baseline and at Weeks 1, 2 and 4 after treatment with spesolimab. FIG. 3C shows the heatmap of changes in clinical scores and serum biomarkers from baseline over time in each patient after spesolimab treatment. Red cells denote percent change from baseline 100. At Weeks 12 and 20, one patient (Patient 5) received methotrexate and was classified as receiving rescue treatment. BL, baseline; CPM, counts per million; DEG, differentially expressed gene; GPP, generalized pustular psoriasis; GPPASI, Generalized Pustular Psoriasis Area and Severity Index.

DETAILED DESCRIPTION

Figure 1C:
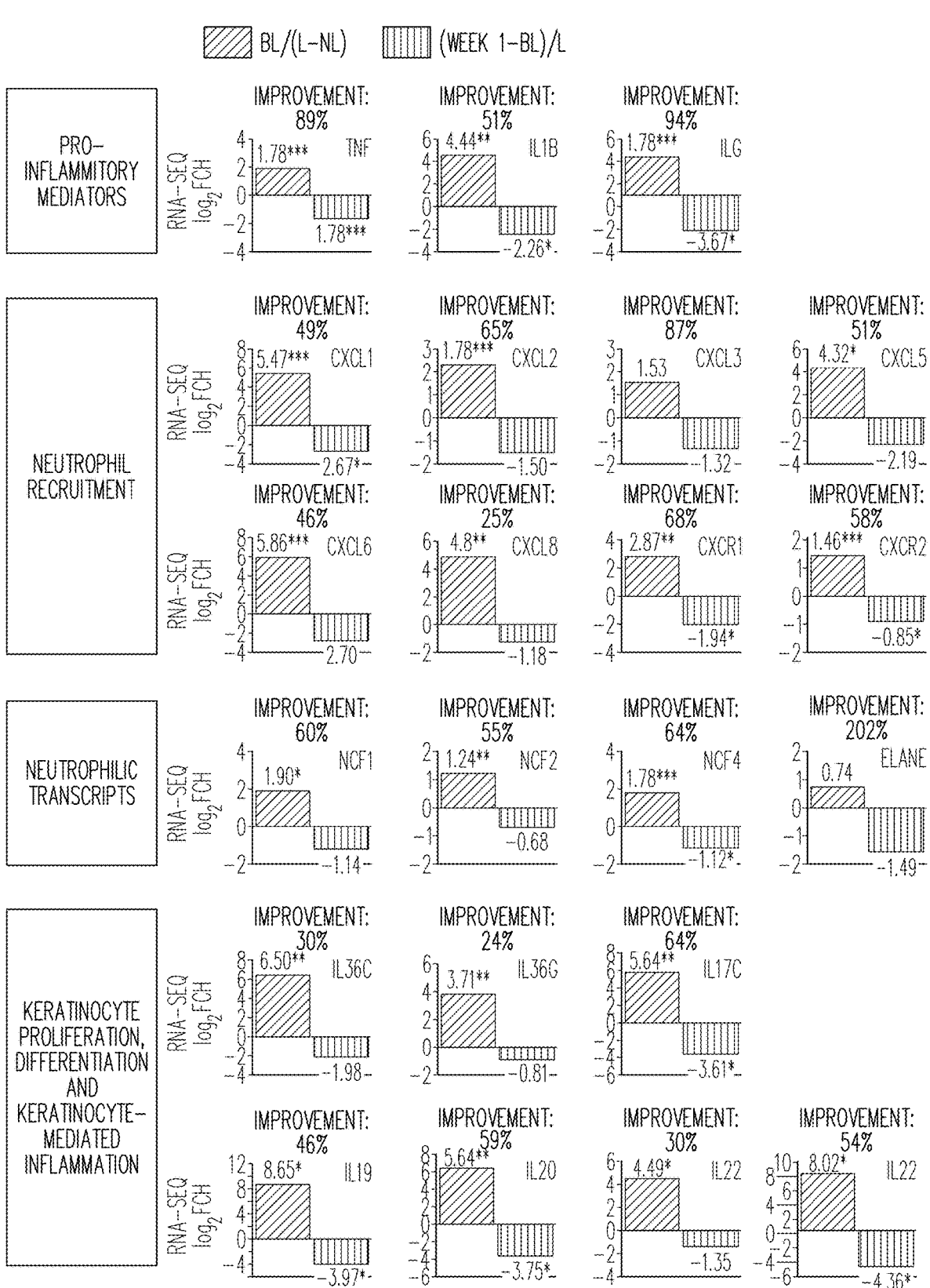

GPP symptoms of varying severity occur in most patients and may be idiopathic or triggered by external stimuli, such as infection, corticosteroid use or withdrawal, stress or pregnancy. Moderate or severe GPP cause significant morbidity and mortality due to tender, painful skin lesions, extreme fatigue, high fever, peripheral blood neutrophilia and acute phase response and sepsis. The acute phase is associated with a mean duration of hospitalization of 10 days (range 3-44 days). The observed mortality rate of 7% reported in a retrospective study with 102 GPP cases seen in a tertiary hospital in Johor, Malaysia is likely an underestimate as not all GPP patients were included in the study. Mortality rates are also likely underestimated due to lack of identifying the cause of death as GPP and are largely driven by infectious complications and extra-cutaneous organ manifestations such as renal, hepatic, respiratory and cardiac failure. After responding to treatment or spontaneous flare cessation, it is estimated that up to 50% of patients may suffer from chronic GPP characterized by persistent erythema and scaling that may also include joint symptoms. Based on these limitations, current therapeutic options are not suitable for life-long treatment and do not provide sustained responses in most patients.

The classic presentation of GPP flares as described by von Zumbusch is strongly correlated with polymorphisms in the IL36-R signaling pathway. Individuals with loss-of-function mutations of the IL36RN gene which encodes an endogenous IL36R antagonist (IL-36RN) have dramatically higher incidence of GPP, indicating that uncontrolled upregulation of IL36 signaling due to defective IL36RN antagonism leads to the inflammatory episodes observed in GPP. Genetic human studies have demonstrated the occurrence of GPP clusters in families with a loss of function mutation in IL36RN, which results in uncontrolled IL36R signaling. Mutations in other genes linked to the IL36 pathway such as CARD14 also lead to GPP. Moreover, a recent meta-analysis investigated 233 published GPP cases. They found that 49 (21.0%) of 233 cases carried recessive IL36RN alleles. Those 49 recessive IL36RN alleles defined a GPP phenotype characterized by early onset and high risk of systemic inflammation.

As stated before, there is sufficient evidence to suggest that the blockade of IL-36R signalling is an appealing targeted therapeutic approach for patients with GPP. Previously, blockade of IL-36R signalling with a single intravenous dose of 10 mg/kg spesolimab, a novel humanised anti-IL-36R monoclonal antibody, in a proof-of-concept Phase I, multicentre, single-arm, open-label study (ClinicalTrials.gov identifier: NCT02978690) showed rapid skin and pustular clearance in patients presenting with an acute GPP flare. However, the inflammatory circuits and cellular interactions driving the pathogenesis of GPP are not yet fully elucidated, and the mechanisms by which these are disrupted by IL-36R blockade are unknown. To investigate this, the molecular profiles from skin biopsies were examined in patients with GPP and compared with those from healthy volunteers. In addition, changes in the molecular, histopathological and protein expression profiles in blood and skin post spesolimab treatment in patients with GPP participating in the aforementioned clinical trial were examined and are reported herein.

Therefore, the present invention provides biomarkers associated with anti-IL36R antibody (e.g., spesolimab) treatment in GPP.

In one embodiment, the present invention provides a method for detecting the presence or absence of a beneficial response in a patient after administration of an anti-interleukin 36 receptor antibody (anti-IL-36R antibody) (e.g., spesolimab), comprising: a) obtaining a biological sample from the patient; b) measuring in said sample the level of expression of one or more biomarkers; c) comparing the level to control value of the level of the biomarkers; and d)

determining whether or not the difference in levels between the sample and the control reflects a beneficial response in the patient, wherein the one or more biomarkers comprise genes/proteins associated with the pro-inflammatory mediators (TNF, IL1B, IL6), neutrophil recruitment mediators (CXCL1, CXCL2, CXCL3, CXCL5, CXCL6, CXCL8, CXCR1, CXCR1, CXCR2), neutrophil-expressed transcripts (NCF1, NCF2, NCF4, ELANE) or in keratinocyte activation, differentiation and mediated inflammation transcripts (IL36A, IL36G, IL17C, IL19, IL20, IL22, IL24), CSF3, IL24, IL19, IL20, IL6, IL17C, IL12B, RN7SL471P, PTX3, MRGPRX3, LBP, CAMP, IL23A, RND1, ADAMTS4, SPOCD1, MRPL12, CXCL1, GOS2, SPATA20P1, SH2D5, SOCS3, PHLDA2, MGAM, SLC26A4, MMP9, PADI4, FOSL1, PDCD1, MT2A, SPRR2C, P2RY6, C2CD4A, OSM, IL1B, CYP27B1, PRSS22, FCGBP, LILRA5, SERPINA3, SNA11, TGM2, CNGB1, MAMDC4, MT1G, JUNB, SOCS1 or CASP5. In a related embodiment, the one or more biomarkers comprise the genes or proteins listed in Tables 1 and 2.

In one embodiment, the presence or absence of a beneficial response in the patient is detected prior to and after administration of an anti-IL36R antibody or spesolimab.

In one embodiment, the control value of the value of a patient treated with a placebo. In one embodiment, the control value of the value of a patient treated with a placebo and the difference is the difference between the sample from a patient treated with an anti-IL36R antibody or spesolimab and the placebo.

In one embodiment, the level of the gene or the protein of said one or more biomarker is measured. In one embodiment, the patient suffers from GPP.

In one embodiment, the control value is calculated using samples from subjects that do not suffer from GPP. In one embodiment, the control value, for example the placebo value, is determined using samples from known GPP patients, for example from placebo-treated GPP patients. In one embodiment, the control value is determined using at least one previous sample taken from the patient.

In one embodiment, the method further comprises continuing the administration of the anti-IL-36R antibody to the patient if the difference in levels between the sample and the control reflects a beneficial response in the patient. In one embodiment, the method further comprises continuing the administration of the anti-IL-36R antibody to the patient if the difference in levels from a patient treated with the antibody versus the placebo reflects a beneficial response in the patient.

In a further embodiment, the present invention provides a method of determining whether a potential therapeutic agent is efficacious in the treatment of GPP comprising: a) obtaining a first biological sample from a GPP patient prior to being treated with the potential therapeutic agent; b) treating the GPP patient with the potential therapeutic agent; c) obtaining a second biological sample from the GPP patient after being treated with the potential therapeutic agent; d) measuring in said first and second sample the levels of expression of one or more biomarkers; and e) comparing the biomarker levels in the second sample to the levels in the first sample, wherein changes (e.g., lower or higher) in biomarker levels in the second sample than in the first sample indicate that the potential therapeutic agent is efficacious, and further wherein the one or more biomarkers comprise genes associated with pro-inflammatory mediators (TNF, IL1B, IL6), neutrophil recruitment mediators (CXCL1, CXCL2, CXCL3, CXCL5, CXCL6, CXCL8, CXCR1, CXCR1, CXCR2), neutrophil-expressed transcripts (NCF1, NCF2, NCF4, ELANE) or in keratinocyte activation, differentiation and mediated inflammation transcripts (IL36A, IL36G, IL17C, IL19, IL20, IL22, IL24), CSF3, IL24, IL19, IL20, IL6, IL17C, IL12B, RN7SL471P, PTX3, MRGPRX3, LBP, CAMP, IL23A, RND1, ADAMTS4, SPOCD1, MRPL12, CXCL1, GOS2, SPATA20P1, SH2D5, SOCS3, PHLDA2, MGAM, SLC26A4, MMP9, PADI4, FOSL1, PDCD1, MT2A, SPRR2C, P2RY6, C2CD4A, OSM, IL1B, CYP27B1, PRSS22, FCGBP, LILRA5, SERPINA3, SNA11, TGM2, CNGB1, MAMDC4, MT1G, JUNB, SOCS1 or CASP5. In a related embodiment, the one or more biomarkers comprise the genes or proteins listed in Tables 1 and 2. In one embodiment, said step e) comprises comparing the biomarker levels in the second sample to the levels in the first sample, wherein changes (e.g., lower or higher) in biomarker levels in the second sample than in the first sample and correlation with improvement in a clinical efficacy measure, e.g., GPPASI scores in case of GPP indicates the potential therapeutic agent is efficacious. In one embodiment, the method further comprises continuing the treatment of the patient if biomarker levels in the second sample change (e.g., are higher or lower) as compared to the first sample.

In a further embodiment, the present invention provides a method of treating GPP in a subject comprising: a) determining whether to initiate treatment of the subject, modify the treatment dose, modify the dosing interval, or discontinue treatment, based on the method of any of the preceding claims; and b) modifying the treatment regimen based on the determination.

In a further embodiment, the present invention provides a method of monitoring patient response to a GPP treatment comprising:

a) obtaining a first biological sample from the patient;
b) measuring the level of one or more biomarkers in said first biological sample, wherein said one or more biomarkers comprise genes/proteins associated with pro-inflammatory mediators (TNF, IL1B, IL6), neutrophil recruitment mediators (CXCL1, CXCL2, CXCL3, CXCL5, CXCL6, CXCL8, CXCR1, CXCR1, CXCR2), neutrophil-expressed transcripts (NCF1, NCF2, NCF4, ELANE) or in keratinocyte activation, differentiation and mediated inflammation transcripts (IL36A, IL36G, IL17C, IL19, IL20, IL22, IL24), CSF3, IL24, IL19, IL20, IL6, IL17C, IL12B, RN7SL471P, PTX3, MRGPRX3, LBP, CAMP, IL23A, RND1, ADAMTS4, SPOCD1, MRPL12, CXCL1, GOS2, SPATA20P1, SH2D5, SOCS3, PHLDA2, MGAM, SLC26A4, MMP9, *PADI*4, FOSL1, PDCD1, MT2A, SPRR2C, P2RY6, C2CD4A, OSM, IL1B, CYP27B1, PRSS22, FCGBP, LILRA5, SERPINA3, SNA11, TGM2, CNGB1, MAMDC4, MT1 G, JUNB, SOCS1 or CASP5; or wherein said one or more biomarkers comprise the genes or proteins listed in Tables 1 and 2;
c) administering a treatment compound to the patient;
d) obtaining a second biological sample from the patient;
e) measuring the level of said one or more biomarkers in said second biological sample; and
f) comparing the levels of the one or more biomarkers obtained from first and second biological samples;
wherein a change (e.g., high, low) in the level of the one or more biomarkers in the second biological sample indicates an effective response. In one aspect, a change (e.g., high, low) in the level of the one or more biomarkers in the second biological sample and correlation with improvement in a clinical efficacy measure, e.g., GPPASI scores in case of GPP indicates an effective response.

In a further embodiment, the present invention provides a method for monitoring patient compliance with a drug treatment protocol for GPP comprising:

a) obtaining a biological sample from said patient;

b) measuring the level of one or more biomarkers, wherein the one or more biomarkers comprise genes/proteins associated with pro-inflammatory mediators (TNF, IL1B, IL6), neutrophil recruitment mediators (CXCL1, CXCL2, CXCL3, CXCL5, CXCL6, CXCL8, CXCR1, CXCR1, CXCR2), neutrophil-expressed transcripts (NCF1, NCF2, NCF4, ELANE) or in keratinocyte activation, differentiation and mediated inflammation transcripts (IL36A, IL36G, IL17C, IL19, IL20, IL22, IL24), CSF3, IL24, IL19, IL20, IL6, IL17C, IL12B, RN7SL471P, PTX3, MRGPRX3, LBP, CAMP, IL23A, RND1, ADAMTS4, SPOCD1, MRPL12, CXCL1, GOS2, SPATA20P1, SH2D5, SOCS3, PHLDA2, MGAM, SLC26A4, MMP9, *PADI*4, FOSL1, PDCD1, MT2A, SPRR2C, P2RY6, C2CD4A, OSM, IL1B, CYP27B1, PRSS22, FCGBP, LILRA5, SERPINA3, SNA11, TGM2, CNGB1, MAMDC4, MT1 G, JUNB, SOCS1 or CASP5; or wherein said one or more biomarkers comprise the genes or proteins listed in Tables 1 and 2; and c) determining if the level is changed in the patient sample compared to the level in a control untreated sample;

wherein a decreased level indicates patient compliance with said drug treatment protocol.

In one embodiment, in any one of the methods above, the level of the one or more biomarkers in the second biological sample is decreased by at least about 20%, 25%, 30%, 35%, 40%, 45%, 50%, 55%, 60%, 65%, 65%, 70%, 75%, 80%, 85%, 90%, or 95% or more as compared to the level in the first biological sample.

In one embodiment, in any one of the methods above, the biological sample is a skin biopsy, blood, plasma or serum sample. In one embodiment, in any one of the methods above, the anti-IL-36R antibody is spesolimab. In one embodiment, in any one of the methods above, the levels of biomarkers are determined by RNA sequencing or ELISA or another protein assay. In one embodiment, the biomarkers are the differentially expressed genes in skin.

In one embodiment, the present invention further provides a method of selecting a patient, for example using a method disclosed herein. In one embodiment, the present invention further provides a method of enriching a patient population for patients expected to have a beneficial response after treatment with an anti-IL-36R antibody, for example using a method of the present invention. In one embodiment, the present invention further provides a method of enriching a patient population for patients expected to have a beneficial response prior to or early after treatment with an anti-IL-36R antibody, for example using a method of the present invention.

In one embodiment, in any one of the methods above, the anti-IL-36R antibody or an antigen binding fragment thereof as disclosed below.

In one embodiment, the anti-IL-36R antibody or antigen-binding fragment thereof comprises a) a light chain variable region comprising the amino acid sequence of SEQ ID NO: 26 (L-CDR1); the amino acid sequence of SEQ ID NO: 35, 102, 103, 104, 105 106 or 140 (L-CDR2); the amino acid sequence of SEQ ID NO: 44 (L-CDR3); and b) a heavy chain variable region comprising the amino acid sequence of SEQ ID NO: 53 (H-CDR1); the amino acid sequence of SEQ ID NO: 62, 108, 109, 110 or 111 (H-CDR2); the amino acid sequence of SEQ ID NO: 72 (H-CDR3).

In one embodiment, the anti-IL-36R antibody or antigen-binding fragment thereof comprises:

I. a) a light chain variable region comprising the amino acid sequence of SEQ ID NO: 26 (L-CDR1); the amino acid sequence of SEQ ID NO: 102 (L-CDR2); the amino acid sequence of SEQ ID NO: 44 (L-CDR3); and b) a heavy chain variable region comprising the amino acid sequence of SEQ ID NO: 53 (H-CDR1); the amino acid sequence of SEQ ID NO: 62, 108, 109, 110 or 111 (H-CDR2); the amino acid sequence of SEQ ID NO: 72 (H-CDR3).

II. a) a light chain variable region comprising the amino acid sequence of SEQ ID NO: 26 (L-CDR1); the amino acid sequence of SEQ ID NO: 103 (L-CDR2); the amino acid sequence of SEQ ID NO: 44 (L-CDR3); and b) a heavy chain variable region comprising the amino acid sequence of SEQ ID NO: 53 (H-CDR1); the amino acid sequence of SEQ ID NO: 62, 108, 109, 110 or 111 (H-CDR2); the amino acid sequence of SEQ ID NO: 72 (H-CDR3).

III. a) a light chain variable region comprising the amino acid sequence of SEQ ID NO: 26 (L-CDR1); the amino acid sequence of SEQ ID NO: 104 (L-CDR2); the amino acid sequence of SEQ ID NO: 44 (L-CDR3); and b) a heavy chain variable region comprising the amino acid sequence of SEQ ID NO: 53 (H-CDR1); the amino acid sequence of SEQ ID NO: 62, 108, 109, 110 or 111 (H-CDR2); the amino acid sequence of SEQ ID NO: 72 (H-CDR3).

IV. a) a light chain variable region comprising the amino acid sequence of SEQ ID NO: 26 (L-CDR1); the amino acid sequence of SEQ ID NO: 105 (L-CDR2); the amino acid sequence of SEQ ID NO: 44 (L-CDR3); and b) a heavy chain variable region comprising the amino acid sequence of SEQ ID NO: 53 (H-CDR1); the amino acid sequence of SEQ ID NO: 62, 108, 109, 110 or 111 (H-CDR2); the amino acid sequence of SEQ ID NO: 72 (H-CDR3).

V. a) a light chain variable region comprising the amino acid sequence of SEQ ID NO: 26 (L-CDR1); the amino acid sequence of SEQ ID NO: 106 (L-CDR2); the amino acid sequence of SEQ ID NO: 44 (L-CDR3); and b) a heavy chain variable region comprising the amino acid sequence of SEQ ID NO: 53 (H-CDR1); the amino acid sequence of SEQ ID NO: 62, 108, 109, 110 or 111 (H-CDR2); the amino acid sequence of SEQ ID NO: 72 (H-CDR3).

VI. a) a light chain variable region comprising the amino acid sequence of SEQ ID NO: 26 (L-CDR1); the amino acid sequence of SEQ ID NO: 140 (L-CDR2); the amino acid sequence of SEQ ID NO: 44 (L-CDR3); and b) a heavy chain variable region comprising the amino acid sequence of SEQ ID NO: 53 (H-CDR1); the amino acid sequence of SEQ ID NO: 62, 108, 109, 110 or 111 (H-CDR2); the amino acid sequence of SEQ ID NO: 72 (H-CDR3).

In one embodiment, the anti-IL-36R antibody or antigen-binding fragment thereof comprises:

(i) a light chain variable region comprising the amino acid sequence of SEQ ID NO: 77; and a heavy chain variable region comprising the amino acid sequence of SEQ ID 5 NO: 87; or (ii) a light chain variable region comprising the amino acid sequence of SEQ ID NO: 77; and a heavy chain variable region comprising the amino acid sequence of SEQ ID NO: 88; or (iii) a light chain variable region comprising the amino acid sequence of SEQ ID NO: 77; and a heavy chain variable region comprising the amino acid sequence of SEQ ID NO: 89; or (iv) a light chain variable region comprising the amino acid sequence of SEQ ID NO: 80; and a heavy chain variable region comprising the amino acid sequence of SEQ ID NO: 87; or (v) a light chain variable region comprising the amino acid sequence of SEQ ID NO: 80; and a heavy chain variable region comprising the amino acid sequence of SEQ ID NO: 88; or (vi) a light chain variable region comprising the amino acid sequence of SEQ ID NO: 80; and a heavy chain variable region comprising the amino acid sequence of SEQ ID NO: 89; or (vii) a light chain variable region comprising the amino acid sequence of SEQ ID NO: 85; and a heavy chain variable region comprising the amino acid sequence of SEQ ID NO: 100; or (viii) a light chain variable region comprising the amino acid sequence of SEQ ID NO: 85; and a heavy chain variable region comprising the amino acid sequence of SEQ ID NO:101; or (ix) a light chain variable region comprising the amino acid sequence of SEQ ID NO: 86; and a heavy chain variable region comprising the amino acid sequence of SEQ ID NO: 100; or (x) a light chain variable region comprising the amino acid sequence of SEQ ID NO: 86; and a heavy chain variable region comprising the amino acid sequence of SEQ ID NO:101.

In one embodiment, the anti-IL-36R antibody or antigen-binding fragment thereof comprises:

i. a light chain comprising the amino acid sequence of SEQ ID NO: 115; and a heavy chain comprising the amino acid sequence of SEQ ID NO: 125; or ii. a light chain comprising the amino acid sequence of SEQ ID NO: 115; and a heavy chain comprising the amino acid sequence of SEQ ID NO: 126; or iii. a light chain comprising the amino acid sequence of SEQ ID NO: 115; and a heavy chain comprising the amino acid sequence of SEQ ID NO: 127; or iv. a light chain comprising the amino acid sequence of SEQ ID NO: 118; and a heavy chain comprising the amino acid sequence of SEQ ID NO: 125; or v. a light chain comprising the amino acid sequence of SEQ ID NO: 118; and a heavy chain comprising the amino acid sequence of SEQ ID NO: 126; or vi. a light chain comprising the amino acid sequence of SEQ ID NO: 118; and a heavy chain comprising the amino acid sequence of SEQ ID NO: 127; or vii. a light chain comprising the amino acid sequence of SEQ ID NO: 123; and a heavy chain comprising the amino acid sequence of SEQ ID NO: 138; or viii. a light chain comprising the amino acid sequence of SEQ ID NO: 123; and a heavy chain comprising the amino acid sequence of SEQ ID NO: 139; or ix. a light chain comprising the amino acid sequence of SEQ ID NO: 124; and a heavy chain comprising the amino acid sequence of SEQ ID NO: 138.

In one embodiment, the anti-IL-36R antibody is speso-limab, Antibody B1, Antibody B2, Antibody B3, Antibody B4, Antibody B5, Antibody B6, Antibody C1, Antibody C2, or Antibody C3.

In one embodiment, the anti-IL-36R antibody is an antibody as disclosed in WO2013/074569, WO2016/168542 or WO2020/018503, the content of each of which is incorporated herein by reference.

In one embodiment, the ELISA or other protein assay kit further comprises instructions for use of the kit prior to treatment or for monitoring GPP.

In another embodiment, the present invention relates to a composition comprising a biological sample from a patient with GPP and an agent for detecting absence or presence or level of one or more biomarkers comprise the genes or proteins listed in Tables 1 and 2. In a related embodiment, the agent is, for example, an antibody against any of the biomarkers listed in Table 1 and 2.

In one embodiment, in any one of the methods above, the anti-IL-36R antibody or an antigen binding fragment thereof as disclosed below.

In one aspect, the anti-IL-36R antibody is a humanized antibody. In one aspect, the anti-IL-36R antibody is a monoclonal antibody. In one aspect, the anti-IL-36R antibody is a full length antibody. In one aspect, the anti-IL-36R antibody is a humanized monoclonal antibody, for example a full length humanized monoclonal antibody. In one aspect, the anti-IL-36R antibody is spesolimab. Representative anti-IL36R antibodies are disclosed in in WO2013/074569, WO2016/168542 or WO2020/018503, the entire content of each of which is incorporated herein by reference.

IL-36R is also known as IL-1RL2 and IL-1Rrp2. It has been reported that agonistic IL-36 ligands ($\alpha$, $\beta$, or $\gamma$) initiate the signaling cascade by engaging the IL-36 receptor which then forms a heterodimer with the IL-1 receptor accessory protein (IL-1 RAcP). IL-36 antagonist ligands (IL-36RA/IL1F5, IL-38/ILF10) inhibit the signaling cascade.

Variable regions and CDRs of representative anti-IL-36R antibodies are disclosed below:

Anti-IL-36R Mouse Antibody Sequences

Variable regions and CDRs of representative mouse lead antibodies of the present invention (mouse leads) are shown below:

```
Light Chain Variable Region
(VK) Amino Acid Sequences
>33D10B12vK Protein (antibody 33D10)
                        (SEQ ID NO: 1)
QIVLTQSPAIMSASLGERVTMTCTASSSVSSSYLHW

YQKKPGSSPKLWVYSTSNLASGVPVRFSGSGSGTSY

SLTISSMEAEDAATYYCHQHHRSPVTFGSGTKLEMK

>172C8B12 vK protein (antibody 172C8)
                        (SEQ ID NO: 2)
DIQMTQSPASQSASLGESVTFTCLASQTIGTWLAWY

QQRPGKSPQLLIYAATSLADGVPSRFSGSGSGTQFS

FNIRSLQAEDFASYYCQQVYTTPLTFGGGTKLEIK

>67E7E8 vK protein (antibody 67E7)
                        (SEQ ID NO: 3)
DIQMTQSPASQSASLGESVTFTCLASQTIGTWLGW

YQQKPGKSPQLLIYRSTTLADGVPSRFSGSGSGTK

FSFKISSLQAADFASYYCQQLYSAPYTFGGGTKLE
```

-continued

IR

>78C8D1 vK Protein (antibody 78C8)
                              (SEQ ID NO: 4)
DVLLTQTPLSLPVSLGDQASISCRSSQNIVHSGN

TYLQWYLQKPGQSPKLLIYKVSNRFSGVPDRFSGS

GSGTDFTLKISRVEAEDLGVYYCFQGSHVPFTFGA

GTKLELK

>81A1D1 vK Protein (antibody 81A1)
                              (SEQ ID NO: 5)
DIQMTQTTSSLSASLGDRVTISCRASQDIYKYLNW

YQQKPDGTLKLLIYYTSGLHSGVPSRFSGSGSGTD

FSLTISNLEPEDIATYFCQQDSKFPWTFGGDTKLE

IK

>81B4E11 vK Protein (antibody 81B4)
                              (SEQ ID NO: 6)
QIVLTQSPAIMSASLGERVTMTCTASSSVSSSYFH

WYQQKPGSSPKLWIYRTSNLASGVPGRFSGSGSGT

SYSLTISSMEAEDAATYYCHQFHRSPLTFGAGTKL

ELK

>73C5C10 vK protein (antibody 73C5)
                              (SEQ ID NO: 7)
DIVMTQSQKFLSTSVGVRVSVTCKASQDVGTNVLW

YQQKIGQSPKPLIYSASYRHSGVPDRFTGSGSGTD

FTLIISNVQSEDLAEYFCQQYSRYPLTFGPGTKLE

LK

>73F6F8 vK protein (antibody 73F6)
                              (SEQ ID NO: 8)
DIVMTQSQKFLSTSVGVRVSVTCKASQDVGTNVLW

YQQKIGQSPKALIYSASYRHSGVPDRFTGSGSGTD

FTLIITNVQSEDLAEYFCQQYSRYPLTFGPGTKLE

LK

>76E10E8 vK protein (antibody 76E10)
                              (SEQ ID NO: 9)
DIVMTQSQKFMSATVGGRVNITCKASQNVGRAVAW

YQQKPGQSPKLLTHSASNRYTGVPDRFTGSGSGTD

FTLTITNMQSEDLADYFCQQYSSYPLTFGAGTKLD

LK

>89A12B8 vK protein (antibody 89A12)
                              (SEQ ID NO: 10)
DIQMTQSPASQSASLGESVTFSCLASQTIGTWLGW

YQQKPGKSPQLLIYRATSLADGVPSRFSGSGSGTN

FSFKISSLQAEDLASYYCQQLYSGPYTFGGGTKLE

IR

Heavy Chain Variable Region (VH)
Amino Acid Sequences
>33D10B12vH Protein (antibody 33D10)
                              (SEQ ID NO: 11)
QVQLQQSGTELLKPGASVKLSCKASGNTVTSYWM

HWVKQRPGQGLEWIGEILPSTGRTNYNENFKGKA

-continued

MLTVDKSSSTAYMQLSSLASEDSAVYYCTIVYFG

NPWFAYWGQGTLVTVSA

>172C8B12 vH protein (antibody 172C8)
                              (SEQ ID NO: 12)
EVQLQQSGPELVKPGASVKLSCKASGYTFTDNYMN

WVRQSHGKSLEWIGRVNPSNGDTKYNQNFKGKATL

TVDKSLSTAYMQLNGLTSEDSAVYYCGRTKNFYSS

YSYDDAMDYWGQGTSVTVSS

>67E7E8 vH protein (antibody 67E7)
                              (SEQ ID NO: 13)
EVQLQQSGAEFVRPGASVKFSCTASGFNIKDDYIH

WVRQRPEQGLEWVGRIDPANGNTKYAPKFQDKATI

TADTSSNTAYLQLSSLTSEDTAVYYCAKSFPNNYY

SYDDAFAYWGQGTLVTVSA

>78C8D1 vH Protein (antibody 78C8)
                              (SEQ ID NO: 14)
QVQLKESGPVLVAPSQSLSITCTVSGFSLTKFGVH

WIRQTPGKGLEWLGVIWAGGPTNYNSALMSRLTIS

KDISQSQVFLRIDSLQTDDTAMYYCAKQIYYSTLV

DYWGQGTSVTVSS

>81A1D1 vH Protein (antibody 81A1)
                              (SEQ ID NO: 15)
QVQLKESGPGLVAPSQSLFITCTVSGFSLSSYEIN

WVRQVPGKGLEWLGVIWTGITTNYNSALISRLSIS

KDNSKSLVFLKMNSLQTDDTAIYYCARGTGTGFYY

AMDYWGQGTSVTVSS

>81B4E11 vH Protein (antibody 81B4)
                              (SEQ ID NO: 16)
QVQLQQPGADFVRPGASMRLSCKASGYSFTSSWIH

WVKQRPGQGLEWIGEINPGNVRTNYNENFRNKATL

TVDKSSTTAYMQLRSLTSADSAVYYCTVVFYGEPY

FPYWGQGTLVTVSA

>73C5C10 vH Protein (antibody 73C5)
                              (SEQ ID NO: 17)
QVQLKESGPGLVAPSQSLSITCTVSGFSLTNYAVH

WVRQFPGKGLEWLGVIWSDGSTDFNAPFKSRLSIN

KDNSKSQVFFKMNSLQIDDTAIYYCARKGGYSGSW

FAYWGQGTLVTVSA

>73F6F8 vH protein (antibody 73F6)
                              (SEQ ID NO: 18)
QVQLKESGPGLVAPSQSLSITCTVSGFSLTNYAVH

WVRQFPGKGLEWLGVIWSDGSTDYNAPFKSRLSIN

KDNSKSQVFFKMNSLQTDDTAIYYCARKGGYSGSW

FAYWGQGTLVTVSA

>76E10E8 vH protein (antibody 76E10)
                              (SEQ ID NO: 19)
QVQLKESGPVLVAPSQSLSITCTVSGFSLTNYGVH

WVRQPPGKGLEWLGVIWPVGSTNYNSALMSRLSIH

-continued

KDNSKSQVFLRMNSLQTDDTAIYYCAKMDWDDFFD

YWGQGTTLTVSS

>89A12B8 vH Protein (antibody 89A12)
```
                                      (SEQ ID NO: 20)
EVQLQQSGAELVRPGASVRLSCTASGFNIKDDYIH

WVRQRPKQGLEWLGRIDPANGNTKYDPRFQDKATI

TADTSSNTAYLHLSSLTSEDTAVYYCAKSFPDNYY

SYDDAFAYWGQGTLVTVSA
```

Light chain CDR-1 (L-CDR1) Amino
Acid Sequences
>33D10G1 L-CDR1
```
                                      (SEQ ID NO: 21)
TASSSVSSSYLH
```

>172C8B12 L-CDR1
```
                                      (SEQ ID NO: 22)
LASQTIGTWLA
```

>67E7E8 L-CDR1
```
                                      (SEQ ID NO: 23)
LASQTIGTWLG
```

>78C8D1 L-CDR1
```
                                      (SEQ ID NO: 24)
RSSQNIVHSNGNTYLQ
```

>81A1D1 L-CDR1
```
                                      (SEQ ID NO: 25)
RASQDIYKYLN
```

>81B4E11 L-CDR1
```
                                      (SEQ ID NO: 26)
TASSSVSSSYFH
```

>73C5C10 L-CDR1
```
                                      (SEQ ID NO: 27)
KASQDVGTNVL
```

>73F6F8 L-CDR1
```
                                      (SEQ ID NO: 27)
KASQDVGTNVL
```

>76E10E8 L-CDR1
```
                                      (SEQ ID NO: 28)
KASQNVGRAVA
```

>89A12B8 L-CDR1
```
                                      (SEQ ID NO: 29)
LASQTIGTWLG
```

Light chain CDR-2 (L-CDR2)
Amino Acid Sequences
>33D10B12 L-CDR2
```
                                      (SEQ ID NO: 30)
STSNLAS
```

>172C8B12 L-CDR2
```
                                      (SEQ ID NO: 31)
AATSLAD
```

>67E7E8 L-CDR2
```
                                      (SEQ ID NO: 32)
RSTTLAD
```

>78C8D1 L-CDR2
```
                                      (SEQ ID NO: 33)
KVSNRFS
```

>81A1D1 L-CDR2
```
                                      (SEQ ID NO: 34)
YTSGLHS
```

>81 B4E11 L-CDR2
```
                                      (SEQ ID NO: 35)
RTSNLAS
```

-continued

>73C5C10 L-CDR2
```
                                      (SEQ ID NO: 36)
SASYRHS
```

>73F6F8 L-CDR2
```
                                      (SEQ ID NO: 36)
SASYRHS
```

>76E10E8 L-CDR2
```
                                      (SEQ ID NO: 37)
SASNRYT
```

>89A12B8 L-CDR2
```
                                      (SEQ ID NO: 38)
RATSLAD
```

Light chain CDR-3 (L-CDR3)
Amino Acid Sequences
>33D10B12 L-CDR3
```
                                      (SEQ ID NO: 39)
HQHHRSPVT
```

>172C8B12 L-CDR3
```
                                      (SEQ ID NO: 40)
QQVYTTPLT
```

>67E7E8 L-CDR3
```
                                      (SEQ ID NO: 41)
QQLYSAPYT
```

>78C8D1 L-CDR3
```
                                      (SEQ ID NO: 42)
FQGSHVPFT
```

>81A1D1 L-CDR3
```
                                      (SEQ ID NO: 43)
QQDSKFPWT
```

>81B4E11 L-CDR3
```
                                      (SEQ ID NO: 44)
HQFHRSPLT
```

>73C5C10 L-CDR3
```
                                      (SEQ ID NO: 45)
QQYSRYPLT
```

>73F6F8 L-CDR3
```
                                      (SEQ ID NO: 45)
QQYSRYPLT
```

>76E10E8 L-CDR3
```
                                      (SEQ ID NO: 46)
QQYSSYPLT
```

>89A12B8 L-CDR3
```
                                      (SEQ ID NO: 47)
QQLYSGPYT
```

Heavy chain CDR-1 (H-CDR1)
Amino Acid Sequences
>33D10B12 H-CDR1
```
                                      (SEQ ID NO: 48)
GNTVTSYWMH
```

>172C8B12 H-CDR1
```
                                      (SEQ ID NO: 49)
GYTFTDNYMN
```

>67E7E8 H-CDR1
```
                                      (SEQ ID NO: 50)
GFNIKDDYIH
```

>78C8D1 H-CDR1
```
                                      (SEQ ID NO: 51)
GFSLTKFGVH
```

>81A1D1 H-CDR1
```
                                      (SEQ ID NO: 52)
GFSLSSYEIN
```

-continued

```
>81B4E11 H-CDR1
                                    (SEQ ID NO: 53)
GYSFTSSWIH

>73C5C10 H-CDR1
                                    (SEQ ID NO: 54)
GFSLTNYAVH

>73F6F8 H-CDR1
                                    (SEQ ID NO: 54)
GFSLTNYAVH

>76E10E8 H-CDR1
                                    (SEQ ID NO: 55)
GFSLTNYGVH

>89A12B8 H-CDR1
                                    (SEQ ID NO: 56)
GFNIKDDYIH

Heavy chain CDR-2 (H-CDR2)
Amino Acid Sequences
>33D10B12 H-CDR2
                                    (SEQ ID NO: 57)
EILPSTGRTNYNENFKG >172C8B12 H-CDR2
                                    (SEQ ID NO: 58)
RVNPSNGDTKYNQNFKG >67E7E8 H-CDR2
                                    (SEQ ID NO: 59)
RIDPANGNTKYAPKFQD >78C8D1 H-CDR2
                                    (SEQ ID NO: 60)
VIWAGGPTNYNSALMS >81A1D1 H-CDR2
                                    (SEQ ID NO: 61)
VIWTGITTNYNSALIS >81B4E11 H-CDR2
                                    (SEQ ID NO: 62)
EINPGNVRTNYNENF >73C5C10 H-CDR2
                                    (SEQ ID NO: 63)
VIWSDGSTDFNAPFKS >73F6F8 H-CDR2
                                    (SEQ ID NO: 64)
VIWSDGSTDYNAPFKS >76E10E8 H-CDR2
                                    (SEQ ID NO: 65)
VIWPVGSTNYNSALMS >89A12B8 H-CDR2
                                    (SEQ ID NO: 66)
RIDPANGNTKYDPRFQD Heavy chain CDR-3 (H-CDR3)
Amino Acid Sequences
>33D10B12 H-CDR3
                                    (SEQ ID NO: 67)
VYFGNPWFAY >172C8B12 H-CDR3
                                    (SEQ ID NO: 68)
TKNFYSSYSYDDAMDY >67E7E8 H-CDR3
                                    (SEQ ID NO: 69)
SFPNNYYSYDDAFAY

>78C8D1 H-CDR3
                                    (SEQ ID NO: 70)
QIYYSTLVDY

>81A1D1 H-CDR3
```

-continued

```
                                    (SEQ ID NO: 71)
GTGTGFYYAMDY

>81B4E11 H-CDR3
                                    (SEQ ID NO: 72)
VFYGEPYFPY

>73C5C10 H-CDR3
                                    (SEQ ID NO: 73)
KGGYSGSWFAY

>73F6F8 H-CDR3
                                    (SEQ ID NO: 73)
KGGYSGSWFAY

>76E10E8 H-CDR3
                                    (SEQ ID NO: 74)
MDWDDFFDY

>89A12B8 H-CDR3
                                    (SEQ ID NO: 75)
SFPDNYYSYDDAFAY
```

Anti-IL-36R Mouse CDR Sequences

A Summary of the CDR Sequences of the Lead Mouse Antibodies is Shown Below:

| Antibody | H-CDR Sequences | L-CDR Sequences |
|---|---|---|
| 33D10 | GNTVTSYWMH (H-CDR1) SEQ ID No: 48 EILPSTGRTNYNENFKG (H-CDR2) SEQ ID No: 57 VYFGNPWFAY (H-CDR3) SEQ ID No: 67 | TASSSVSSSYLH (L-CDR1) SEQ ID No: 21 STSNLAS (L-CDR2) SEQ ID No: 30 HQHHRSPVT (L-CDR3) SEQ ID No: 39 |
| 172C8 | GYTFTDNYMN (H-CDR1) SEQ ID No: 49 RVNPSNGDTKYNQNFKG (H-CDR2) SEQ ID No: 58 TKNFYSSYSYDDAMDY (H-CDR3) SEQ ID No: 68 | LASQTIGTWLA (L-CDR1) SEQ ID No: 22 AATSLAD (L-CDR2) SEQ ID No: 31 QQVYTTPLT (L-CDR3) SEQ ID No: 40 |
| 67E7 | GFNIKDDYIH (H-CDR1) SEQ ID No: 50 RIDPANGNTKYAPKFQD (H-CDR2) SEQ ID No: 59 SFPNNYYSYDDAFAY (H-CDR3) SEQ ID No: 69 | LASQTIGTWLG (L-CDR1) SEQ ID No: 23 RSTTLAD (L-CDR2) SEQ ID No: 32 QQLYSAPYT (L-CDR3) SEQ ID No: 41 |
| 78C8 | GFSLTKFGVH (H-CDR1) SEQ ID No: 51 VIWAGGPTNYNSALMS (H-CDR2) SEQ ID No: 60 QIYYSTLVDY (H-CDR3) SEQ ID No: 70 | RSSQNIVHSNGNTYLQ (L-CDR1) SEQ ID No: 24 KVSNRFS (L-CDR2) SEQ ID No: 33 FQGSHVPFT (L-CDR3) SEQ ID No: 42 |
| 81A1 | GFSLSSYEIN (H-CDR1) SEQ ID No: 52 VIWTGITTNYNSALIS (H-CDR2) SEQ ID No: 61 GTGTGFYYAMDY (H-CDR3) SEQ ID No: 71 | RASQDIYKYLN (L-CDR1) SEQ ID No: 25 YTSGLHS (L-CDR2) SEQ ID No: 34 QQDSKFPWT (L-CDR3) SEQ ID No: 43 |
| 81B4 | GYSFTSSWIH (H-CDR1) SEQ ID No: 53 EINPGNVRTNYNENF (H-CDR2) SEQ ID No: 62 VFYGEPYFPY (H-CDR3) SEQ ID No: 72 | TASSSVSSSYFH (L-CDR1) SEQ ID No: 26 RTSNLAS (L-CDR2) SEQ ID No: 35 HQFHRSPLT (L-CDR3) SEQ ID No: 44 |

-continued

| Antibody | H-CDR Sequences | L-CDR Sequences |
|---|---|---|
| 73C5 | GFSLTNYAVH (H-CDR1) SEQ ID No: 54 VIWSDGSTDFNAPFKS (H-CDR2) SEQ ID No: 63 KGGYSGSWFAY (H-CDR3) SEQ ID No: 73 | KASQDVGTNVL (L-CDR1) SEQ ID No: 27 SASYRHS (L-CDR2) SEQ ID No: 36 QQYSRYPLT (L-CDR3) SEQ ID No: 45 |
| 73F6 | GFSLTNYAVH (H-CDR1) SEQ ID No: 54 VIWSDGSTDYNAPFKS (H-CDR2) SEQ ID No: 64 KGGYSGSWFAY (H-CDR3) SEQ ID No: 73 | KASQDVGTNVL (L-CDR1) SEQ ID No:27 SASYRHS (L-CDR2) SEQ ID No: 36 QQYSRYPLT (L-CDR3) SEQ ID No: 45 |
| 76E10 | GFSLTNYGVH (H-CDR1) SEQ ID No: 55 VIWPVGSTNYNSALMS (H-CDR2) SEQ ID No: 65 MDWDDFFDY (H-CDR3) SEQ ID No: 74 | KASQNVGRAVA (L-CDR1) SEQ ID No: 28 SASNRYT (L-CDR2) SEQ ID No: 37 QQYSSYPLT (L-CDR3) SEQ ID No: 46 |
| 89A12 | GFNIKDDYIH (H-CDR1) SEQ ID No: 56 RIDPANGNTKYDPRFQD (H-CDR2) SEQ ID No: 66 SFPDNYYSYDDAFAY (H-CDR3) SEQ ID No: 75 | LASQTIGTWLG (L-CDR1) SEQ ID No: 29 RATSLAD (L-CDR2) SEQ ID No: 38 QQLYSGPYT (L-CDR3) SEQ ID No: 47 |

Anti-IL-36R Humanized Antibody Sequences

Human framework sequences were selected for the mouse leads based on the framework homology, CDR structure, conserved canonical residues, conserved interface packing residues and other parameters to produce humanized variable regions (see Example 5).

Representative humanized variable regions derived from antibodies 81B4 and 7305 are shown below.

```
Light Chain Variable Region (VK)
Amino Acid Sequences
>81B4vK32_3 vK protein
                              (SEQ ID NO: 76)
EIVLTQSPGTLSLSPGERATMSCTASSSVSSSYFHWYQQK

PGQAPRLLIYRTSTLASGIPDRFSGSGSGTDFTLTISRLE

PEDAATYYCHQFHRSPLTFGQGTKLEIK

>81B4vK32_105 vK protein
                              (SEQ ID NO: 77)
EIVLTQSPGTLSLSPGERATMSCTASSSVSSSYFHWYQQK

PGQAPRLLIYRTSILASGVPDRFSGSGSGTDFTLTISRLE

PEDFATYYCHQFHRSPLTFGQGTKLEIK

>81B4vK32_116 vK protein
                              (SEQ ID NO: 78)
EIVLTQSPGTLSLSPGERATMSCTASSSVSSSYFHWYQQK

PGQAPRLWIYRTSRLASGVPDRFSGSGSGTDFTLTISRLE

PEDAATYYCHQFHRSPLTFGQGTKLEIK

>81B4vK32 127 vK protein
                              (SEQ ID NO: 79)
EIVLTQSPGTLSLSPGERATMTCTASSSVSSSYFHWYQQK

PGQAPRLLIYRTSRLASGVPDRFSGSGSGTDFTLTISRLE
```

-continued

```
PEDFAVYYCHQFHRSPLTFGQGTKLEIK

>81B4vK32_138 vK protein
                              (SEQ ID NO: 80)
QIVLTQSPGTLSLSPGERATMTCTASSSVSSSYFHWYQQK

PGQAPRLWIYRTSRLASGVPDRFSGSGSGTDFTLTISRLE

PEDAATYYCHQFHRSPLTFGAGTKLEIK

>81B4vK32_140 vK protein
                              (SEQ ID NO: 81)
QIVLTQSPGTLSLSPGERVTMSCTASSSVSSSYFHWYQQK

PGQAPRLLIYRTSQLASGIPDRFSGSGSGTDFTLTISRLE

PEDAATYYCHQFHRSPLTFGQGTKLEIK

>81B4vK32_141 vK protein
                              (SEQ ID NO: 82)
QIVLTQSPGTLSLSPGERATMTCTASSSVSSSYFHWYQQK

PGQAPRLLIYRTSKLASGVPDRFSGSGSGTDFTLTISRLE

PEDFATYYCHQFHRSPLTFGQGTKLEIK

>81B4vK32_147 vK protein
                              (SEQ ID NO: 83)
EIVLTQSPGTLSLSPGERATMSCTASSSVSSSYFHWYQQK

PGQAPRLLIYRTSHLASGIPGRFSGSGSGTDFTLTISRLE

PEDAAVYYCHQFHRSPLTFGQGTKLEIK

>73C5vK39_2 vK protein
                              (SEQ ID NO: 84)
EIVMTQSPATLSVSPGVRATLSCKASQDVGTNVLWYQQKP

GQAPRPLIYSASYRHSGIPDRFSGSGSGTEFTLTISSLQS

EDFAEYFCQQYSRYPLTFGQGTKLEIK

>73C5vK39_7 vK protein
                              (SEQ ID NO: 85)
EIVMTQSPATLSVSPGVRATLSCKASQDVGTNVLWYQQKP

GQAPRPLIYSASYRHSGIPDRFSGSGSGTEFTLTISSLQS

EDFAVYYCQQYSRYPLTFGQGTKLEIK

>73C5vK39_15 vK protein
                              (SEQ ID NO: 86)
EIVMTQSPATLSVSPGVRATLSCKASQDVGTNVLWYQQKP

GQAPRPLIYSASYRHSGIPARFSGSGSGTEFTLTISSLQS

EDFAEYYCQQYSRYPLTFGQGTKLEIK

Heavy Chain Variable Region
(VH) Amino Acid Sequences
>81B4vH33_49 vH Protein
                              (SEQ ID NO: 87)
QVQLVQSGAEVKKPGASVKVSCKASGYSFTSSWIHWVRQA

PGQGLEWIGEINPGNVRTNYNENFRNKATMTVDTSISTAY

MELSRLRSDDTAVYYCAVVFYGEPYFPYWGQGTLVTVSS

>81B4vH33_85T vH Protein
                              (SEQ ID NO: 88)
QVQLVQSGAEVKKPGASVKVSCKASGYSFTSSWIHWVRQR

PGQGLEWIGEINPGNVRTNYNENFRNRVTMTVDTSISTAY

MELSRLRSDDTAVYYCTVVFYGEPYFPYWGQGTLV5TVSS

>81B4vH33_90 vH Protein
                              (SEQ ID NO: 89)
QVQLVQSGAEVKKPGASVKVSCKASGYSFTSSWIHWVKQA
```

-continued

PGQGLEWMGEINPGNVRTNYNENFRNKVTMTVDTSISTAY

MELSRLRSDDTAVYYCTVVFYGEPYFPYWGQGTLVTVSS

>81B4vH33_93 vH Protein (SEQ ID NO: 90)

QVQLVQSGAEVKKPGASVKVSCKASGYSFTSSWIHWVRQR

PGQGLEWMGEINPGNVRTNYNENFRNRATLTRDTSISTAY

MELSRLRSDDTAVYYCAVVFYGEPYFPYWGQGTLVTVSS

>81B4vH50_22 vH Protein (SEQ ID NO: 91)

QVQLVQSGAEVKKPGASVKVSCKASGYSFTSSWIHWVRQR

PGQGLEWMGEILPGVVRTNYNENFRNKVTMTVDTSISTAY

MELSRLRSDDTAVYYCTVVFYGEPYFPYWGQGTLVTVSS

>81B4vH50_30 vH Protein (SEQ ID NO: 92)

QVQLVQSGAEVKKPGASVKVSCKASGYSFTSSWIHWVRQR

PGQGLEWIGEINPGAVRTNYNENFRNRVTMTVDTSISTAY

MELSRLRSDDTAVYYCTVVFYGEPYFPYWGQGTLVTVSS

>81B4vH51_13 vH Protein (SEQ ID NO: 93)

QVQLVQSGAEVKKPGASVKVSCKASGYSFTSSWIHWVRQA

PGQGLEWIGEINPGLVRTNYNENFRNKVTMTVDTSISTAY

MELSRLRSDDTAVYYCAVVFYGEPYFPYWGQGTLVTVSS

>81B4vH51_15 vH Protein (SEQ ID NO: 94)

QVQLVQSGAEVKKPGASVKVSCKASGYSFTSSWIHWVRQA

PGQGLEWIGEINPGAVRTNYNENFRNKVTMTVDTSISTAY

MELSRLRSDDTAVYYCAVVFYGEPYFPYWGQGTLVTVSS

>81B4vH52_83 vH Protein (SEQ ID NO: 95)

QVQLVQSGAEVKKPGASVKVSCKASGYSFTSSWIHWVRQA

PGQGLEWIGEINPGSVRTNYNENFRNKATMTVDTSISTAY

MELSRLRSDDTAVYYCAVVFYGEPYFPYWGQGTLV
TVSS

>73C5vH46_4 vH Protein 1

(SEQ ID NO: 96)

QVQLQESGPGLVKPSETLSITCTVSGFSLTDYAVHWIRQP

PGKGLEWIGVIWSDGSTDYNAPFKSRVTINKDTSKSQVSF

KMSSVQAADTAVYYCARKGGYSGSWFAYWGQGTLVTVSS

>73C5vH46_19 vH Protein (SEQ ID NO: 97)

QVQLQESGPGLVKPSETLSITCTVSGFSLTDYAVHWIRQP

PGKGLEWIGVIWSDGSTDYNAPFKSRVTISKDTSKNQVSL

KMNSLTTDDTAVYYCARKGGYSGSWFAYWGQGTLVTVSS

>73C5vH46_40 vH Protein (SEQ ID NO: 98)

QVQLQESGPGLVKPSETLSITCTVSGFSLTDYAVHWIRQP

PGKGLEWIGVIWSDGSTDYNAPFKSRVTISKDNSKSQVSL

KMNSVTVADTAVYYCARKGGYSGSWFAYWGQGTLVTVSS

>73C5vH47_65 vH Protein (SEQ ID NO: 99)

QVQLQESGPGLVKPSETLSITCTVSGFSLTDYAVHWVRQP

-continued

PGKGLEWIGVIWSDGSTDYNAPFKSRVTISKDTSKNQVSF

KLSSVTVDDTAVYYCARKGGYSGSWFAYWGQGTLVTVSS

>73C5vH47_77 vH Protein (SEQ ID NO: 100)

QVQLQESGPGLVAPSETLSLTCTVSGFSLTDYAVHWIRQF

PGKGLEWIGVIWSDGSTDFNAPFKSRVTISKDTSKNQVSF

KLSSVTTDDTAVYYCARKGGYSGSWFAYWGQGTLVTVSS

>73C5vH58_91 vH Protein (SEQ ID NO: 101)

QVQLQESGPGLVKPSETLSITCTVSGFSLTDYAVHWIRQ

PPGKGLEWIGVIWSDGSTDYNAPFKSRVTISKDNSKSQV

SFKMSSVTADDTAVYYCARKGGYSGSWFAYWGQGTLVTV

SS

The CDR sequences from the humanized variable regions derived from antibodies 81_B4 and 73C5 shown above are depicted below.

L-CDR1 Amino Acid Sequences

>81B4vK32_3 L-CDR1

(SEQ ID NO: 26)

TASSSVSSSYFH

>81B4vK32_105 L-CDR1

(SEQ ID NO: 26)

TASSSVSSSYFH

>81B4vK32_116 L-CDR1

(SEQ ID NO: 26)

TASSSVSSSYFH

>81B4vK32_127 L-CDR1

(SEQ ID NO: 26)

TASSSVSSSYFH

>81B4vK32_138 L-CDR1

(SEQ ID NO: 26)

TASSSVSSSYFH

>81B4vK32_140 L-CDR1

(SEQ ID NO: 26)

TASSSVSSSYFH

>81B4vK32_141 L-CDR1

(SEQ ID NO: 26)

TASSSVSSSYFH

>81B4vK32_147 L-CDR1

(SEQ ID NO: 26)

TASSSVSSSYFH

>73C5vK39_2 L-CDR1

(SEQ ID NO: 27)

KASQDVGTNVL

>73C5vK39_7 L-CDR1

(SEQ ID NO: 27)

KASQDVGTNVL

>73C5vK39_15 L-CDR1

(SEQ ID NO: 27)

KASQDVGTNVL

L-CDR2 Amino Acid Sequences

>81B4vK32_3 L-CDR2

(SEQ ID 102)

RTSTLAS

>81B4vK32_105 L-CDR2

(SEQ ID 103)

RTSILAS

```
>81B4vK32_116 L-CDR2
                                    (SEQ ID 104)
RTSRLAS

>81B4vK32_127 L-CDR2
                                    (SEQ ID 104)
RTSRLAS

>81B4vK32_138 L-CDR2
                                    (SEQ ID 104)
RTSRLAS

>81B4vK32_140 L-CDR2
                                    (SEQ ID 105)
RTSQLAS

>81B4vK32_141 L-CDR2
                                    (SEQ ID 106)
RTSKLAS

>81B4vK32_147 L-CDR2
                                    (SEQ ID 140)
RTSHLAS

>73C5vK39_2 L-CDR2
                                  (SEQ ID NO: 36)
SASYRHS

>73C5vK39_7 L-CDR2
                                  (SEQ ID NO: 36)
SASYRHS

>73C5vK39_15 L-CDR2
                                  (SEQ ID NO: 36)
SASYRHS

L-CDR3 Amino Acid Sequences
>81B4vK32_3 L-CDR3
                                  (SEQ ID NO: 44)
HQFHRSPLT >81B4vK32_105 L-CDR3
                                  (SEQ ID NO: 44)
HQFHRSPLT >81B4vK32_116 L-CDR3
                                  (SEQ ID NO: 44)
HQFHRSPLT >81B4vK32_127 L-CDR3
                                  (SEQ ID NO: 44)
HQFHRSPLT >81B4vK32_138 L-CDR3
                                  (SEQ ID NO: 44)
HQFHRSPLT >81B4vK32_140 L-CDR3
                                  (SEQ ID NO: 44)
HQFHRSPLT >81B4vK32_141 L-CDR3
                                  (SEQ ID NO: 44)
HQFHRSPLT >81B4vK32_147 L-CDR3
                                  (SEQ ID NO: 44)
HQFHRSPLT >73C5vK39_2 L-CDR3
                                  (SEQ ID NO: 45)
QQYSRYPLT >73C5vK39_7 L-CDR3
                                  (SEQ ID NO: 45)
QQYSRYPLT >73C5vK39_15 L-CDR3
                                  (SEQ ID NO: 45)
QQYSRYPLT
```

```
H-CDR1 Amino Acid Sequences
>81B4vH33_49 H-CDR1
                                (SEQ ID NO: 53)
GYSFTSSWIH >81B4vH33_85T H-CDR1
                                (SEQ ID NO: 53)
GYSFTSSWIH >81B4vH33_90 H-CDR1
                                (SEQ ID NO: 53)
GYSFTSSWIH >81B4vH33_93 H-CDR1
                                (SEQ ID NO: 53)
GYSFTSSWIH >81B4vH50_22 H-CDR1
(SEQ ID NO: 53)
GYSFTSSWIH >81B4vH50_30 H-CDR1
                                (SEQ ID NO: 53)
GYSFTSSWIH >81B4vH51_13 H-CDR1
                                (SEQ ID NO: 53)
GYSFTSSWIH >81B4vH51_15 H-CDR1
                                (SEQ ID NO: 53)
GYSFTSSWIH >81B4vH52_83 H-CDR1
                                (SEQ ID NO: 53)
GYSFTSSWIH >73C5vH46_4 H-CDR1
                               (SEQ ID NO: 107)
GFSLTDYAVH >73C5vH46_19 H-CDR1
                               (SEQ ID NO: 107)
GFSLTDYAVH >73C5vH46_40 H-CDR1
                               (SEQ ID NO: 107)
GFSLTDYAVH >73C5vH47_65 H-CDR1
                               (SEQ ID NO: 107)
GFSLTDYAVH >73C5vH47_77 H-CDR1
                               (SEQ ID NO: 107)
GFSLTDYAVH >73C5vH58_91 H-CDR1
                               (SEQ ID NO: 107)
GFSLTDYAVH H-CDR2 Amino Acid Sequences
>81B4vH33_49 H-CDR2
                                (SEQ ID NO: 62)
EINPGNVRTNYNENF >81B4vH33_85T H-CDR2
                                (SEQ ID NO: 62)
EINPGNVRTNYNENF >81B4vH33_90 H-CDR2
                                (SEQ ID NO: 62)
EINPGNVRTNYNENF >81B4vH33_93 H-CDR2
                                (SEQ ID NO: 62)
EINPGNVRTNYNENF >81B4vH50_22 H-CDR2
                               (SEQ ID NO: 108)
```

-continued

EILPGVVRTNYNENF

>81B4vH50_30 H-CDR2
(SEQ ID NO: 109)
EINPGAVRTNYNENF

>81B4vH51_13 H-CDR2
(SEQ ID NO: 110)
EINPGLVRTNYNENF

>81B4vH51_15 H-CDR2
(SEQ ID NO: 109)
EINPGAVRTNYNENF

>81B4vH52_83 H-CDR2
(SEQ ID NO: 111)
EINPGSVRTNYNENF

>73C5vH46_4 H-CDR2
(SEQ ID NO: 64)
VIWSDGSTDYNAPFKS

>73C5vH46_19 H-CDR2
(SEQ ID NO: 64)
VIWSDGSTDYNAPFKS

>73C5vH46_40 H-CDR2
(SEQ ID NO: 64)
VIWSDGSTDYNAPFKS

>73C5vH47_65 H-CDR2
(SEQ ID NO: 64)
VIWSDGSTDYNAPFKS

>73C5vH47_77 H-CDR2
(SEQ ID NO: 63)
VIWSDGSTDFNAPFKS

>73C5vH58_91 H-CDR2
(SEQ ID NO: 64)
VIWSDGSTDYNAPFKS

H-CDR3 Amino Acid Sequences
>81B4vH33_49 H-CDR3
(SEQ ID NO: 72)
VFYGEPYFPY

>81B4vH33_85T H-CDR3
(SEQ ID NO: 72)
VFYGEPYFPY

>81B4vH33_90 H-CDR3
(SEQ ID NO: 72)
VFYGEPYFPY

>81B4vH33_93 H-CDR3
(SEQ ID NO: 72)
VFYGEPYFPY

>81B4vH50_22 H-CDR3
(SEQ ID NO: 72)
VFYGEPYFPY

>81B4vH50_30 H-CDR3
(SEQ ID NO: 72)
VFYGEPYFPY

>81B4vH51_13 H-CDR3
(SEQ ID NO: 72)
VFYGEPYFPY

>81B4vH51_15 H-CDR3
(SEQ ID NO: 72)
VFYGEPYFPY

>81B4vH52_83 H-CDR3
(SEQ ID NO: 72)
VFYGEPYFPY

>73C5vH46_4 H-CDR3
(SEQ ID NO: 73)

-continued

KGGYSGSWFAY

>73C5vH46_19 H-CDR3
(SEQ ID NO: 73)
KGGYSGSWFAY

>73C5vH46_40 H-CDR3
(SEQ ID NO: 73)
KGGYSGSWFAY

>73C5vH47_65 H-CDR3
(SEQ ID NO: 73)
KGGYSGSWFAY

>73C5vH47_77 H-CDR3
(SEQ ID NO: 73)
KGGYSGSWFAY

>73C5vH58_91 H-CDR3
(SEQ ID NO: 73)
KGGYSGSWFAY
Heavy Chain Constant region linked
downstream of a humanized variable
heavy
(SEQ ID NO: 112)
ASTKGPSVFPLAPSSKSTSGGTAALGCLVKDYFPEPVTVS

WNSGALTSGVHTFPAVLQSSGLYSLSSVVTVPSSSLGTQT

YICNVNHKPSNTKVDKRVEPKSCDKTHTCPPCPAPEAAGG

PSVFLFPPKPKDTLMISRTPEVTCVVVDVSHEDPEVKFNW

YVDGVEVHNAKTKPREEQYNSTYRVVSVLTVLHQDWLNGK

EYKCKVSNKALPAPIEKTISKAKGQPREPQVYTLPPSREE

MTKNQVSLTCLVKGFYPSDIAVEWESNGQPENNYKTTPPV

LDSDGSFFLYSKLTVDKSRWQQGNVFSCSVMHEALHNHYT

QKSLSLSPGK

Light Chain Constant region linked
downstream of a humanized variable
light region:
(SEQ ID NO: 113)
RTVAAPSVFIFPPSDEQLKSGTASVVCLLNNFYPREAKV

QWKVDNALQSGNSQESVTEQDSKDSTYSLSSTLTLSKAD

YEKHKVYACEVTHQGLSSPVTKSFNRGEC

Representative light chain and heavy chain sequences of the present invention are shown below (humanized variable regions derived from antibodies 81B4 and 73C5 linked to constant regions).

Light Chain Amino Acid Sequences
>81B4vK32_3 Light Chain
(SEQ ID NO: 114)
EIVLTQSPGTLSLSPGERATMSCTASSSVSSSYFHWYQQK

PGQAPRLLIYRTSTLASGIPDRFSGSGSGTDFTLTISRLE

PEDAATYYCHQFHRSPLTFGQGTKLEIKRTVAAPSVFIFP

PSDEQLKSGTASVVCLLNNFYPREAKVQWKVDNALQSGNS

QESVTEQDSKDSTYSLSSTLTLSKADYEKHKVYACEVTHQ

GLSSPVTKSFNRGEC

>81B4vK32_105 Light Chain
(SEQ ID NO: 115)
EIVLTQSPGTLSLSPGERATMSCTASSSVSSSYFHWYQQK

PGQAPRLLIYRTSILASGVPDRFSGSGSGTDFTLTISRLE

-continued

PEDFATYYCHQFHRSPLTFGQGTKLEIKRTVAAPSVFIFP

PSDEQLKSGTASVVCLLNNFYPREAKVQWKVDNALQSGNS

QESVTEQDSKDSTYSLSSTLTLSKADYEKHKVYACEVTHQ

GLSSPVTKSFNRGEC

>81B4vK32_116 Light Chain (SEQ ID NO: 116)

EIVLTQSPGTLSLSPGERATMSCTASSSVSSSYFHWYQQK

PGQAPRLWIYRTSRLASGVPDRFSGSGSGTDFTLTISRLE

PEDAATYYCHQFHRSPLTFGQGTKLEIKRTVAAPSVFIFP

PSDEQLKSGTASVVCLLNNFYPREAKVQWKVDNALQSGNS

QESVTEQDSKDSTYSLSSTLTLSKADYEKHKVYACEVTHQ

GLSSPVTKSFNRGEC

>81B4vK32_127 Light Chain (SEQ ID NO: 117)

EIVLTQSPGTLSLSPGERATMTCTASSSVSSSYFHWYQQK

PGQAPRLLIYRTSRLASGVPDRFSGSGSGTDFTLTISRLE

PEDFAVYYCHQFHRSPLTFGQGTKLEIKRTVAAPSVFIFP

PSDEQLKSGTASVVCLLNNFYPREAKVQWKVDNALQSGNS

QESVTEQDSKDSTYSLSSTLTLSKADYEKHKVYACEVTHQ

GLSSPVTKSFNRGEC

>81B4vK32_138 Light Chain (SEQ ID NO: 118)

QIVLTQSPGTLSLSPGERATMTCTASSSVSSSYFHWYQQK

PGQAPRLWIYRTSRLASGVPDRFSGSGSGTDFTLTISRLE

PEDAATYYCHQFHRSPLTFGAGTKLEIKRTVAAPSVFIFP

PSDEQLKSGTASVVCLLNNFYPREAKVQWKVDNALQSGNS

QESVTEQDSKDSTYSLSSTLTLSKADYEKHKVYACEVTHQ

GLSSPVTKSFNRGEC

>81B4vK32_140 Light Chain (SEQ ID NO: 119)

QIVLTQSPGTLSLSPGERVTMSCTASSSVSSSYFHWYQQK

PGQAPRLLIYRTSQLASGIPDRFSGSGSGTDFTLTISRLE

PEDAATYYCHQFHRSPLTFGQGTKLEIKRTVAAPSVFIFP

PSDEQLKSGTASVVCLLNNFYPREAKVQWKVDNALQSGNS

QESVTEQDSKDSTYSLSSTLTLSKADYEKHKVYACEVTHQ

GLSSPVTKSFNRGEC

>81B4vK32_141 Light Chain (SEQ ID NO: 120)

QIVLTQSPGTLSLSPGERATMTCTASSSVSSSYFHWYQQK

PGQAPRLLIYRTSKLASGVPDRFSGSGSGTDFTLTISRLE

PEDFATYYCHQFHRSPLTFGQGTKLEIKRTVAAPSVFIFP

PSDEQLKSGTASVVCLLNNFYPREAKVQWKVDNALQSGNS

QESVTEQDSKDSTYSLSSTLTLSKADYEKHKVYACEVTHQ

GLSSPVTKSFNRGEC

>81B4yK32_147 Light Chain (SEQ ID NO: 121)

EIVLTQSPGTLSLSPGERATMSCTASSSVSSSYFHWYQQK

-continued

PGQAPRLLIYRTSHLASGIPGRFSGSGSGTDFTLTISRLE

PEDAAVYYCHQFHRSPLTFGQGTKLEIKRTVAAPSVFIFP

PSDEQLKSGTASVVCLLNNFYPREAKVQWKVDNALQSGNS

QESVTEQDSKDSTYSLSSTLTLSKADYEKHKVYACEVTHQ

GLSSPVTKSFNRGEC

>73C5vK39_2 Light Chain (SEQ ID NO: 122)

EIVMTQSPATLSVSPGVRATLSCKASQDVGTNVLWYQQKP

GQAPRPLIYSASYRHSGIPDRFSGSGSGTEFTLTISSLQS

EDFAEYFCQQYSRYPLTFGQGTKLEIKRTVAAPSVFIFPP

SDEQLKSGTASVVCLLNNFYPREAKVQWKVDNALQSGNSQ

ESVTEQDSKDSTYSLSSTLTLSKADYEKHKVYACEVTHQG

LSSPVTKSFNRGEC

>73C5vK39_7 Light Chain (SEQ ID NO: 123)

EIVMTQSPATLSVSPGVRATLSCKASQDVGTNVLWYQQKP

GQAPRPLIYSASYRHSGIPDRFSGSGSGTEFTLTISSLQS

EDFAVYYCQQYSRYPLTFGQGTKLEIKRTVAAPSVFIFPP

SDEQLKSGTASVVCLLNNFYPREAKVQWKVDNALQSGNSQ

ESVTEQDSKDSTYSLSSTLTLSKADYEKHKVYACEVTHQG

LSSPVTKSFNRGEC

>73C5vK39_15 Light Chain (SEQ ID NO: 124)

EIVMTQSPATLSVSPGVRATLSCKASQDVGTNVLWYQQKP

GQAPRPLIYSASYRHSGIPARFSGSGSGTEFTLTISSLQS

EDFAEYYCQQYSRYPLTFGQGTKLEIKRTVAAPSVFIFPP

SDEQLKSGTASVVCLLNNFYPREAKVQWKVDNALQSGNSQ

ESVTEQDSKDSTYSLSSTLTLSKADYEKHKVYACEVTHQG

LSSPVTKSFNRGEC

Heavy Chain Amino Acid Sequences

>81B4vH33_49 Heavy Chain (SEQ ID NO: 125)

QVQLVQSGAEVKKPGASVKVSCKASGYSFTSSWIHWVRQA

PGQGLEWIGEINPGNVRTNYNENFRNKATMTVDTSISTAY

MELSRLRSDDTAVYYCAVVFYGEPYFPYWGQGTLVTVSSA

STKGPSVFPLAPSSKSTSGGTAALGCLVKDYFPEPVTVSW

NSGALTSGVHTFPAVLQSSGLYSLSSVVTVPSSSLGTQTY

ICNVNHKPSNTKVDKRVEPKSCDKTHTCPPCPAPEAAGGP

SVFLFPPKPKDTLMISRTPEVTCVVVDVSHEDPEVKFNWY

VDGVEVHNAKTKPREEQYNSTYRVVSVLTVLHQDWLNGKE

YKCKVSNKALPAPIEKTISKAKGQPREPQVYTLPPSREEM

TKNQVSLTCLVKGFYPSDIAVEWESNGQPENNYKTTPPVL

DSDGSFFLYSKLTVDKSRWQQGNVFSCSVMHEALHNHYTQ

KSLSLSPGK

-continued

>81B4vH33_85T Heavy Chain
(SEQ ID NO: 126)
QVQLVQSGAEVKKPGASVKVSCKASGYSFTSSWIHWVRQR

PGQGLEWIGEINPGNVRTNYNENFRNRVTMTVDTSISTAY

MELSRLRSDDTAVYYCTVVFYGEPYFPYWGQGTLVTVSSA

STKGPSVFPLAPSSKSTSGGTAALGCLVKDYFPEPVTVSW

NSGALTSGVHTFPAVLQSSGLYSLSSVVTVPSSSLGTQTY

ICNVNHKPSNTKVDKRVEPKSCDKTHTCPPCPAPEAAGGP

SVFLFPPKPKDTLMISRTPEVTCVVVDVSHEDPEVKFNWY

VDGVEVHNAKTKPREEQYNSTYRVVSVLTVLHQDWLNGKE

YKCKVSNKALPAPIEKTISKAKGQPREPQVYTLPPSREEM

TKNQVSLTCLVKGFYPSDIAVEWESNGQPENNYKTTPPVL

DSDGSFFLYSKLTVDKSRWQQGNVFSCSVMHEALHNHYTQ

KSLSLSPGK

>81B4vH33_90 Heavy Chain
(SEQ ID NO: 127)
QVQLVQSGAEVKKPGASVKVSCKASGYSFTSSWIHWVKQA

PGQGLEWMGEINPGNVRTNYNENFRNKVTMTVDTSISTAY

MELSRLRSDDTAVYYCTVVFYGEPYFPYWGQGTLVTVSSA

STKGPSVFPLAPSSKSTSGGTAALGCLVKDYFPEPVTVSW

NSGALTSGVHTFPAVLQSSGLYSLSSVVTVPSSSLGTQTY

ICNVNHKPSNTKVDKRVEPKSCDKTHTCPPCPAPEAAGGP

SVFLFPPKPKDTLMISRTPEVTCVVVDVSHEDPEVKFNWY

VDGVEVHNAKTKPREEQYNSTYRVVSVLTVLHQDWLNGKE

YKCKVSNKALPAPIEKTISKAKGQPREPQVYTLPPSREEM

TKNQVSLTCLVKGFYPSDIAVEWESNGQPENNYKTTPPVL

DSDGSFFLYSKLTVDKSRWQQGNVFSCSVMHEALHNHYTQ

KSLSLSPGK

>81B4vH33_93 Heavy Chain
(SEQ ID NO: 128)
QVQLVQSGAEVKKPGASVKVSCKASGYSFTSSWIHWVRQR

PGQGLEWMGEINPGNVRTNYNENFRNRATLTRDTSISTAY

MELSRLRSDDTAVYYCAVVFYGEPYFPYWGQGTLVTVSSA

STKGPSVFPLAPSSKSTSGGTAALGCLVKDYFPEPVTVSW

NSGALTSGVHTFPAVLQSSGLYSLSSVVTVPSSSLGTQTY

ICNVNHKPSNTKVDKRVEPKSCDKTHTCPPCPAPEAAGGP

SVFLFPPKPKDTLMISRTPEVTCVVVDVSHEDPEVKFNWY

VDGVEVHNAKTKPREEQYNSTYRVVSVLTVLHQDWLNGKE

YKCKVSNKALPAPIEKTISKAKGQPREPQVYTLPPSREEM

TKNQVSLTCLVKGFYPSDIAVEWESNGQPENNYKTTPPVL

DSDGSFFLYSKLTVDKSRWQQGNVFSCSVMHEALHNHYTQ

KSLSLSPGK

>81B4vH50_22 Heavy Chain
(SEQ ID NO: 129)

-continued
QVQLVQSGAEVKKPGASVKVSCKASGYSFTSSWIHWVRQR

PGQGLEWMGEILPGVVRTNYNENFRNKVTMTVDTSISTAY

MELSRLRSDDTAVYYCTVVFYGEPYFPYWGQGTLVTVSSA

STKGPSVFPLAPSSKSTSGGTAALGCLVKDYFPEPVTVSW

NSGALTSGVHTFPAVLQSSGLYSLSSVVTVPSSSLGTQTY

ICNVNHKPSNTKVDKRVEPKSCDKTHTCPPCPAPEAAGGP

SVFLFPPKPKDTLMISRTPEVTCVVVDVSHEDPEVKFNWY

VDGVEVHNAKTKPREEQYNSTYRVVSVLTVLHQDWLNGKE

YKCKVSNKALPAPIEKTISKAKGQPREPQVYTLPPSREEM

TKNQVSLTCLVKGFYPSDIAVEWESNGQPENNYKTTPPVL

DSDGSFFLYSKLTVDKSRWQQGNVFSCSVMHEALHNHYTQ

KSLSLSPGK

>81B4vH50_30 Heavy Chain
(SEQ ID NO: 130)
QVQLVQSGAEVKKPGASVKVSCKASGYSFTSSWIHWVRQR

PGQGLEWIGEINPGAVRTNYNENFRNRVTMTVDTSISTAY

MELSRLRSDDTAVYYCTVVFYGEPYFPYWGQGTLVTVSSA

STKGPSVFPLAPSSKSTSGGTAALGCLVKDYFPEPVTVSW

NSGALTSGVHTFPAVLQSSGLYSLSSVVTVPSSSLGTQTY

ICNVNHKPSNTKVDKRVEPKSCDKTHTCPPCPAPEAAGGP

SVFLFPPKPKDTLMISRTPEVTCVVVDVSHEDPEVKFNWY

VDGVEVHNAKTKPREEQYNSTYRVVSVLTVLHQDWLNGKE

YKCKVSNKALPAPIEKTISKAKGQPREPQVYTLPPSREEM

TKNQVSLTCLVKGFYPSDIAVEWESNGQPENNYKTTPPVL

DSDGSFFLYSKLTVDKSRWQQGNVFSCSVMHEALHNHYTQ

KSLSLSPGK

>81B4vH51_13 Heavy Chain
(SEQ ID NO: 131)
QVQLVQSGAEVKKPGASVKVSCKASGYSFTSSWIHWVRQA

PGQGLEWIGEINPGLVRTNYNENFRNKVTMTVDTSISTAY

MELSRLRSDDTAVYYCAVVFYGEPYFPYWGQGTLVTVSSA

STKGPSVFPLAPSSKSTSGGTAALGCLVKDYFPEPVTVSW

NSGALTSGVHTFPAVLQSSGLYSLSSVVTVPSSSLGTQTY

ICNVNHKPSNTKVDKRVEPKSCDKTHTCPPCPAPEAAGGP

SVFLFPPKPKDTLMISRTPEVTCVVVDVSHEDPEVKFNWY

VDGVEVHNAKTKPREEQYNSTYRVVSVLTVLHQDWLNGKE

YKCKVSNKALPAPIEKTISKAKGQPREPQVYTLPPSREEM

TKNQVSLTCLVKGFYPSDIAVEWESNGQPENNYKTTPPVL

DSDGSFFLYSKLTVDKSRWQQGNVFSCSVMHEALHNHYTQ

KSLSLSPGK

>81B4vH51_15 Heavy Chain
(SEQ ID NO: 132)
QVQLVQSGAEVKKPGASVKVSCKASGYSFTSSWIHWVRQA

PGQGLEWIGEINPGAVRTNYNENFRNKVTMTVDTSISTAY

-continued

MELSRLRSDDTAVYYCAVVFYGEPYFPYWGQGTLVTVSSA

STKGPSVFPLAPSSKSTSGGTAALGCLVKDYFPEPVTVSW

NSGALTSGVHTFPAVLQSSGLYSLSSVVTVPSSSLGTQTY

ICNVNHKPSNTKVDKRVEPKSCDKTHTCPPCPAPEAAGGP

SVFLFPPKPKDTLMISRTPEVTCVVVDVSHEDPEVKFNWY

VDGVEVHNAKTKPREEQYNSTYRVVSVLTVLHQDWLNGKE

YKCKVSNKALPAPIEKTISKAKGQPREPQVYTLPPSREEM

TKNQVSLTCLVKGFYPSDIAVEWESNGQPENNYKTTPPVL

DSDGSFFLYSKLTVDKSRWQQGNVFSCSVMHEALHNHYTQ

KSLSLSPGK

>81B4vH52_83 Heavy Chain
                                    (SEQ ID NO: 133)
QVQLVQSGAEVKKPGASVKVSCKASGYSFTSSWIHWVRQA

PGQGLEWIGEINPGSVRTNYNENFRNKATMTVDTSISTAY

MELSRLRSDDTAVYYCAVVFYGEPYFPYWGQGTLVTVSSA

STKGPSVFPLAPSSKSTSGGTAALGCLVKDYFPEPVTVSW

NSGALTSGVHTFPAVLQSSGLYSLSSVVTVPSSSLGTQTY

ICNVNHKPSNTKVDKRVEPKSCDKTHTCPPCPAPEAAGGP

SVFLFPPKPKDTLMISRTPEVTCVVVDVSHEDPEVKFNWY

VDGVEVHNAKTKPREEQYNSTYRVVSVLTVLHQDWLNGKE

YKCKVSNKALPAPIEKTISKAKGQPREPQVYTLPPSREEM

TKNQVSLTCLVKGFYPSDIAVEWESNGQPENNYKTTPPVL

DSDGSFFLYSKLTVDKSRWQQGNVFSCSVMHEALHNHYTQ

KSLSLSPGK

>73C5vH46_4 Heavy Chain
                                    (SEQ ID NO: 134)
QVQLQESGPGLVKPSETLSITCTVSGFSLTDYAVHWIRQP

PGKGLEWIGVIWSDGSTDYNAPFKSRVTINKDTSKSQVSF

KMSSVQAADTAVYYCARKGGYSGSWFAYWGQGTLVTVSSA

STKGPSVFPLAPSSKSTSGGTAALGCLVKDYFPEPVTVSW

NSGALTSGVHTFPAVLQSSGLYSLSSVVTVPSSSLGTQTY

ICNVNHKPSNTKVDKRVEPKSCDKTHTCPPCPAPEAAGGP

SVFLFPPKPKDTLMISRTPEVTCVVVDVSHEDPEVKFNWY

VDGVEVHNAKTKPREEQYNSTYRVVSVLTVLHQDWLNGKE

YKCKVSNKALPAPIEKTISKAKGQPREPQVYTLPPSREEM

TKNQVSLTCLVKGFYPSDIAVEWESNGQPENNYKTTPPVL

DSDGSFFLYSKLTVDKSRWQQGNVFSCSVMHEALHNHYTQ

KSLSLSPGK

>73C5vH46_19 Heavy Chain
                                    (SEQ ID NO: 135)
QVQLQESGPGLVKPSETLSITCTVSGFSLTDYAVHWIRQP

PGKGLEWIGVIWSDGSTDYNAPFKSRVTISKDTSKNQVSL

KMNSLTTDDTAVYYCARKGGYSGSWFAYWGQGTLVTVSSA

-continued

STKGPSVFPLAPSSKSTSGGTAALGCLVKDYFPEPVTVSW

NSGALTSGVHTFPAVLQSSGLYSLSSVVTVPSSSLGTQTY

ICNVNHKPSNTKVDKRVEPKSCDKTHTCPPCPAPEAAGGP

SVFLFPPKPKDTLMISRTPEVTCVVVDVSHEDPEVKFNWY

VDGVEVHNAKTKPREEQYNSTYRVVSVLTVLHQDWLNGKE

YKCKVSNKALPAPIEKTISKAKGQPREPQVYTLPPSREEM

TKNQVSLTCLVKGFYPSDIAVEWESNGQPENNYKTTPPVL

DSDGSFFLYSKLTVDKSRWQQGNVFSCSVMHEALHNHYTQ

KSLSLSPGK

>73C5vH46_40 Heavy Chain
                                    (SEQ ID NO: 136)
QVQLQESGPGLVKPSETLSITCTVSGFSLTDYAVHWIRQP

PGKGLEWIGVIWSDGSTDYNAPFKSRVTISKDNSKSQVSL

KMNSVTVADTAVYYCARKGGYSGSWFAYWGQGTLVTVSSA

STKGPSVFPLAPSSKSTSGGTAALGCLVKDYFPEPVTVSW

NSGALTSGVHTFPAVLQSSGLYSLSSVVTVPSSSLGTQTY

ICNVNHKPSNTKVDKRVEPKSCDKTHTCPPCPAPEAAGGP

SVFLFPPKPKDTLMISRTPEVTCVVVDVSHEDPEVKFNWY

VDGVEVHNAKTKPREEQYNSTYRVVSVLTVLHQDWLNGKE

YKCKVSNKALPAPIEKTISKAKGQPREPQVYTLPPSREEM

TKNQVSLTCLVKGFYPSDIAVEWESNGQPENNYKTTPPVL

DSDGSFFLYSKLTVDKSRWQQGNVFSCSVMHEALHNHYTQ

KSLSLSPGK

>73C5vH47_65 Heavy Chain
                                    (SEQ ID NO: 137)
QVQLQESGPGLVKPSETLSITCTVSGFSLTDYAVHWVRQP

PGKGLEWIGVIWSDGSTDYNAPFKSRVTISKDTSKNQVSF

KLSSVTVDDTAVYYCARKGGYSGSWFAYWGQGTLVTVSSA

STKGPSVFPLAPSSKSTSGGTAALGCLVKDYFPEPVTVSW

NSGALTSGVHTFPAVLQSSGLYSLSSVVTVPSSSLGTQTY

ICNVNHKPSNTKVDKRVEPKSCDKTHTCPPCPAPEAAGGP

SVFLFPPKPKDTLMISRTPEVTCVVVDVSHEDPEVKFNWY

VDGVEVHNAKTKPREEQYNSTYRVVSVLTVLHQDWLNGKE

YKCKVSNKALPAPIEKTISKAKGQPREPQVYTLPPSREEM

TKNQVSLTCLVKGFYPSDIAVEWESNGQPENNYKTTPPVL

DSDGSFFLYSKLTVDKSRWQQGNVFSCSVMHEALHNHYTQ

KSLSLSPGK

>73C5vH47_77 Heavy Chain
                                    (SEQ ID NO: 138)
QVQLQESGPGLVAPSETLSLTCTVSGFSLTDYAVHWIRQF

PGKGLEWIGVIWSDGSTDFNAPFKSRVTISKDTSKNQVSF

KLSSVTTDDTAVYYCARKGGYSGSWFAYWGQGTLVTVSSA

STKGPSVFPLAPSSKSTSGGTAALGCLVKDYFPEPVTVSW

NSGALTSGVHTFPAVLQSSGLYSLSSVVTVPSSSLGTQTY

-continued

```
ICNVNHKPSNTKVDKRVEPKSCDKTHTCPPCPAPEAAGGP

SVFLFPPKPKDTLMISRTPEVTCVVVDVSHEDPEVKFNWY

VDGVEVHNAKTKPREEQYNSTYRVVSVLTVLHQDWLNGKE

YKCKVSNKALPAPIEKTISKAKGQPREPQVYTLPPSREEM

TKNQVSLTCLVKGFYPSDIAVEWESNGQPENNYKTTPPVL

DSDGSFFLYSKLTVDKSRWQQGNVFSCSVMHEALHNHYTQ

KSLSLSPGK

>73C5vH58_91 Heavy Chain
                           (SEQ ID NO: 139)
QVQLQESGPGLVKPSETLSITCTVSGFSLTDYAVHWIRQP

PGKGLEWIGVIWSDGSTDYNAPFKSRVTISKDNSKSQVSF

KMSSVTADDTAVYYCARKGGYSGSWFAYWGQGTLVTVSSA

STKGPSVFPLAPSSKSTSGGTAALGCLVKDYFPEPVTVSW

NSGALTSGVHTFPAVLQSSGLYSLSSVVTVPSSSLGTQTY

ICNVNHKPSNTKVDKRVEPKSCDKTHTCPPCPAPEAAGGP

SVFLFPPKPKDTLMISRTPEVTCVVVDVSHEDPEVKFNWY

VDGVEVHNAKTKPREEQYNSTYRVVSVLTVLHQDWLNGKE

YKCKVSNKALPAPIEKTISKAKGQPREPQVYTLPPSREEM

TKNQVSLTCLVKGFYPSDIAVEWESNGQPENNYKTTPPVL

DSDGSFFLYSKLTVDKSRWQQGNVFSCSVMHEALHNHYTQ

KSLSLSPGK
```

The CDRs listed above are defined using the Chothia numbering system (AI-Lazikani et al., (1997) JMB 273, 927-948).

In one aspect, an antibody of the present invention comprises 3 light chain CDRs and 3 heavy chain CDRs, for example as set forth above.

In one aspect, an antibody of the present invention comprises a light chain and a heavy chain variable region as set forth above. In one aspect, a light chain variable region of the invention is fused to a light chain constant region, for example a kappa or lambda constant region. In one aspect, a heavy chain variable region of the invention is fused to a heavy chain constant region, for example IgA, IgD, IgE, IgG or IgM, in particular, $IgG_1$, $IgG_2$, $IgG_3$ or $IgG_4$.

The present invention provides an anti-IL-36R antibody comprising a light chain comprising the amino acid sequence of SEQ ID NO: 115; and a heavy chain comprising the amino acid sequence of SEQ ID NO: 125 (Antibody B1).

The present invention provides an anti-IL-36R antibody comprising a light chain comprising the amino acid sequence of SEQ ID NO: 115; and a heavy chain comprising the amino acid sequence of SEQ ID NO: 126 (Antibody B2).

The present invention provides an anti-IL-36R antibody comprising a light chain comprising the amino acid sequence of SEQ ID NO: 115; and a heavy chain comprising the amino acid sequence of SEQ ID NO: 127 (Antibody B3).

The present invention provides an anti-IL-36R antibody comprising a light chain comprising the amino acid sequence of SEQ ID NO: 118; and a heavy chain comprising the amino acid sequence of SEQ ID NO: 125 (Antibody B4).

The present invention provides an anti-IL-36R antibody comprising a light chain comprising the amino acid sequence of SEQ ID NO: 118; and a heavy chain comprising the amino acid sequence of SEQ ID NO: 126 (Antibody B5).

The present invention provides an anti-IL-36R antibody comprising a light chain comprising the amino acid sequence of SEQ ID NO: 118; and a heavy chain comprising the amino acid sequence of SEQ ID NO: 127 Antibody B6).

The present invention provides an anti-IL-36R antibody comprising a light chain comprising the amino acid sequence of SEQ ID NO: 123; and a heavy chain comprising the amino acid sequence of SEQ ID NO: 138 (Antibody C3).

The present invention provides an anti-IL-36R antibody comprising a light chain comprising the amino acid sequence of SEQ ID NO: 123; and a heavy chain comprising the amino acid sequence of SEQ ID NO: 139 (Antibody C2).

The present invention provides an anti-IL-36R antibody comprising a light chain comprising the amino acid sequence of SEQ ID NO: 124; and a heavy chain comprising the amino acid sequence of SEQ ID NO: 138 (Antibody C1)

Representative antibodies of the present invention are shown below.

TABLE B

| Antibody | Light Chain Sequences | Heavy Chain Sequences |
|---|---|---|
| B1 | EIVLTQSPGTLSLSP GERATMSCTASSSVS SSYFHWYQQKPGQAP RLLIYRTSILASGVP DRFSGSGSGTDFTLT ISRLEPEDFATYYCH QFHRSPLTFGQGTKL EIKRTVAAPSVFIFP PSDEQLKSGTASVVC LLNNFYPREAKVQWK VDNALQSGNSQESVT EQDSKDSTYSLSSTL TLSKADYEKHKVYAC EVTHQGLSSPVTKSF NRGEC (SEQ ID NO: 115) | QVQLVQSGAEVKKPG ASVKVSCKASGYSFT SSWIHWVRQAPGQGL EWIGEINPGNVRTNY NENFRNKATMTVDTS ISTAYMELSRLRSDD TAVYYCAVVFYGEPY FPYWGQGTLVTVSSA STKGPSVFPLAPSSK STSG GTAALGCLVKDYFPE PVTVSWNSGALTSGV HTFPAVLQSSGLYSL SSVVTVPSSSLGTQT YICNVNHKPSNTKVD KRVEPKSCDKTHTCP PCPAPEAAGGPSVFL FPPKPKDTLMISRTP EVTCVVVDVSHEDPE VKFNWYVDGVEVHNA KTKPREEQYNSTYRV VSVLTVLHQDWLNGK EYKCKVSNKALPAPI EKTISKAKGQPREPQ VYTLPPSREEMTKNQ VSLTCLVKGFYPSDI AVEWESNGQPENNYK TTPPVLDSDGSFFLY SKLTVDKSRWQQGNV FSCSVMHEALHNHYT QKSLSLSPGK (SEQ ID NO: 125) |
| B2 | EIVLTQSPGTLSLSP GERATMSCTASSSVS SSYFHWYQQKPGQAP RLLIYRTSILASGVP DRFSGSGSGTDFTLT ISRLEPEDFATYYCH QFHRSPLTFGQGTKL EIKRTVAAPSVFIFP PSDEQLKSGTASVVC LLNNFYPREAKVQWK VDNALQSGNSQESVT EQDSKDSTYSLSSTL TLSKADYEKHKVYAC EVTHQGLSSPVTKSF NRGEC (SEQ ID NO: 115) | QVQLVQSGAEVKKPG ASVKVSCKASGYSFT SSWIHWVRQRPGQGL EWIGEINPGNVRTNY NENFRNRVTMTVDTS ISTAYMELSRLRSDD TAVYYCTVVFYGEPY FPYWGQGTLVTVSSA STKGPSVFPLAPSSK STSGGTAALGCLVKD YFPEPVTVSWNSGAL TSGVHTFPAVLQSSG LYSLSSVVTVPSSSL GTQTYICNVNHKPSN TKVDKRVEPKSCDKT HTCPPCPAPEAAGGP SVFLFPPKPKDTLMI SRTPEVTCVVVDVSH |

<table>
<tr><td>37</td><td>38</td></tr>
</table>

37

TABLE B-continued

| Antibody | Light Chain Sequences | Heavy Chain Sequences |
|---|---|---|
| | | EDPEVKFNWYVDGVE VHNAKTKPREEQYNS TYRVVSVLTVLHQDW LNGKEYKCKVSNKAL PAPIEKTISKAKGQP REPQVYTLPPSREEM TKNQVSLTCLVKGFY PSDIAVEWESNGQPE NNYKTTPPVLDSDGS FFLYSKLTVDKSRWQ QGNVFSCSVMHEALH NHYTQKSLSLSPGK (SEQ ID NO: 126) |
| B3 | EIVLTQSPGTLSLSP GERATMSCTASSSVS SSYFHWYQQKPGQAP RLLIYRTSILASGVP DRFSGSGSGTDFTLT ISRLEPEDFATYYCH QFHRSPLTFGQGTKL EIKRTVAAPSVFIFP PSDEQLKSGTASVVC LLNNFYPREAKVQWK VDNALQSGNSQESVT EQDSKDSTYSLSSTL TLSKADYEKHKVYAC EVTHQGLSSPVTKSF NRGEC (SEQ ID NO: 115) | QVQLVQSGAEVKKPG ASVKVSCKASGYSFT SSWIHWVKQAPGQGL EWMGEINPGNVRTNY NENFRNKVTMTVDTS ISTAYMELSRLRSDD TAVYYCTVVFYGEPY FPYWGQGTLVTVSSA STKGPSVFPLAPSSK STSGGTAALGCLVKD YFPEPVTVSWNSGAL TSGVHTFPAVLQSSG LYSLSSVVTVPSSSL GTQTYICNVNHKPSN TKVDKRVEPKSCDKT HTCPPCPAPEAAGGP SVFLFPPKPKDTLMI SRTPEVTCVVVDVSH EDPEVKFNWYVDGVE VHNAKTKPREEQYNS TYRVVSVLTVLHQDW LNGKEYKCKVSNKAL PAPIEKTISKAKGQP REPQVYTLPPSREEM TKNQVSLTCLVKGFY PSDIAVEWESNGQPE NNYKTTPPVLDSDGS FFLYSKLTVDKSRWQ QGNVFSCSVMHEALH NHYTQKSLSLSPGK (SEQ ID NO: 127) |
| B4 | QIVLTQSPGTLSLSP GERATMTCTASSSVS SSYFHWYQQKPGQAP RLWIYRTSRLASGVP DRFSGSGSGTDFTLT ISRLEPEDAATYYCH QFHRSPLTFGAGTKL EIKRTVAAPSVFIFP PSDEQLKSGTASVVC LLNNFYPREAKVQWK VDNALQSGNSQESVT EQDSKDSTYSLSSTL TLSKADYEKHKVYAC EVTHQGLSSPVTKSF NRGEC (SEQ ID NO: 118) | QVQLVQSGAEVKKPG ASVKVSCKASGYSFT SSWIHWVRQAPGQGL EWIGEINPGNVRTNY NENFRNKATMTVDTS ISTAYMELSRLRSDD TAVYYCAVVFYGEPY FPYWGQGTLVTVSSA STKGPSVFPLAPSSK STSGGTAALGCLVKD YFPEPVTVSWNSGAL TSGVHTFPAVLQSSG LYSLSSVVTVPSSSL GTQTYICNVNHKPSN TKVDKRVEPKSCDKT HTCPPCPAPEAAGGP SVFLFPPKPKDTLMI SRTPEVTCVVVDVSH EDPEVKFNWYVDGVE VHNAKTKPREEQYNS TYRVVSVLTVLHQDW LNGKEYKCKVSNKAL PAPIEKTISKAKGQP REPQVYTLPPSREEM TKNQVSLTCLVKGFY PSDIAVEWESNGQPE NNYKTTPPVLDSDGS FFLYSKLTVDKSRWQ QGNVFSCSVMHEALH NHYTQKSLSLSPGK (SEQ ID NO: 125) |

38

TABLE B-continued

| Antibody | Light Chain Sequences | Heavy Chain Sequences |
|---|---|---|
| B5 | QIVLTQSPGTLSLSP GERATMTCTASSSVS SSYFHWYQQKPGQAP RLWIYRTSRLASGVP DRFSGSGSGTDFTLT ISRLEPEDAATYYCH QFHRSPLTFGAGTKL EIKRTVAAPSVFIFP PSDEQLKSGTASVVC LLNNFYPREAKVQWK VDNALQSGNSQESVT EQDSKDSTYSLSSTL TLSKADYEKHKVYAC EVTHQGLSSPVTKSF NRGEC (SEQ ID NO: 118) | QVQLVQSGAEVKKPG ASVKVSCKASGYSFT SSWIHWVRQRPGQGL EWIGEINPGNVRTNY NENFRNRVTMTVDTS ISTAYMELSRLRSDD TAVYYCTVVFYGEPY FPYWGQGTLVTVSSA STKGPSVFPLAPSSK STSGGTAALGCLVKD YFPEPVTVSWNSGAL TSGVHTFPAVLQSSG LYSLSSVVTVPSSSL GTQTYICNVNHKPSN TKVDKRVEPKSCDKT HTCPPCPAPEAAGGP SVFLFPPKPKDTLMI SRTPEVTCVVVDVSH EDPEVKFNWYVDGVE VHNAKTKPREEQYNS TYRVVSVLTVLHQDW LNGKEYKCKVSNKAL PAPIEKTISKAKGQP REPQVYTLPPSREEM TKNQVSLTCLVKGFY PSDIAVEWESNGQPE NNYKTTPPVLDSDGS FFLYSKLTVDKSRWQ QGNVFSCSVMHEALH NHYTQKSLSLSPGK (SEQ ID NO: 126) |
| B6 | QIVLTQSPGTLSLSP GERATMTCTASSSVS SSYFHWYQQKPGQAP RLWIYRTSRLASGVP DRFSGSGSGTDFTLT ISRLEPEDAATYYCH QFHRSPLTFGAGTKL EIKRTVAAPSVFIFP PSDEQLKSGTASVVC LLNNFYPREAKVQWK VDNALQSGNSQESVT EQDSKDSTYSLSSTL TLSKADYEKHKVYAC EVTHQGLSSPVTKSF NRGEC (SEQ ID NO: 118) | QVQLVQSGAEVKKPG ASVKVSCKASGYSFT SSWIHWVKQAPGQGL EWMGEINPGNVRTNY NENFRNKVTMTVDTS ISTAYMELSRLRSDD TAVYYCTVVFYGEPY FPYWGQGTLVTVSSA STKGPSVFPLAPSS KSTSG GTAALGCLVKDYFPE PVTVSWNSGALTSGV HTFPAVLQSSGLYSL SSVVTVPSSSLGTQT YICNVNHKPSNTKVD KRVEPKSCDKTHTCP PCPAPEAAGGPSVFL FPPKPKDTLMISRTP EVTCVVVDVSHEDPE VKFNWYVDGVEVHNA KTKPREEQYNSTYRV VSVLTVLHQDWLNGK EYKCKVSNKALPAPI EKTISKAKGQPREPQ VYTLPPSREEMTKNQ VSLTCLVKGFYPSDI AVEWESNGQPENNYK TTPPVLDSDGSFFLY SKLTVDKSRWQQGNV FSCSVMHEALHNHYT QKSLSLSPGK (SEQ ID NO: 127) |

TABLE C

| Antibody | Light Chain Sequences | Heavy Chain Sequences |
|---|---|---|
| C1 | EIVMTQSPATLSVSP GVRATLSCKASQDVG TNVLWYQQKPGQAPR | QVQLQESGPGLVAPS ETLSLTCTVSGFSLT DYAVHWIRQFPGKGL |

TABLE C-continued

| Antibody | Light Chain Sequences | Heavy Chain Sequences |
|---|---|---|
| | PLIYSASYRHSGIPA RFSGSGSGTEFTLTI SSLQSEDFAEYYCQQ YSRYPLTFGQGTKLE IKRTVAAPSVFIFPP SDEQLKSGTASVVCL LNNFYPREAKVQWKV DNALQSGNSQESVTE QDSKDSTYSLSSTLT LSKADYEKHKVYACE VTHQGLSSPVTKSFN RGEC (SEQ ID NO: 124) | EWIGVIWSDGSTDFN APFKSRVTISKDTSK NQVSFKLSSVTTDDT AVYYCARKGGYSGSW FAYWGQGTLVTVSSA STKGPSVFPLAPSSK STSGGTAALGCLVKD YFPEPVTVSWNSGAL TSGVHTFPAVLQSSG LYSLSSVVTVPSSSL GTQTYICNVNHKPSN TKVDKRVEPKSCDKT HTCPPCPAPEAAGGP SVFLFPPKPKDTLMI SRTPEVTCVVVDVSH EDPEVKFNWYVDGVE VHNAKTKPREEQYNS TYRVVSVLTVLHQDW LNGKEYKCKVSNKAL PAPIEKTISKAKGQP REPQVYTLPPSREEM TKNQVSLTCLVKGFY PSDIAVEWESNGQPE NNYKTTPPVLDSDGS FFLYSKLTVDKSRWQ QGNVFSCSVMHEALH NHYTQKSLSLSPGK (SEQ ID NO: 138) |
| C2 | EIVMTQSPATLSVSP GVRATLSCKASQDVG TNVLWYQQKPGQAPR PLIYSASYRHSGIPD RFSGSGSGTEFTLTI SSLQSEDFAVYYCQQ YSRYPLTFGQGTKLE IKRTVAAPSVFIFPP SDEQLKSGTASVVCL LNNFYPREAKVQWKV DNALQSGNSQESVTE QDSKDSTYSLSSTLT LSKADYEKHKVYACE VTHQGLSSPVTKSFN RGEC (SEQ ID NO: 123) | QVQLQESGPGLVKPS ETLSITCTVSGFSLT DYAVHWIRQPPGKGL EWIGVIWSDGSTDYN APFKSRVTISKDNSK SQVSFKMSSVTADDT AVYYCARKGGYSGSW FAYWGQGTLVTVSSA STKGPSVFPLAPSSK STSGGTAALGCLVKD YFPEPVTVSWNSGAL TSGVHTFPAVLQSSG LYSLSSVVTVPSSSL GTQTYICNVNHKPSN TKVDKRVEPKSCDKT HTCPPCPAPEAAGGP SVFLFPPKPKDTLMI SRTPEVTCVVVDVSH EDPEVKFNWYVDGVE VHNAKTKPREEQYNS TYRVVSVLTVLHQDW LNGKEYKCKVSNKAL PAPIEKTISKAKGQP REPQVYTLPPSREEM TKNQVSLTCLVKGFY PSDIAVEWESNGQPE NNYKTTPPVLDSDGS FFLYSKLTVDKSRWQ QGNVFSCSVMHEALH NHYTQKSLSLSPGK (SEQ ID NO: 139) |
| C3 | EIVMTQSPATLSVSP GVRATLSCKASQDVG TNVLWYQQKPGQAPR PLIYSASYRHSGIPD RFSGSGSGTEFTLTI SSLQSEDFAVYYCQQ YSRYPLTFGQGTKLE IKRTVAAPSVFIFPP SDEQLKSGTASVVCL LNNFYPREAKVQWKV DNALQSGNSQESVTE QDSKDSTYSLSSTLT LSKADYEKHKVYACE VTHQGLSSPVTKSFN RGEC (SEQ ID NO: 123) | QVQLQESGPGLVAPS ETLSLTCTVSGFSLT DYAVHWIRQFPGKGL EWIGVIWSDGSTDFN APFKSRVTISKDTSK NQVSFKLSSVTTDDT AVYYCARKGGYSGSW FAYWGQGTLVTVSSA STKGPSVFPLAPSSK STSGGTAALGCLVKD YFPEPVTVSWNSGAL TSGVHTFPAVLQSSG LYSLSSVVTVPSSSL GTQTYICNVNHKPSN TKVDKRVEPKSCDKT HTCPPCPAPEAAGGP |

TABLE C-continued

| Antibody | Light Chain Sequences | Heavy Chain Sequences |
|---|---|---|
| | | SVFLFPPKPKDTLMI SRTPEVTCVVVDVSH EDPEVKFNWYVDGVE VHNAKTKPREEQYNS TYRVVSVLTVLHQDW LNGKEYKCKVSNKAL PAPIEKTISKAKGQP REPQVYTLPPSREEM TKNQVSLTCLVKGFY PSDIAVEWESNGQPE NNYKTTPPVLDSDGS FFLYSKLTVDKSRWQ QGNVFSCSVMHEALH NHYTQKSLSLSPGK (SEQ ID NO: 138) |

The invention is further described in the following examples, which are not intended to limit the scope of the invention.

EXAMPLES

Example 1: Pustular Psoriasis: Molecular Pathways and Effects of Spesolimab in Generalized Pustular Psoriasis Abstract Background: The IL-36 pathway plays a key role in the pathogenesis of generalized pustular psoriasis (GPP). In a proof-of-concept clinical trial, treatment with spesolimab, an anti-IL-36 receptor antibody, resulted in rapid skin and pustular clearance in patients presenting with acute GPP flares.

Objective: To compare the molecular profiles of lesional and non-lesional skin from patients with GPP with skin from healthy volunteers, and to investigate the molecular changes after spesolimab treatment in the skin and blood of patients with acute GPP flares.

Methods: Pre- and post-treatment skin and blood samples were collected from patients with GPP who participated in a single-arm, Phase I study (n=7). Biomarkers were assessed by RNA sequencing, histopathology and immunohistochemistry.

Results: In GPP lesions, 1287 transcripts were commonly up- or downregulated. Selected transcripts from the IL-36 signalling pathway were upregulated in untreated GPP lesions. In patients with GPP, IL-36 pathway-related signatures, T helper (Th)1/Th17 and innate inflammation signalling, neutrophilic mediators and keratinocyte-driven inflammation pathways, were downregulated by spesolimab as early as Week 1. Spesolimab also decreased related serum biomarkers and cell populations in the skin lesions from patients with GPP, including CD3+T, CD11c+, IL-36γ+ cells and lipocalin-2-expressing cells.

Conclusion: In patients with GPP, spesolimab showed rapid modulation of commonly dysregulated molecular pathways in GPP, which may be associated with improved clinical outcomes. A single intravenous dose of spesolimab resulted in strong and rapid downregulation of biomarkers linked to key inflammatory processes, highlighting the relevance of anti-IL-36 receptor-targeted therapy for patients with GPP.

Capsule Summary

This is the first study to show that spesolimab, an anti-IL-36 receptor monoclonal antibody, can modulate differentially expressed genes in GPP lesions, including IL-36 pathway signatures, in patients with a GPP flare.

Abbreviations

DEG: differentially expressed gene
IHC: immunohistochemistry
GPP: generalized pustular psoriasis
PPP: palmoplantar pustulosis
RNA-seq: RNA sequencing Methods and Analysis Study Samples and Studies Skin biopsies of 3-4 mm punch were taken adjacent to pustules, and blood samples were collected from adult patients with GPP (limbs/torso, n=7) and healthy volunteers (limbs [arms/legs], n=10; palms/soles, n=6)(23, 25). In a Phase I, multicentre, single-arm, open-label, proof-of-concept study, patients with GPP received a single intravenous dose of 10 mg/kg spesolimab and were followed for 20 weeks (NCT02978690). Patients had a GPP flare involving ≥10% of their body surface area with erythema, including the presence of pustules, and a Generalized Pustular Psoriasis Physician Global Assessment (GPPGA) score of ≥3 (moderate-to-severe disease). Informed consent was obtained from all participants.

Tissue and Blood Sampling and Biomarker Analyses in Patients with GPP

Global transcriptome-wide RNA sequencing (RNA-seq; Illumina Hi-Seq 4000, Illumina, San Diego, CA) of lesional and non-lesional skin biopsy specimens and whole blood was used to characterise cellular and molecular response to spesolimab. Skin biopsies were performed at baseline (lesional and non-lesional skin) and at Week 1 (lesional skin), with an optional biopsy performed at Week 2 (lesional skin). Lesional skin biopsies were collected at the site of the most inflamed lesion, that is the deepest red erythema. RNA extraction from skin samples were performed with RNeasy Fibrous Tissue Mini Kit (Qiagen, Valencia, CA). Whole blood and serum were collected at multiple timepoints. RNA-seq was performed at baseline for both non-lesional and lesional skin types, at Weeks 1 and 2 for lesional skin, and at baseline and Weeks 1, 2 and 4 in whole blood samples. RNA extraction from blood samples was performed with the PAXgene® Blood mRNA Kit (Qiagen, Valencia, CA). Skin biopsies were evaluated for histopathology and immunohistochemistry (IHC) using specific antibodies, and evaluated with a semi-quantitative scoring method that has been previously published; with this method, each biopsy sample was given a global histopathological score. Biomarkers associated with GPP disease, including neutrophil elastase, lipocalin-2, IL-36γ, CD11c and CD3, were assessed in skin biopsies by IHC at baseline, Week 1 and Week 2 (optional). Serum samples were assayed for multiple biomarkers using the Randox Biochip Array platform at baseline and at Weeks 2, 4 and 12. The biomarkers assessed were β-defensin 4A, CCL20, CXCL1, IL-17A, IL-19, IL-1 RN, IL-6, IL-8 and C-reactive protein. The Ingenuity Pathway Analysis (IPA) library of canonical pathways was used to identify pathways that were most significant to the data set.

Statistical Analysis

Due to the small sample size, mainly descriptive analyses for continuous IHC biomarkers and serum biomarkers were conducted. For patients with GPP, the main focus was on changes over time, particularly for patients with elevated biomarker values at baseline.

Link to clinical endpoints were mainly assessed via graphical visualisations on an individual patient level (heat-maps). Since the various clinical endpoints and biomarkers are on different scales, these figures are presented on a relative scale via percentage change from baseline allowing for a meaningful comparison.

Exploratory analyses of over time changes in gene expression levels over time were performed to identify differentially expressed genes (DEGs). This analysis was conducted using the limma package. Briefly, only genes with counts per million 1 in at least half the samples in at least one subgroup were included in the analysis. Data were normalised using the TMM method described by Robinson and Oshlack and voom-transformed. To account for correlation between subjects, the duplicate Correlation function was used with subject as a blocking factor, a linear model was fit using the lmFit-function and, finally, moderated t-statistics were computed to derive log 2 fold change and corresponding Benjamini-Hochberg FDR-adjusted P-values.

Results

Baseline Comparison of the Molecular Profile in Skin from Patients with GPP and Healthy Volunteers Gene expression in biopsies of lesional skin compared with non-lesional skin from patients with GPP (limbs/torso) and these were also compared with healthy volunteer's samples (limbs or palms/soles). Clear distinct patterns of DEGs were observed between thin (limbs/torso) and thick (palms/soles) skin associated with GPP.

Using an absolute fold change of 2 and an adjusted P≤0.01 biopsies from patients with GPP had 7614 DEGs. Disease-relevant genes that were increased >5-fold in GPP lesional skin compared with healthy donors included S-100 (A7A, A7, A8, A9, A12), DEFB4A, VNN3, CCL18, IL19, IL20, IL22, IL17A, IL36G, IL36A, CXCL8, CXCL10, MMP12 and LCN2. Most DEGs in GPP lesional skin (>log 5-fold) were more highly expressed in lesional than non-lesional skin. Up-regulation of S100A8/9 and IL36A was measured in GPP. Increased expression of molecular pathways across GPP lesional skin included acute phase response signalling, IL-6, IL-8 and IL-23 signalling in addition to Th1, Th2 and dendritic cell signalling and keratinocyte-driven inflammation. Multiple consensus disease-relevant pathways are modulated across GPP, including IL-17/TNF-induced transcripts in keratinocytes and psoriatic pathways.

Modulation of Genes and Proteins in Patients with GPP after Treatment with Spesolimab At baseline, global transcriptome analysis identified 3276 DEGs between lesional and non-lesional skin, 1885 upregulated and 1391 downregulated transcripts (adjusted P≤0.05, fold change ≥2; FIG. 1A). Among those, all IL-36 ligands were strongly upregulated (IL36A: 90-fold; IL36B: 2.6-fold; IL36G: 13-fold).

The expression of 987 genes in lesional skin reached near non-lesional levels by Week 1 after a single infusion with spesolimab (adjusted P≤0.05, fold change ≥2) (FIG. 1A). DEGs were associated with innate (e.g. IL6, TNFα) and Th1/Th17-mediated inflammation (e.g. IL1B, IL12B, IL23A) and proinflammatory processes of keratinocyte activation (e.g. IL17C, IL24). Activation z-scores obtained for canonical pathways by Ingenuity Pathway Analysis (IPA) showed that the higher activity in lesional skin at baseline was downregulated by spesolimab by Week 1 (FIG. 1B). Significant decreases in pro-inflammatory mediators (TNF, IL1B, IL6), neutrophil recruitment mediators (CXCL1, CXCL2, CXCL3, CXCL5, CXCL6, CXCL8, CXCR1, CXCR1, CXCR2), neutrophil-expressed transcripts (NCF1, NCF2, NCF4, ELANE) or in keratinocyte activation, differentiation and mediated inflammation transcripts (IL36A, IL36G, IL17C, IL19, IL20, IL22, IL24) were found in lesional skin after 1 week of spesolimab treatment (FIG. 1C). Strong inhibition of T-cell activity was observed after spesolimab treatment, including T helper (Th)1/Th2 pathways and CD28 signalling in Th cells (FIG. 1B), and this was associated with the downregulation of elevated IL17C (FIG. C).

Figure 2A:
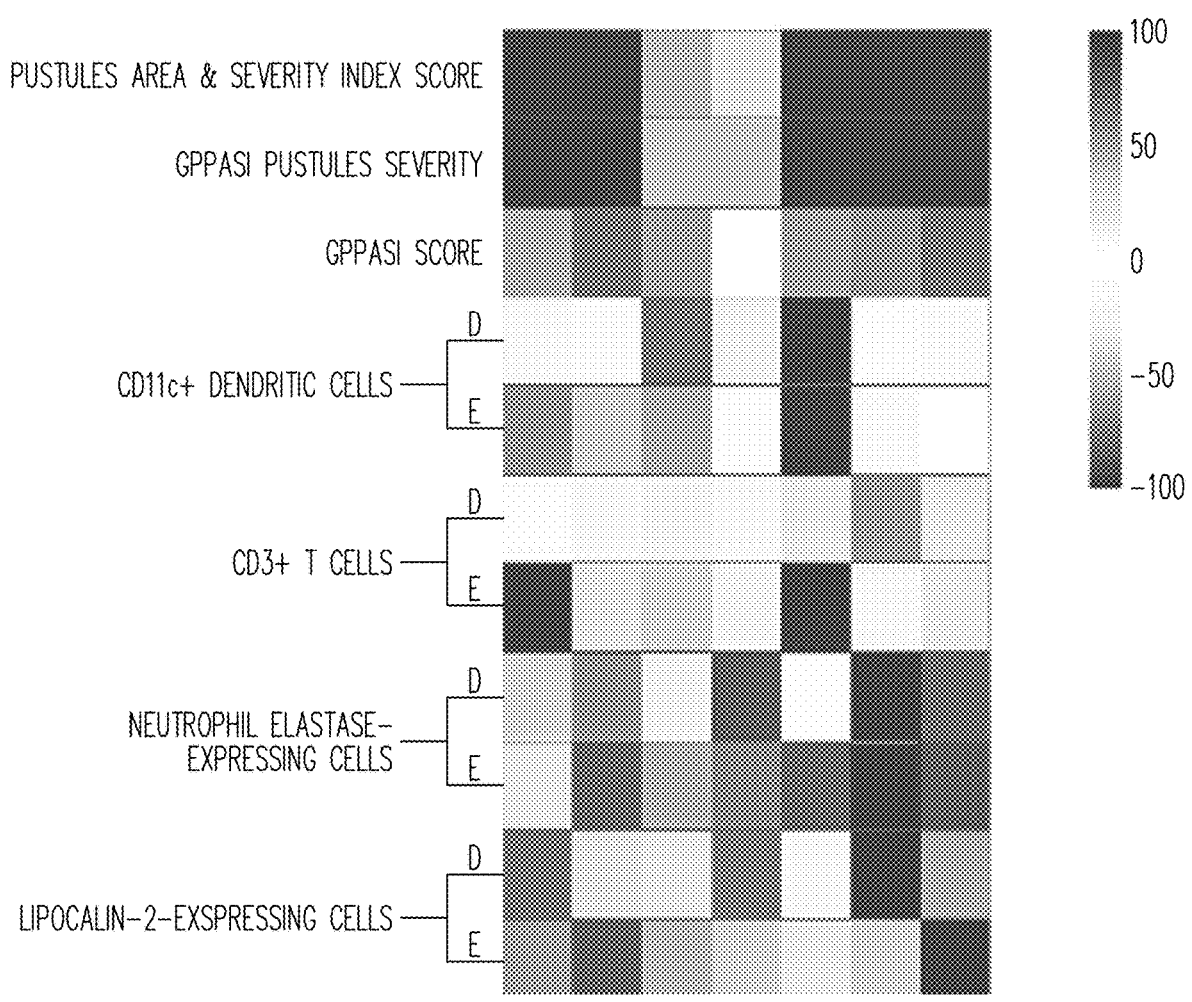
FIG. 2A-2B shows the change in immunohistochemical biomarker scores after treatment with spesolimab in GPP skin lesions.
Figure 2B:
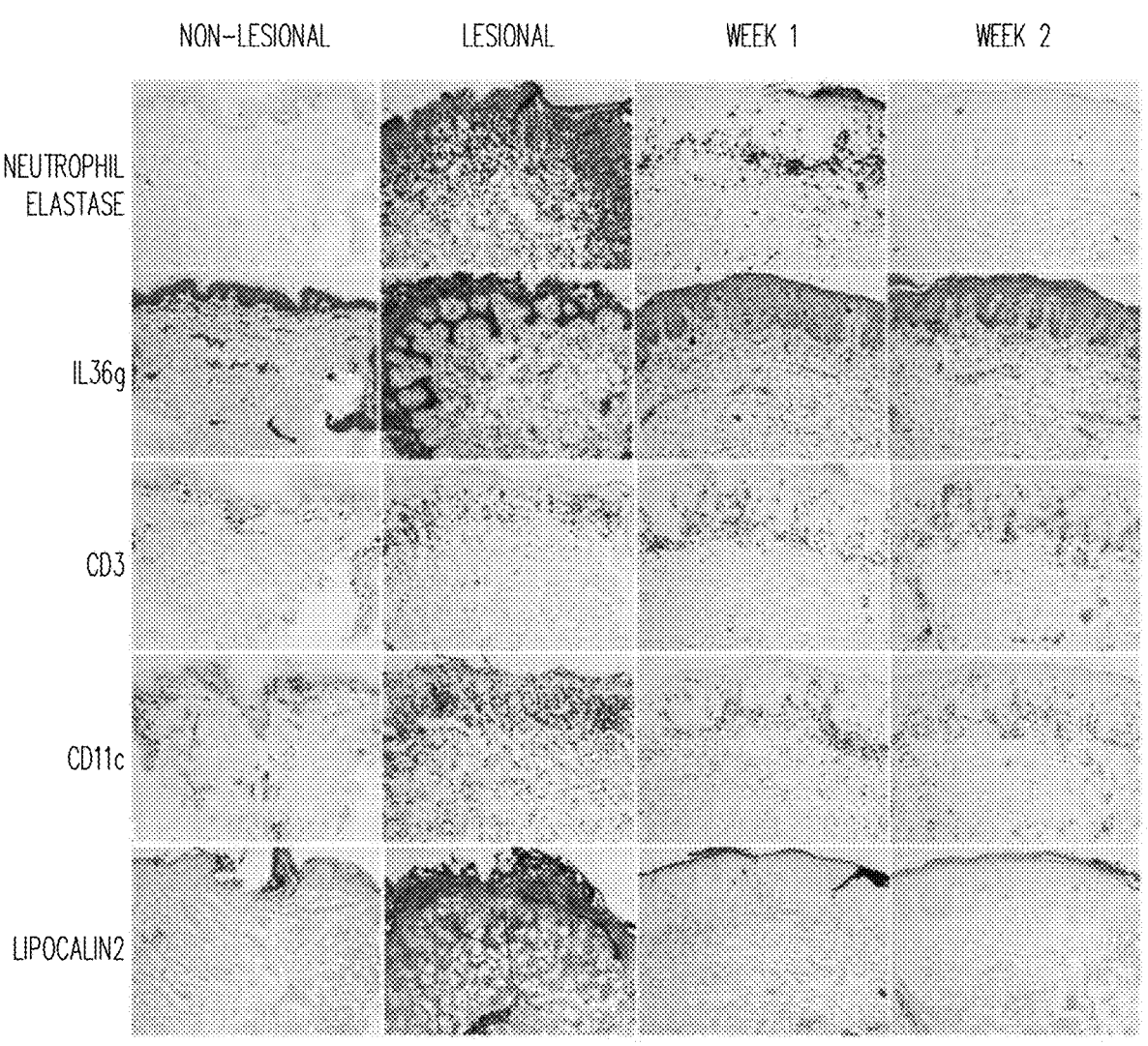

In addition, as early as Week 1, spesolimab treatment selectively decreased the expression of IHC biomarkers, including the number of CD11c+ dendritic cells, CD3+ T cells, neutrophil elastase-, lipocalin-2- and IL-36γ-expressing cells (FIGS. 2A and 2B). These reductions were accompanied by decreases in clinical severity (FIG. 2A).

Figure 3A:
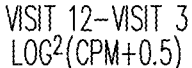
FIG. 3A-3C shows the changes in peripheral biomarkers in blood and plasma following treatment with spesolimab in patients with GPP.
Figure 3A:
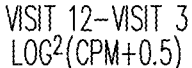
Figure 3A:
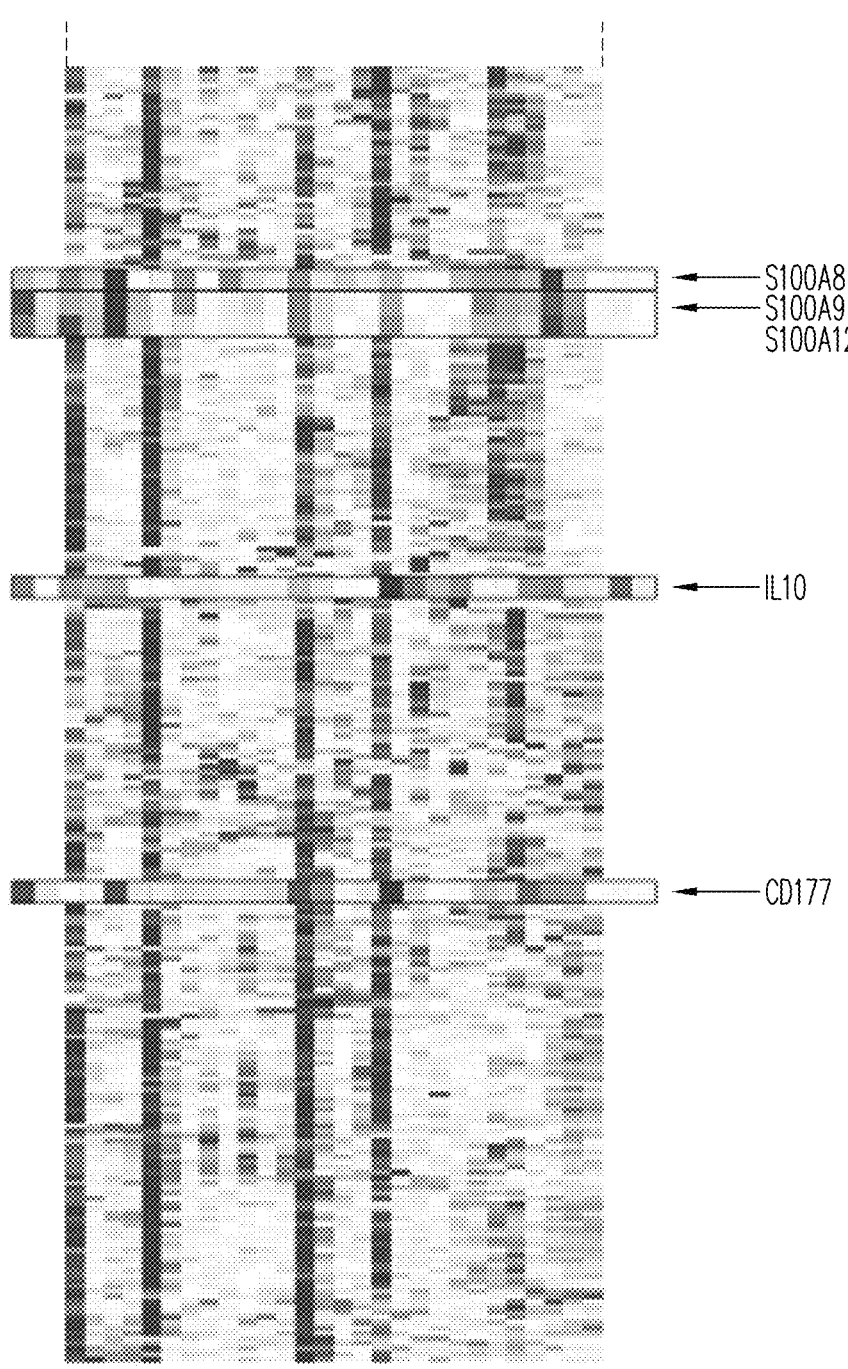
Figure 3B:
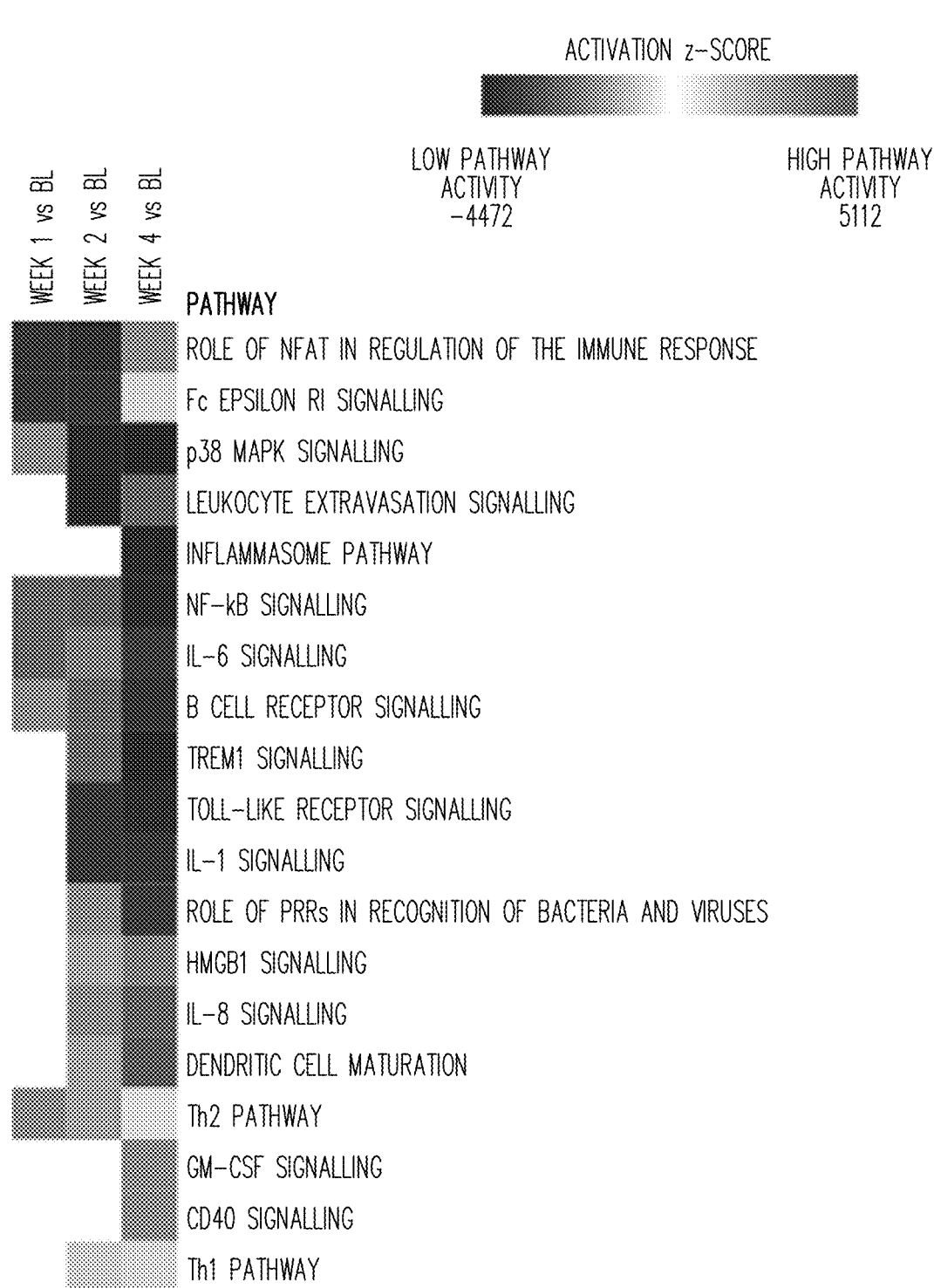
Figure 3C:
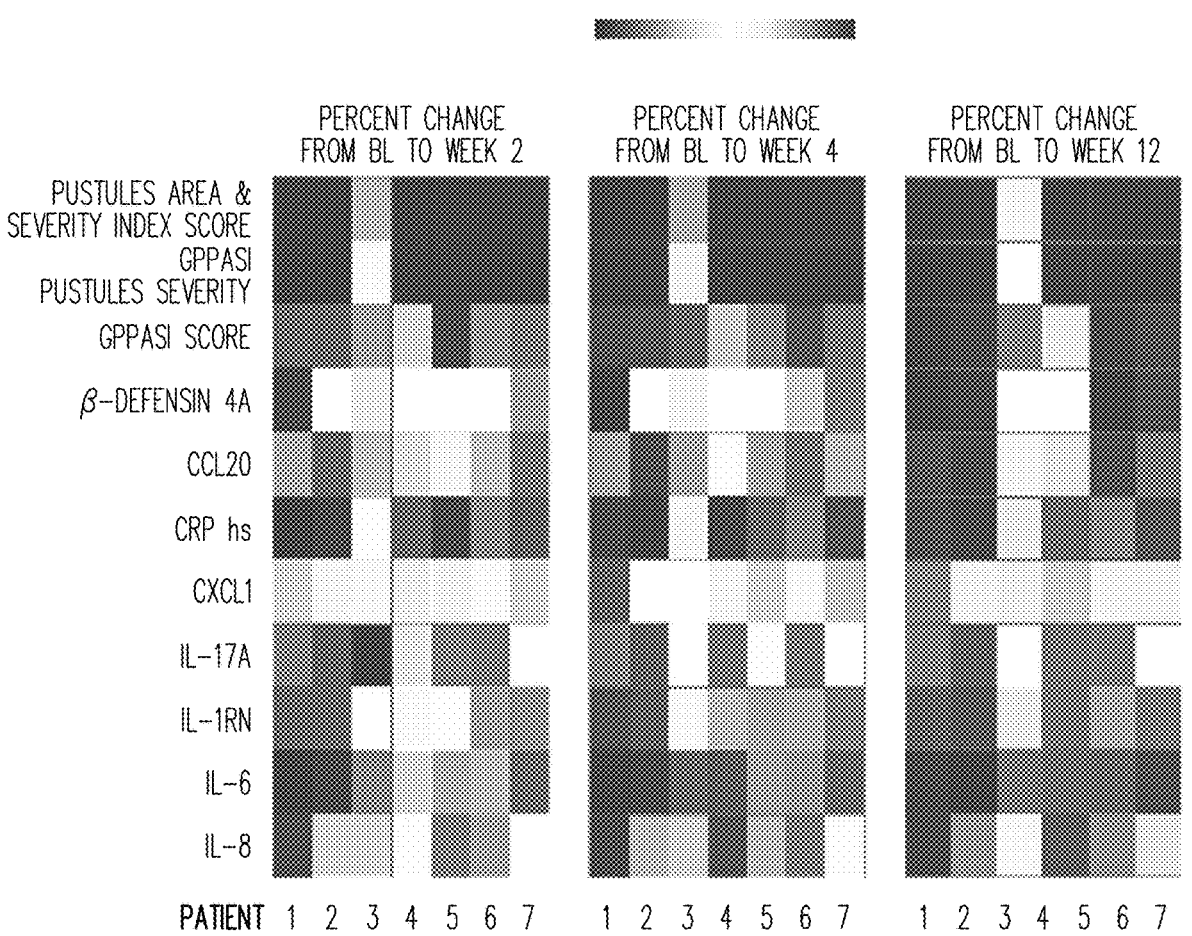

RNA-seq performed in whole blood detected DEGs at Weeks 1, 2, and 4 compared with baseline (364, 476 and 568 genes, respectively; adjusted P≤0.05, fold change ≥2), with 319 commonly DEGs between Weeks 2 and 4. Proinflammatory mediators involved in neutrophil activation, including IL10, CD177, S100A8/9, S100A12 and MMP9, were among the genes identified to be most strongly downregulated at different timepoints after treatment (FIG. 3A). Comparisons of activity at baseline to Weeks 1, 2 and 4 post spesolimab treatment showed sustained downregulation of immune response pathways, as identified using IPA (FIG. 3B).

Baseline levels of serum biomarkers β-defensin 4A, CCL20, CXCL1, IL-17A, IL-1 RN, IL-6 and IL-8 were variable across the seven patients (median [quartile 1, quartile 3], ng/L: β-defensin 4A, 28,804.8 [22,424.8, 28,804.8]; CCL20, 38.2 [12.1, 111.8]; CXCL1, 341.5 [187.4, 525.2]; IL-17A, 2.5 [0.7, 2.9]; IL-1 RN, 560.6 [163.2, 993.0]; IL-6, 41.2 [14.2, 188.7]; IL-8, 50.5 [18.5, 134.6]). Treatment with spesolimab led to marked downregulation of select serum biomarkers linked to inflammatory (e.g. C-reactive protein, β-defensin 4A), neutrophilic (e.g. CXCL1, IL-8), innate (e.g. IL-1 RN, IL-6) and Th17 (e.g. IL-17A, CCL20) pathways as early as Week 2 in select patients; these reductions were accompanied by decreases in clinical disease severity (FIG. 30). See also Table 1.

TABLE 1

| Top 50 differentially expressed genes (incldung fold change, pvalue and adjusted pvalue) in lesional skin pre and post treatment with spesolimab. | | | | |
|---|---|---|---|---|
| Ensembl gene ID | HGNC | Log2 Fold change VISIT9 vs VISIT3 | pValues VISIT9 vs VISIT3 | Adjusted pValues VISIT9 vs VISIT3 |
| ENSG00000108342 | CSF3 | −4.74088102 | 0.0079781 | 0.03637123 |
| ENSG00000162892 | IL24 | −4.35708057 | 0.00487161 | 0.02786815 |
| ENSG00000142224 | IL19 | −3.9660122 | 0.00496594 | 0.02810991 |
| ENSG00000162891 | IL20 | −3.7524392 | 0.00164141 | 0.01735926 |
| ENSG00000136244 | IL6 | −3.67317327 | 0.0044921 | 0.02666965 |
| ENSG00000124391 | IL17C | −3.60900729 | 0.00426816 | 0.02596593 |
| ENSG00000113302 | IL12B | −3.42466655 | 0.00068099 | 0.01255625 |
| ENSG00000263426 | RN7SL471P | −3.40390066 | 0.00248866 | 0.02048129 |
| ENSG00000163661 | PTX3 | −3.33345876 | 0.00528475 | 0.02895902 |
| ENSG00000179826 | MRGPRX3 | −3.07363966 | 0.00190363 | 0.01838095 |
| ENSG00000129988 | LBP | −2.97584579 | 0.00704837 | 0.03399448 |
| ENSG00000164047 | CAMP | −2.92409414 | 0.00389863 | 0.02491137 |
| ENSG00000110944 | IL23A | −2.8952076 | 0.00346823 | 0.02354341 |
| ENSG00000172602 | RND1 | −2.84842563 | 0.00076866 | 0.01293981 |
| ENSG00000158859 | ADAMTS4 | −2.8454902 | 0.00016702 | 0.01094397 |
| ENSG00000134668 | SPOCD1 | −2.81598394 | 0.00189836 | 0.01836339 |
| ENSG00000262814 | MRPL12 | −2.67437157 | 0.01314382 | 0.04935877 |
| ENSG00000163739 | CXCL1 | −2.67052924 | 0.00326973 | 0.02305719 |
| ENSG00000123689 | G0S2 | −2.57158919 | 0.00491452 | 0.02796448 |
| ENSG00000231123 | SPATA20P1 | −2.51714251 | 0.00739987 | 0.03495342 |
| ENSG00000189410 | SH2D5 | −2.43001543 | 0.00135778 | 0.01599897 |
| ENSG00000184557 | SOCS3 | −2.37954148 | 0.00198251 | 0.01871687 |
| ENSG00000181649 | PHLDA2 | −2.37824334 | 0.00075578 | 0.01290546 |
| ENSG00000257335 | MGAM | −2.36888182 | 0.00901432 | 0.03907333 |
| ENSG00000091137 | SLC26A4 | −2.33328282 | 0.0069774 | 0.0338197 |
| ENSG00000100985 | MMP9 | −2.31713739 | 0.00132499 | 0.01594817 |
| ENSG00000159339 | PADI4 | −2.30791137 | 0.00747457 | 0.03514 |
| ENSG00000175592 | FOSL1 | −2.2870487 | 0.00261917 | 0.02095618 |
| ENSG00000188389 | PDCD1 | −2.28592236 | 0.00073004 | 0.01282036 |
| ENSG00000125148 | MT2A | −2.28138957 | 3.4863E−05 | 0.01094397 |
| ENSG00000229035 | SPRR2C | −2.28015765 | 0.00520157 | 0.02872806 |
| ENSG00000171631 | P2RY6 | −2.26336359 | 1.5754E−05 | 0.01094397 |
| ENSG00000198535 | C2CD4A | −2.26163584 | 0.00198179 | 0.01871687 |
| ENSG00000099985 | OSM | −2.26061026 | 0.00575847 | 0.03042149 |
| ENSG00000125538 | IL1B | −2.2585177 | 0.01328167 | 0.04963035 |
| ENSG00000259230 | | −2.21902494 | 0.0003323 | 0.01110959 |
| ENSG00000111012 | CYP27B1 | −2.21701925 | 0.00047675 | 0.0116585 |
| ENSG00000005001 | PRSS22 | −2.21093725 | 0.00215497 | 0.01915111 |
| ENSG00000275395 | FCGBP | −2.20402093 | 1.3103E−07 | 0.00242084 |
| ENSG00000187116 | LILRA5 | −2.19638079 | 0.00909475 | 0.03923293 |
| ENSG00000196136 | SERPINA3 | −2.16337735 | 0.00288674 | 0.02174291 |
| ENSG00000124216 | SNAI1 | −2.14783417 | 9.652E−05 | 0.01094397 |
| ENSG00000277048 | | −2.1414334 | 0.00859644 | 0.03790642 |
| ENSG00000198959 | TGM2 | −2.13859752 | 0.00135537 | 0.01599897 |
| ENSG00000070729 | CNGB1 | −2.12908082 | 0.01266926 | 0.04814421 |
| ENSG00000177943 | MAMDC4 | −2.12658565 | 1.9058E−05 | 0.01094397 |

TABLE 1-continued

Top 50 differentially expressed genes (incldung fold change, pvalue and
adjusted pvalue) in lesional skin pre and post treatment with spesolimab.

| Ensembl gene ID | HGNC | Log2 Fold change VISIT9 vs VISIT3 | pValues VISIT9 vs VISIT3 | Adjusted pValues VISIT9 vs VISIT3 |
|---|---|---|---|---|
| ENSG00000125144 | MT1G | −2.10288036 | 0.00082735 | 0.01330472 |
| ENSG00000171223 | JUNB | −2.09814442 | 0.00020919 | 0.01094397 |
| ENSG00000185338 | SOCS1 | −2.09194354 | 1.0638E−05 | 0.01094397 |
| ENSG00000137757 | CASP5 | −2.09138024 | 0.00050731 | 0.01177523 |

For example, differentially expressed genes/proteins associated with the pro-inflammatory mediators (TNF, IL1B, IL6), neutrophil recruitment mediators (CXCL1, CXCL2, CXCL3, CXCL5, CXCL6, CXCL8, CXCR1, CXCR1, CXCR2), neutrophil-expressed transcripts (NCF1, NCF2, NCF4, ELANE) or in keratinocyte activation, differentiation and mediated inflammation transcripts (IL36A, IL36G, IL17C, IL19, IL20, IL22, IL24) were found in lesional skin after 1 week of spesolimab treatment (FIG. 1C). Strong inhibition of T-cell activity was observed after spesolimab treatment, including T helper (Th)1/Th2 pathways and CD28 signalling in Th cells (FIGS. 1A and 1B), and this was associated with the downregulation of elevated IL17C (FIG. 1C).

Discussion

To our knowledge, this is the first study conducted to assess the global transcriptome profiles and gene set analysis in GPP. Here, we show that compared with healthy samples, GPP skin lesions modulated genes linked to Th1 and Th17 and innate inflammation signalling, neutrophilic activation and recruitment mediators, IL-36 and keratinocyte-driven inflammation pathways. Interestingly, most of the DEGs in the GPP transcriptome were unique to this disease (83.1%).

These results are consistent with genetic mutations and dysregulated gene expression previously reported in GPP. Genetic studies in patients with GPP have identified loss-of-function mutations in IL36RN and other genes functionally-associated with the IL-36 pathway, (e.g. AP1S3) and gain-of-function mutations in CARD14. In addition, transcriptome analysis of GPP lesions has shown an increase in innate immune inflammation response over Th1/Th17-related transcripts, including increased expression of genes encoding for IL-1p, IL-36a and IL-36γ, and enriched neutrophil and monocyte transcripts such as CXCL1, CXCL2, CXCL8.

Previously, the central role of IL-36 in the immunopathology of GPP was further supported by results from a proof-of-concept study to evaluate the efficacy and safety of spesolimab in patients with GPP. In this study, a single dose of 10 mg/kg intravenous spesolimab resulted in rapid (within 7 days) and sustained improvements (up to Week 20) in the clinical signs and symptoms of GPP. Further comparisons of the cellular and molecular expression patterns in non-lesional and lesional skin or blood from those patients revealed that spesolimab treatment resulted in a rapid normalisation or strong downregulation in levels of DEGs. This was characterised by reductions in the expression of pro-inflammatory mediators, neutrophil recruitment mediators, neutrophil-expressed transcripts and in keratinocyte activation; differentiation transcripts were found in lesional skin after 1 week of spesolimab treatment.

In addition, spesolimab induced rapid reductions of different highly infiltrated cell populations, including neutrophils, CD3+ T cells, CD11c+ cells, lipocalin-2-expressing cells, and decreased the expression of IL-36γ in lesional skin. The effects of spesolimab on T-cell subsets were consistent with the downregulation of elevated IL17C causing inhibition of the feed-forward inflammatory response and strongly affecting T-cell activation (FIG. 1C). Of relevance, these decreased gene and protein expression profiles correlated with parallel improvement in clinical disease severity and pustulation clearance (Generalized Pustular Psoriasis Area and Severity Index and pustulation severity scores); this behaviour was in line with the strong and rapid reduction of C-reactive protein values compared with baseline levels in patients who achieved pustulation clearance (GPPGA pustule subscore of 0) after treatment with spesolimab in the proof-of-concept study. This highlights the importance of IL-36 pathway inhibition in the skin and blood of patients with GPP.

Based on these biomarker results in samples collected from patients presenting with acute GPP flares, we have identified that GPP involved key dysregulated pathways associated with IL-36, Th17, neutrophilic and keratinocyte-driven inflammation. In addition, the intervention by blocking IL-36R with spesolimab resulted in a rapid normalisation/downregulation of those genes in patients with GPP, with matched clinical improvement.

Example 2: Changes in the Molecular Profile of Lesional Skin and Blood of Patients with Generalized Pustular Psoriasis Treated with Spesolimab are Associated with Clinical Response Generalized pustular psoriasis (GPP) is a rare, chronic inflammatory skin and systemic disease characterized by acute onset of disseminated pustular eruptions. GPP is associated with significant morbidity, and GPP flares can be life-threatening if untreated. The pathogenesis of GPP involves dysregulated interleukin (IL)-36 signaling. Spesolimab, a monoclonal antibody that targets the IL-36 receptor, was efficacious in patients experiencing a GPP flare. In the Effisayil™ 1 study, spesolimab resulted in rapid pustular and skin clearance within 1 week versus placebo in patients experiencing a GPP flare. We identified 5208 gene transcripts that were differentially expressed (2861 decreased, 2347 elevated) in lesional versus non-lesional skin biopsies (adjusted p-value ≤0.05, log 2 fold change 1) at baseline. These included genes associated with the IL-36 family (IL36A, IL36B, IL36G), neutrophilic recruitment (CXCL1, CXCL6, CXCL8), proinflammatory cytokines (IL6, IL19, IL20), and skin inflammation (DEFB4a, S100A7, S100A8, S100A9). A significant number of genes in lesional skin were modulated 1 week after (324 decreased, 622 increased; adjusted p-value 50.05, log 2 fold change 1) and 7-8 weeks after (1115 decreased, 1425 increased; adjusted p-value 50.05, log 2 fold change 1) a single dose of spesolimab (900 mg intravenously). Patients who achieved the primary endpoint (GPP Physician Global Assessment pustulation sub-score of 0 by Week 1) demonstrated significant changes from baseline in differentially expressed genes in lesional skin. Histopathological changes in select biomarkers (NE, K16, beta defensin 2, IL-17C) were observed in lesional versus non-lesional skin pre-versus post-treatment at Week 8. There were also reductions in serum biomarker levels, including IL-17C, IL-20, TGF-α, IL-24, CCL4, CCL19, IL1-RN, and CCL20, which were sustained until Week 12 and correlated with primary endpoint achievement. In summary, the clinical efficacy of spesolimab in patients with a GPP flare in the Effisayil™ 1 study was associated with modulation of key pathogenic pathways in skin and blood. See Table 2.

TABLE 2

Correlation of change from baseline of protein biomarker with GPPGA score of 0 or 1 at week 1 per treatment group - SAF (sorted by p-value)

| Paremeter | Treatment | | Correla-tion coefficient | 95% Confidence interval Lower | Doper | p-value |
|---|---|---|---|---|---|---|
| Interleukin-17A [NPX] | Speso 900 mg IV SD | 26 | −0.699 | −0.855 | −0.427 | <.001 |
| Interleukin-17C [NPX] | Speso 900 mg IV SD | 26 | −0.662 | −0.835 | −0.369 | <.001 |
| Interleukin-20 [NPX] | Speso 900 mg IV SD | 26 | −0.635 | −0.821 | −0.329 | <.001 |
| Trail receptor 1 [NPX] | Speso 900 mg IV SD | 27 | −0.578 | −0.786 | −0.254 | 0.001 |
| Interleukin-24 [NPX] | Speso 900 mg IV SD | 24 | −0.603 | −0.810 | −0.264 | 0.001 |
| Trail receptor 2 [NPX] | Speso 900 mg IV SD | 27 | −0.565 | −0.778 | −0.235 | 0.001 |
| MME (NPX] | Speso 900 mg IV SD | 27 | −0.559 | −0.775 | −0.228 | 0.002 |
| IL-12B [NPX] | Speso 900 mg IV SD | 26 | −0.566 | −0.782 | −0.229 | 0.002 |
| IL-27 [NPX] | Speso 900 mg IV SD | 27 | −0.555 | −0.772 | −0.222 | 0.002 |
| FGF-2 [NPX] | Speso 900 mg IV SD | 26 | −0.558 | −0.777 | −0.217 | 0.002 |
| C-C motif chemokine 19 [NPX] | Speso 900 mg IV SD | 26 | −0.543 | −0.768 | −0.196 | 0.003 |
| CSF-1 [NPX] | Speso 900 mg IV SD | 26 | −0.521 | −0.756 | −0.167 | 0.005 |
| C-C motif chemokine 20 [NPX] | Speso 900 mg IV SD | 26 | −0.498 | −0.742 | −0.138 | 0.008 |
| IL-1RN [NPX] | Speso 900 mg IV SD | 27 | −0.482 | −0.728 | −0.125 | 0.009 |
| C-C motif chemokine [NPX] | Speso 900 mg IV SD | 26 | −0.473 | −0.727 | −0.104 | 0.012 |
| ODFR [NPX] | Speso 900 mg IV SD | 27 | −0.460 | −0.715 | −0.096 | 0.013 |
| Placenta growth factor [NPX] | Speso 900 mg IV SD | 27 | −0.457 | −0.713 | −0.093 | 0.014 |
| TGF-alpha [NPX] | Speso 900 mg IV SD | 26 | −0.458 | −0.718 | −0.085 | 0.016 |
| Oncostatin-M [NPX] | Speso 900 mg IV SD | 26 | −0.453 | −0.715 | −0.079 | 0.017 |
| Interleukin-18 receptor 1 [NPX] | Speso 900 mg IV SD | 26 | −0.042 | −0.708 | −0.066 | 0.020 |
| Hepatocyte growth factor [NPX] | Speso 900 mg IV SD | 26 | −0.441 | −0.707 | −0.064 | 0.021 |

Pearson correlation coefficient with Fisher's Z test p-values,
OC approach is used for the protein biomarkers. NRI imputation is applied for GPPGA.
Correlation coefficient for placebo group was omitted due to very small number of responders in the placebo group.

While certain aspects and embodiments of the invention have been described, these have been presented by way of example only, and are not intended to limit the scope of the invention. Indeed, the novel methods and systems described herein may be embodied in a variety of other forms without departing from the spirit thereof. The accompanying claims and their equivalents are intended to cover such forms or modifications as would fall within the scope and spirit of the invention.

All patents and/or publications including journal articles cited in this disclosure are expressly incorporated herein by reference.

The invention claimed is:

1. A method of monitoring a GPP patient's beneficial response and adjusting treatment for generalized pustular psoriasis (GPP) in a GPP patient experiencing an acute flare after administration of a single intravenous dose of an anti-interleukin-36 receptor antibody (anti-IL-36R antibody), comprising:

a) obtaining, at baseline (pre-dose) and at weeks 1, 2 and/or 4 post-administration blood form the GPP patient;

b) isolating plasma and quantifying in each time-point sample the expression level or concentration of at least three GPP biomarkers selected from pro-inflammatory processes (TNF, IL1B, IL6), neutrophil recruitment (CXCL1, CXCL2, CXCL3, CXCL5, CXCL6, CXCL8, CXCR1, CXCR1, CXCR2), neutrophil occurrence (NCF1, NCF2, NCF4, ELANE) or in keratinocyte activation, differentiation and mediated inflammation transcripts (IL36A, IL36G, IL17C, IL19, IL20, IL22, IL24), CSF3, IL24, IL19, IL20, IL6, IL17C, IL12B, RN7SL471P, PTX3, MRGPRX3, LBP, CAMP, IL23A, RND1, ADAMTS4, SPOCD1, MRPL12, CXCL1, GOS2, SPATA20P1, SH2D5, SOCS3, PHLDA2, MGAM, SLC26A4, MMP9, PADI4, FOSL1, PDCD1, MT2A, SPRR2C, P2RY6, C2CD4A, OSM, IL1B, CYP27B1, PRSS22, FCGBP, LILRA5, SERPINA3, SNAI1, TGM2, CNGB1, MAMDC4, MT1G, JUNB, SOCS1 or CASP5 by a validated QPCR assay, ELISA, or other protein detection method c) computing, with a configured processor executing a pre-specified analysis pipeline, an activation z-score using pathway analysis at each post-dose time-point, the score comprising biomarker measurements relative to baseline;

(d) classifying the patient as a responder when said biomarker score indicates ≥50% down-regulation relative to baseline at post-dose time-points; and (e) optionally adjusting treatment for the patient based on the classification, comprising administering an additional anti-IL-36R dose within 1-4 weeks.

2. The method of claim 1, wherein the anti-IL-36R antibody is spesolimab.

* * * * *

SEQUENCE LISTING

```
<160> NUMBER OF SEQ ID NOS: 140

<210> SEQ ID NO 1
<211> LENGTH: 108
<212> TYPE: PRT
<213> ORGANISM: Mus sp.

<400> SEQUENCE: 1

Gln Ile Val Leu Thr Gln Ser Pro Ala Ile Met Ser Ala Ser Leu Gly
1               5                   10                  15

Glu Arg Val Thr Met Thr Cys Thr Ala Ser Ser Ser Val Ser Ser Ser
            20                  25                  30

Tyr Leu His Trp Tyr Gln Lys Lys Pro Gly Ser Ser Pro Lys Leu Trp
        35                  40                  45
```

-continued

```
Val Tyr Ser Thr Ser Asn Leu Ala Ser Gly Val Pro Val Arg Phe Ser
    50                  55                  60

Gly Ser Gly Ser Gly Thr Ser Tyr Ser Leu Thr Ile Ser Ser Met Glu
65                  70                  75                  80

Ala Glu Asp Ala Ala Thr Tyr Tyr Cys His Gln His His Arg Ser Pro
                85                  90                  95

Val Thr Phe Gly Ser Gly Thr Lys Leu Glu Met Lys
            100                 105

<210> SEQ ID NO 2
<211> LENGTH: 107
<212> TYPE: PRT
<213> ORGANISM: Mus sp.

<400> SEQUENCE: 2

Asp Ile Gln Met Thr Gln Ser Pro Ala Ser Gln Ser Ala Ser Leu Gly
1               5                   10                  15

Glu Ser Val Thr Phe Thr Cys Leu Ala Ser Gln Thr Ile Gly Thr Trp
                20                  25                  30

Leu Ala Trp Tyr Gln Gln Arg Pro Gly Lys Ser Pro Gln Leu Leu Ile
            35                  40                  45

Tyr Ala Ala Thr Ser Leu Ala Asp Gly Val Pro Ser Arg Phe Ser Gly
    50                  55                  60

Ser Gly Ser Gly Thr Gln Phe Ser Phe Asn Ile Arg Ser Leu Gln Ala
65                  70                  75                  80

Glu Asp Phe Ala Ser Tyr Tyr Cys Gln Gln Val Tyr Thr Thr Pro Leu
                85                  90                  95

Thr Phe Gly Gly Gly Thr Lys Leu Glu Ile Lys
            100                 105

<210> SEQ ID NO 3
<211> LENGTH: 107
<212> TYPE: PRT
<213> ORGANISM: Mus sp.

<400> SEQUENCE: 3

Asp Ile Gln Met Thr Gln Ser Pro Ala Ser Gln Ser Ala Ser Leu Gly
1               5                   10                  15

Glu Ser Val Thr Phe Thr Cys Leu Ala Ser Gln Thr Ile Gly Thr Trp
                20                  25                  30

Leu Gly Trp Tyr Gln Gln Lys Pro Gly Lys Ser Pro Gln Leu Leu Ile
            35                  40                  45

Tyr Arg Ser Thr Thr Leu Ala Asp Gly Val Pro Ser Arg Phe Ser Gly
    50                  55                  60

Ser Gly Ser Gly Thr Lys Phe Ser Phe Lys Ile Ser Ser Leu Gln Ala
65                  70                  75                  80

Ala Asp Phe Ala Ser Tyr Tyr Cys Gln Gln Leu Tyr Ser Ala Pro Tyr
                85                  90                  95

Thr Phe Gly Gly Gly Thr Lys Leu Glu Ile Arg
            100                 105

<210> SEQ ID NO 4
<211> LENGTH: 112
<212> TYPE: PRT
<213> ORGANISM: Mus sp.

<400> SEQUENCE: 4
```

```
Asp Val Leu Leu Thr Gln Thr Pro Leu Ser Leu Pro Val Ser Leu Gly
1               5                   10                  15

Asp Gln Ala Ser Ile Ser Cys Arg Ser Ser Gln Asn Ile Val His Ser
            20                  25                  30

Asn Gly Asn Thr Tyr Leu Gln Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Phe Thr Phe Gly Ala Gly Thr Lys Leu Glu Leu Lys
                100                 105                 110

<210> SEQ ID NO 5
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Tyr Lys Tyr
            20                  25                  30

Leu Asn Trp Tyr Gln Gln Lys Pro Asp Gly Thr Leu Lys Leu Leu Ile
        35                  40                  45

Tyr Tyr Thr Ser Gly Leu His Ser Gly Val Pro Ser Arg Phe Ser Gly
    50                  55                  60

Ser Gly Ser Gly Thr Asp Phe Ser Leu Thr Ile Ser Asn Leu Glu Pro
65                  70                  75                  80

Glu Asp Ile Ala Thr Tyr Phe Cys Gln Gln Asp Ser Lys Phe Pro Trp
                85                  90                  95

Thr Phe Gly Gly Asp Thr Lys Leu Glu Ile Lys
                100                 105

<210> SEQ ID NO 6
<211> LENGTH: 108
<212> TYPE: PRT
<213> ORGANISM: Mus sp.

<400> SEQUENCE: 6

Gln Ile Val Leu Thr Gln Ser Pro Ala Ile Met Ser Ala Ser Leu Gly
1               5                   10                  15

Glu Arg Val Thr Met Thr Cys Thr Ala Ser Ser Ser Val Ser Ser Ser
            20                  25                  30

Tyr Phe His Trp Tyr Gln Gln Lys Pro Gly Ser Ser Pro Lys Leu Trp
        35                  40                  45

Ile Tyr Arg Thr Ser Asn Leu Ala Ser Gly Val Pro Gly Arg Phe Ser
    50                  55                  60

Gly Ser Gly Ser Gly Thr Ser Tyr Ser Leu Thr Ile Ser Ser Met Glu
65                  70                  75                  80

Ala Glu Asp Ala Ala Thr Tyr Tyr Cys His Gln Phe His Arg Ser Pro
                85                  90                  95
```

```
Leu Thr Phe Gly Ala Gly Thr Lys Leu Glu Leu Lys
            100             105

<210> SEQ ID NO 7
<211> LENGTH: 107
<212> TYPE: PRT
<213> ORGANISM: Mus sp.

<400> SEQUENCE: 7

Asp Ile Val Met Thr Gln Ser Gln Lys Phe Leu Ser Thr Ser Val Gly
1               5                   10                  15

Val Arg Val Ser Val Thr Cys Lys Ala Ser Gln Asp Val Gly Thr Asn
                20                  25                  30

Val Leu Trp Tyr Gln Gln Lys Ile Gly Gln Ser Pro Lys Pro Leu Ile
            35                  40                  45

Tyr Ser Ala Ser Tyr Arg His Ser Gly Val Pro Asp Arg Phe Thr Gly
        50                  55                  60

Ser Gly Ser Gly Thr Asp Phe Thr Leu Ile Ile Ser Asn Val Gln Ser
65                  70                  75                  80

Glu Asp Leu Ala Glu Tyr Phe Cys Gln Gln Tyr Ser Arg Tyr Pro Leu
                85                  90                  95

Thr Phe Gly Pro Gly Thr Lys Leu Glu Leu Lys
            100             105

<210> SEQ ID NO 8
<211> LENGTH: 107
<212> TYPE: PRT
<213> ORGANISM: Mus sp.

<400> SEQUENCE: 8

Asp Ile Val Met Thr Gln Ser Gln Lys Phe Leu Ser Thr Ser Val Gly
1               5                   10                  15

Val Arg Val Ser Val Thr Cys Lys Ala Ser Gln Asp Val Gly Thr Asn
                20                  25                  30

Val Leu Trp Tyr Gln Gln Lys Ile Gly Gln Ser Pro Lys Ala Leu Ile
            35                  40                  45

Tyr Ser Ala Ser Tyr Arg His Ser Gly Val Pro Asp Arg Phe Thr Gly
        50                  55                  60

Ser Gly Ser Gly Thr Asp Phe Thr Leu Ile Ile Thr Asn Val Gln Ser
65                  70                  75                  80

Glu Asp Leu Ala Glu Tyr Phe Cys Gln Gln Tyr Ser Arg Tyr Pro Leu
                85                  90                  95

Thr Phe Gly Pro Gly Thr Lys Leu Glu Leu Lys
            100             105

<210> SEQ ID NO 9
<211> LENGTH: 107
<212> TYPE: PRT
<213> ORGANISM: Mus sp.

<400> SEQUENCE: 9

Asp Ile Val Met Thr Gln Ser Gln Lys Phe Met Ser Ala Thr Val Gly
1               5                   10                  15

Gly Arg Val Asn Ile Thr Cys Lys Ala Ser Gln Asn Val Gly Arg Ala
                20                  25                  30

Val Ala Trp Tyr Gln Gln Lys Pro Gly Gln Ser Pro Lys Leu Leu Thr
            35                  40                  45

His Ser Ala Ser Asn Arg Tyr Thr Gly Val Pro Asp Arg Phe Thr Gly
```

-continued

```
            50                  55                  60

Ser Gly Ser Gly Thr Asp Phe Thr Leu Thr Ile Thr Asn Met Gln Ser
65                  70                  75                  80

Glu Asp Leu Ala Asp Tyr Phe Cys Gln Gln Tyr Ser Ser Tyr Pro Leu
                85                  90                  95

Thr Phe Gly Ala Gly Thr Lys Leu Asp Leu Lys
            100                 105

<210> SEQ ID NO 10
<211> LENGTH: 107
<212> TYPE: PRT
<213> ORGANISM: Mus sp.

<400> SEQUENCE: 10

Asp Ile Gln Met Thr Gln Ser Pro Ala Ser Gln Ser Ala Ser Leu Gly
1               5                   10                  15

Glu Ser Val Thr Phe Ser Cys Leu Ala Ser Gln Thr Ile Gly Thr Trp
                20                  25                  30

Leu Gly Trp Tyr Gln Gln Lys Pro Gly Lys Ser Pro Gln Leu Leu Ile
            35                  40                  45

Tyr Arg Ala Thr Ser Leu Ala Asp Gly Val Pro Ser Arg Phe Ser Gly
        50                  55                  60

Ser Gly Ser Gly Thr Asn Phe Ser Phe Lys Ile Ser Ser Leu Gln Ala
65                  70                  75                  80

Glu Asp Leu Ala Ser Tyr Tyr Cys Gln Gln Leu Tyr Ser Gly Pro Tyr
                85                  90                  95

Thr Phe Gly Gly Gly Thr Lys Leu Glu Ile Arg
            100                 105

<210> SEQ ID NO 11
<211> LENGTH: 119
<212> TYPE: PRT
<213> ORGANISM: Mus sp.

<400> SEQUENCE: 11

Gln Val Gln Leu Gln Gln Ser Gly Thr Glu Leu Leu Lys Pro Gly Ala
1               5                   10                  15

Ser Val Lys Leu Ser Cys Lys Ala Ser Gly Asn Thr Val Thr Ser Tyr
                20                  25                  30

Trp Met His Trp Val Lys Gln Arg Pro Gly Gln Gly Leu Glu Trp Ile
            35                  40                  45

Gly Glu Ile Leu Pro Ser Thr Gly Arg Thr Asn Tyr Asn Glu Asn Phe
        50                  55                  60

Lys Gly Lys Ala Met Leu Thr Val Asp Lys Ser Ser Ser Thr Ala Tyr
65                  70                  75                  80

Met Gln Leu Ser Ser Leu Ala Ser Glu Asp Ser Ala Val Tyr Tyr Cys
                85                  90                  95

Thr Ile Val Tyr Phe Gly Asn Pro Trp Phe Ala Tyr Trp Gly Gln Gly
            100                 105                 110

Thr Leu Val Thr Val Ser Ala
        115

<210> SEQ ID NO 12
<211> LENGTH: 125
<212> TYPE: PRT
<213> ORGANISM: Mus sp.

<400> SEQUENCE: 12
```

-continued

```
Glu Val Gln Leu Gln Gln Ser Gly Pro Glu Leu Val Lys Pro Gly Ala
1               5                   10                  15

Ser Val Lys Leu Ser Cys Lys Ala Ser Gly Tyr Thr Phe Thr Asp Asn
            20                  25                  30

Tyr Met Asn Trp Val Arg Gln Ser His Gly Lys Ser Leu Glu Trp Ile
        35                  40                  45

Gly Arg Val Asn Pro Ser Asn Gly Asp Thr Lys Tyr Asn Gln Asn Phe
    50                  55                  60

Lys Gly Lys Ala Thr Leu Thr Val Asp Lys Ser Leu Ser Thr Ala Tyr
65                  70                  75                  80

Met Gln Leu Asn Gly Leu Thr Ser Glu Asp Ser Ala Val Tyr Tyr Cys
                85                  90                  95

Gly Arg Thr Lys Asn Phe Tyr Ser Ser Tyr Ser Tyr Asp Asp Ala Met
            100                 105                 110

Asp Tyr Trp Gly Gln Gly Thr Ser Val Thr Val Ser Ser
            115                 120                 125

<210> SEQ ID NO 13
<211> LENGTH: 124
<212> TYPE: PRT
<213> ORGANISM: Mus sp.

<400> SEQUENCE: 13

Glu Val Gln Leu Gln Gln Ser Gly Ala Glu Phe Val Arg Pro Gly Ala
1               5                   10                  15

Ser Val Lys Phe Ser Cys Thr Ala Ser Gly Phe Asn Ile Lys Asp Asp
            20                  25                  30

Tyr Ile His Trp Val Arg Gln Arg Pro Glu Gln Gly Leu Glu Trp Val
        35                  40                  45

Gly Arg Ile Asp Pro Ala Asn Gly Asn Thr Lys Tyr Ala Pro Lys Phe
    50                  55                  60

Gln Asp Lys Ala Thr Ile Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Ala Lys Ser Phe Pro Asn Asn Tyr Tyr Ser Tyr Asp Asp Ala Phe Ala
            100                 105                 110

Tyr Trp Gly Gln Gly Thr Leu Val Thr Val Ser Ala
            115                 120

<210> SEQ ID NO 14
<211> LENGTH: 118
<212> TYPE: PRT
<213> ORGANISM: Mus sp.

<400> SEQUENCE: 14

Gln Val Gln Leu Lys Glu Ser Gly Pro Val Leu Val Ala Pro Ser Gln
1               5                   10                  15

Ser Leu Ser Ile Thr Cys Thr Val Ser Gly Phe Ser Leu Thr Lys Phe
            20                  25                  30

Gly Val His Trp Ile Arg Gln Thr Pro Gly Lys Gly Leu Glu Trp Leu
        35                  40                  45

Gly Val Ile Trp Ala Gly Gly Pro Thr Asn Tyr Asn Ser Ala Leu Met
    50                  55                  60

Ser Arg Leu Thr Ile Ser Lys Asp Ile Ser Gln Ser Gln Val Phe Leu
65                  70                  75                  80
```

-continued

```
Arg Ile Asp Ser Leu Gln Thr Asp Asp Thr Ala Met Tyr Tyr Cys Ala
                85                  90                  95

Lys Gln Ile Tyr Tyr Ser Thr Leu Val Asp Tyr Trp Gly Gln Gly Thr
            100                 105                 110

Ser Val Thr Val Ser Ser
        115

<210> SEQ ID NO 15
<211> LENGTH: 120
<212> TYPE: PRT
<213> ORGANISM: Mus sp.

<400> SEQUENCE: 15

Gln Val Gln Leu Lys Glu Ser Gly Pro Gly Leu Val Ala Pro Ser Gln
1               5                   10                  15

Ser Leu Phe Ile Thr Cys Thr Val Ser Gly Phe Ser Leu Ser Ser Tyr
            20                  25                  30

Glu Ile Asn Trp Val Arg Gln Val Pro Gly Lys Gly Leu Glu Trp Leu
        35                  40                  45

Gly Val Ile Trp Thr Gly Ile Thr Thr Asn Tyr Asn Ser Ala Leu Ile
    50                  55                  60

Ser Arg Leu Ser Ile Ser Lys Asp Asn Ser Lys Ser Leu Val Phe Leu
65                  70                  75                  80

Lys Met Asn Ser Leu Gln Thr Asp Asp Thr Ala Ile Tyr Tyr Cys Ala
                85                  90                  95

Arg Gly Thr Gly Thr Gly Phe Tyr Tyr Ala Met Asp Tyr Trp Gly Gln
            100                 105                 110

Gly Thr Ser Val Thr Val Ser Ser
        115                 120

<210> SEQ ID NO 16
<211> LENGTH: 119
<212> TYPE: PRT
<213> ORGANISM: Mus sp.

<400> SEQUENCE: 16

Gln Val Gln Leu Gln Gln Pro Gly Ala Asp Phe Val Arg Pro Gly Ala
1               5                   10                  15

Ser Met Arg Leu Ser Cys Lys Ala Ser Gly Tyr Ser Phe Thr Ser Ser
            20                  25                  30

Trp Ile His Trp Val Lys Gln Arg Pro Gly Gln Gly Leu Glu Trp Ile
        35                  40                  45

Gly Glu Ile Asn Pro Gly Asn Val Arg Thr Asn Tyr Asn Glu Asn Phe
    50                  55                  60

Arg Asn Lys Ala Thr Leu Thr Val Asp Lys Ser Ser Thr Thr Ala Tyr
65                  70                  75                  80

Met Gln Leu Arg Ser Leu Thr Ser Ala Asp Ser Ala Val Tyr Tyr Cys
                85                  90                  95

Thr Val Val Phe Tyr Gly Glu Pro Tyr Phe Pro Tyr Trp Gly Gln Gly
            100                 105                 110

Thr Leu Val Thr Val Ser Ala
        115

<210> SEQ ID NO 17
<211> LENGTH: 119
<212> TYPE: PRT
<213> ORGANISM: Mus sp.
```

-continued

```
<400> SEQUENCE: 17

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr Asn Tyr
            20                  25                  30

Ala Val His Trp Val Arg Gln Phe Pro Gly Lys Gly Leu Glu Trp Leu
        35                  40                  45

Gly Val Ile Trp Ser Asp Gly Ser Thr Asp Phe Asn Ala Pro Phe Lys
    50                  55                  60

Ser Arg Leu Ser Ile Asn Lys Asp Asn Ser Lys Ser Gln Val Phe Phe
65                  70                  75                  80

Lys Met Asn Ser Leu Gln Ile Asp Asp Thr Ala Ile Tyr Tyr Cys Ala
                85                  90                  95

Arg Lys Gly Gly Tyr Ser Gly Ser Trp Phe Ala Tyr Trp Gly Gln Gly
            100                 105                 110

Thr Leu Val Thr Val Ser Ala
        115

<210> SEQ ID NO 18
<211> LENGTH: 119
<212> TYPE: PRT
<213> ORGANISM: Mus sp.

<400> SEQUENCE: 18

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr Asn Tyr
            20                  25                  30

Ala Val His Trp Val Arg Gln Phe Pro Gly Lys Gly Leu Glu Trp Leu
        35                  40                  45

Gly Val Ile Trp Ser Asp Gly Ser Thr Asp Tyr Asn Ala Pro Phe Lys
    50                  55                  60

Ser Arg Leu Ser Ile Asn Lys Asp Asn Ser Lys Ser Gln Val Phe Phe
65                  70                  75                  80

Lys Met Asn Ser Leu Gln Thr Asp Asp Thr Ala Ile Tyr Tyr Cys Ala
                85                  90                  95

Arg Lys Gly Gly Tyr Ser Gly Ser Trp Phe Ala Tyr Trp Gly Gln Gly
            100                 105                 110

Thr Leu Val Thr Val Ser Ala
        115

<210> SEQ ID NO 19
<211> LENGTH: 117
<212> TYPE: PRT
<213> ORGANISM: Mus sp.

<400> SEQUENCE: 19

Gln Val Gln Leu Lys Glu Ser Gly Pro Val Leu Val Ala Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Pro Pro Gly Lys Gly Leu Glu Trp Leu
        35                  40                  45

Gly Val Ile Trp Pro Val Gly Ser Thr Asn Tyr Asn Ser Ala Leu Met
    50                  55                  60
```

-continued

```
Ser Arg Leu Ser Ile His Lys Asp Asn Ser Lys Ser Gln Val Phe Leu
65                  70                  75                  80

Arg Met Asn Ser Leu Gln Thr Asp Asp Thr Ala Ile Tyr Tyr Cys Ala
                85                  90                  95

Lys Met Asp Trp Asp Asp Phe Phe Asp Tyr Trp Gly Gln Gly Thr Thr
            100                 105                 110

Leu Thr Val Ser Ser
        115

<210> SEQ ID NO 20
<211> LENGTH: 124
<212> TYPE: PRT
<213> ORGANISM: Mus sp.

<400> SEQUENCE: 20

Glu Val Gln Leu Gln Gln Ser Gly Ala Glu Leu Val Arg Pro Gly Ala
1               5                   10                  15

Ser Val Arg Leu Ser Cys Thr Ala Ser Gly Phe Asn Ile Lys Asp Asp
            20                  25                  30

Tyr Ile His Trp Val Arg Gln Arg Pro Lys Gln Gly Leu Glu Trp Leu
        35                  40                  45

Gly Arg Ile Asp Pro Ala Asn Gly Asn Thr Lys Tyr Asp Pro Arg Phe
    50                  55                  60

Gln Asp Lys Ala Thr Ile Thr Ala Asp Thr Ser Ser Asn Thr Ala Tyr
65                  70                  75                  80

Leu His Leu Ser Ser Leu Thr Ser Glu Asp Thr Ala Val Tyr Tyr Cys
                85                  90                  95

Ala Lys Ser Phe Pro Asp Asn Tyr Tyr Ser Tyr Asp Asp Ala Phe Ala
            100                 105                 110

Tyr Trp Gly Gln Gly Thr Leu Val Thr Val Ser Ala
        115                 120

<210> SEQ ID NO 21
<211> LENGTH: 12
<212> TYPE: PRT
<213> ORGANISM: Mus sp.

<400> SEQUENCE: 21

Thr Ala Ser Ser Ser Val Ser Ser Ser Tyr Leu His
1               5                   10

<210> SEQ ID NO 22
<211> LENGTH: 11
<212> TYPE: PRT
<213> ORGANISM: Mus sp.

<400> SEQUENCE: 22

Leu Ala Ser Gln Thr Ile Gly Thr Trp Leu Ala
1               5                   10

<210> SEQ ID NO 23
<211> LENGTH: 11
<212> TYPE: PRT
<213> ORGANISM: Mus sp.

<400> SEQUENCE: 23

Leu Ala Ser Gln Thr Ile Gly Thr Trp Leu Gly
1               5                   10

<210> SEQ ID NO 24
```

```
<211> LENGTH: 16
<212> TYPE: PRT
<213> ORGANISM: Mus sp.

<400> SEQUENCE: 24

Arg Ser Ser Gln Asn Ile Val His Ser Asn Gly Asn Thr Tyr Leu Gln
1               5                   10                  15

<210> SEQ ID NO 25
<211> LENGTH: 11
<212> TYPE: PRT
<213> ORGANISM: Mus sp.

<400> SEQUENCE: 25

Arg Ala Ser Gln Asp Ile Tyr Lys Tyr Leu Asn
1               5                   10

<210> SEQ ID NO 26
<211> LENGTH: 12
<212> TYPE: PRT
<213> ORGANISM: Mus sp.

<400> SEQUENCE: 26

Thr Ala Ser Ser Ser Val Ser Ser Ser Tyr Phe His
1               5                   10

<210> SEQ ID NO 27
<211> LENGTH: 11
<212> TYPE: PRT
<213> ORGANISM: Mus sp.

<400> SEQUENCE: 27

Lys Ala Ser Gln Asp Val Gly Thr Asn Val Leu
1               5                   10

<210> SEQ ID NO 28
<211> LENGTH: 11
<212> TYPE: PRT
<213> ORGANISM: Mus sp.

<400> SEQUENCE: 28

Lys Ala Ser Gln Asn Val Gly Arg Ala Val Ala
1               5                   10

<210> SEQ ID NO 29
<211> LENGTH: 11
<212> TYPE: PRT
<213> ORGANISM: Mus sp.

<400> SEQUENCE: 29

Leu Ala Ser Gln Thr Ile Gly Thr Trp Leu Gly
1               5                   10

<210> SEQ ID NO 30
<211> LENGTH: 7
<212> TYPE: PRT
<213> ORGANISM: Mus sp.

<400> SEQUENCE: 30

Ser Thr Ser Asn Leu Ala Ser
1               5

<210> SEQ ID NO 31
<211> LENGTH: 7
<212> TYPE: PRT
```

<213> ORGANISM: Mus sp.

<400> SEQUENCE: 31

Ala Ala Thr Ser Leu Ala Asp
1               5

<210> SEQ ID NO 32
<211> LENGTH: 7
<212> TYPE: PRT
<213> ORGANISM: Mus sp.

<400> SEQUENCE: 32

Arg Ser Thr Thr Leu Ala Asp
1               5

<210> SEQ ID NO 33
<211> LENGTH: 7
<212> TYPE: PRT
<213> ORGANISM: Mus sp.

<400> SEQUENCE: 33

Lys Val Ser Asn Arg Phe Ser
1               5

<210> SEQ ID NO 34
<211> LENGTH: 7
<212> TYPE: PRT
<213> ORGANISM: Mus sp.

<400> SEQUENCE: 34

Tyr Thr Ser Gly Leu His Ser
1               5

<210> SEQ ID NO 35
<211> LENGTH: 7
<212> TYPE: PRT
<213> ORGANISM: Mus sp.

<400> SEQUENCE: 35

Arg Thr Ser Asn Leu Ala Ser
1               5

<210> SEQ ID NO 36
<211> LENGTH: 7
<212> TYPE: PRT
<213> ORGANISM: Mus sp.

<400> SEQUENCE: 36

Ser Ala Ser Tyr Arg His Ser
1               5

<210> SEQ ID NO 37
<211> LENGTH: 7
<212> TYPE: PRT
<213> ORGANISM: Mus sp.

<400> SEQUENCE: 37

Ser Ala Ser Asn Arg Tyr Thr
1               5

<210> SEQ ID NO 38
<211> LENGTH: 7
<212> TYPE: PRT
<213> ORGANISM: Mus sp.

-continued

```
<400> SEQUENCE: 38

Arg Ala Thr Ser Leu Ala Asp
1               5

<210> SEQ ID NO 39
<211> LENGTH: 9
<212> TYPE: PRT
<213> ORGANISM: Mus sp.

<400> SEQUENCE: 39

His Gln His His Arg Ser Pro Val Thr
1               5

<210> SEQ ID NO 40
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Gln Gln Val Tyr Thr Thr Pro Leu Thr
1               5

<210> SEQ ID NO 41
<211> LENGTH: 9
<212> TYPE: PRT
<213> ORGANISM: Mus sp.

<400> SEQUENCE: 41

Gln Gln Leu Tyr Ser Ala Pro Tyr Thr
1               5

<210> SEQ ID NO 42
<211> LENGTH: 9
<212> TYPE: PRT
<213> ORGANISM: Mus sp.

<400> SEQUENCE: 42

Phe Gln Gly Ser His Val Pro Phe Thr
1               5

<210> SEQ ID NO 43
<211> LENGTH: 9
<212> TYPE: PRT
<213> ORGANISM: Mus sp.

<400> SEQUENCE: 43

Gln Gln Asp Ser Lys Phe Pro Trp Thr
1               5

<210> SEQ ID NO 44
<211> LENGTH: 9
<212> TYPE: PRT
<213> ORGANISM: Mus sp.

<400> SEQUENCE: 44

His Gln Phe His Arg Ser Pro Leu Thr
1               5

<210> SEQ ID NO 45
<211> LENGTH: 9
<212> TYPE: PRT
<213> ORGANISM: Mus sp.
```

<400> SEQUENCE: 45

Gln Gln Tyr Ser Arg Tyr Pro Leu Thr
1               5

<210> SEQ ID NO 46
<211> LENGTH: 9
<212> TYPE: PRT
<213> ORGANISM: Mus sp.

<400> SEQUENCE: 46

Gln Gln Tyr Ser Ser Tyr Pro Leu Thr
1               5

<210> SEQ ID NO 47
<211> LENGTH: 9
<212> TYPE: PRT
<213> ORGANISM: Mus sp.

<400> SEQUENCE: 47

Gln Gln Leu Tyr Ser Gly Pro Tyr Thr
1               5

<210> SEQ ID NO 48
<211> LENGTH: 10
<212> TYPE: PRT
<213> ORGANISM: Mus sp.

<400> SEQUENCE: 48

Gly Asn Thr Val Thr Ser Tyr Trp Met His
1               5                   10

<210> SEQ ID NO 49
<211> LENGTH: 10
<212> TYPE: PRT
<213> ORGANISM: Mus sp.

<400> SEQUENCE: 49

Gly Tyr Thr Phe Thr Asp Asn Tyr Met Asn
1               5                   10

<210> SEQ ID NO 50
<211> LENGTH: 10
<212> TYPE: PRT
<213> ORGANISM: Mus sp.

<400> SEQUENCE: 50

Gly Phe Asn Ile Lys Asp Asp Tyr Ile His
1               5                   10

<210> SEQ ID NO 51
<211> LENGTH: 10
<212> TYPE: PRT
<213> ORGANISM: Mus sp.

<400> SEQUENCE: 51

Gly Phe Ser Leu Thr Lys Phe Gly Val His
1               5                   10

<210> SEQ ID NO 52
<211> LENGTH: 10
<212> TYPE: PRT
<213> ORGANISM: Mus sp.

<400> SEQUENCE: 52

-continued

```
Gly Phe Ser Leu Ser Ser Tyr Glu Ile Asn
1               5                   10

<210> SEQ ID NO 53
<211> LENGTH: 10
<212> TYPE: PRT
<213> ORGANISM: Mus sp.

<400> SEQUENCE: 53

Gly Tyr Ser Phe Thr Ser Ser Trp Ile His
1               5                   10

<210> SEQ ID NO 54
<211> LENGTH: 10
<212> TYPE: PRT
<213> ORGANISM: Mus sp.

<400> SEQUENCE: 54

Gly Phe Ser Leu Thr Asn Tyr Ala Val His
1               5                   10

<210> SEQ ID NO 55
<211> LENGTH: 10
<212> TYPE: PRT
<213> ORGANISM: Mus sp.

<400> SEQUENCE: 55

Gly Phe Ser Leu Thr Asn Tyr Gly Val His
1               5                   10

<210> SEQ ID NO 56
<211> LENGTH: 10
<212> TYPE: PRT
<213> ORGANISM: Mus sp.

<400> SEQUENCE: 56

Gly Phe Asn Ile Lys Asp Asp Tyr Ile His
1               5                   10

<210> SEQ ID NO 57
<211> LENGTH: 17
<212> TYPE: PRT
<213> ORGANISM: Mus sp.

<400> SEQUENCE: 57

Glu Ile Leu Pro Ser Thr Gly Arg Thr Asn Tyr Asn Glu Asn Phe Lys
1               5                   10                  15

Gly

<210> SEQ ID NO 58
<211> LENGTH: 17
<212> TYPE: PRT
<213> ORGANISM: Mus sp.

<400> SEQUENCE: 58

Arg Val Asn Pro Ser Asn Gly Asp Thr Lys Tyr Asn Gln Asn Phe Lys
1               5                   10                  15

Gly

<210> SEQ ID NO 59
<211> LENGTH: 17
<212> TYPE: PRT
<213> ORGANISM: Mus sp.
```

-continued

```
<400> SEQUENCE: 59

Arg Ile Asp Pro Ala Asn Gly Asn Thr Lys Tyr Ala Pro Lys Phe Gln
1               5                   10                  15

Asp

<210> SEQ ID NO 60
<211> LENGTH: 16
<212> TYPE: PRT
<213> ORGANISM: Mus sp.

<400> SEQUENCE: 60

Val Ile Trp Ala Gly Gly Pro Thr Asn Tyr Asn Ser Ala Leu Met Ser
1               5                   10                  15

<210> SEQ ID NO 61
<211> LENGTH: 16
<212> TYPE: PRT
<213> ORGANISM: Mus sp.

<400> SEQUENCE: 61

Val Ile Trp Thr Gly Ile Thr Thr Asn Tyr Asn Ser Ala Leu Ile Ser
1               5                   10                  15

<210> SEQ ID NO 62
<211> LENGTH: 15
<212> TYPE: PRT
<213> ORGANISM: Mus sp.

<400> SEQUENCE: 62

Glu Ile Asn Pro Gly Asn Val Arg Thr Asn Tyr Asn Glu Asn Phe
1               5                   10                  15

<210> SEQ ID NO 63
<211> LENGTH: 16
<212> TYPE: PRT
<213> ORGANISM: Mus sp.

<400> SEQUENCE: 63

Val Ile Trp Ser Asp Gly Ser Thr Asp Phe Asn Ala Pro Phe Lys Ser
1               5                   10                  15

<210> SEQ ID NO 64
<211> LENGTH: 16
<212> TYPE: PRT
<213> ORGANISM: Mus sp.

<400> SEQUENCE: 64

Val Ile Trp Ser Asp Gly Ser Thr Asp Tyr Asn Ala Pro Phe Lys Ser
1               5                   10                  15

<210> SEQ ID NO 65
<211> LENGTH: 16
<212> TYPE: PRT
<213> ORGANISM: Mus sp.

<400> SEQUENCE: 65

Val Ile Trp Pro Val Gly Ser Thr Asn Tyr Asn Ser Ala Leu Met Ser
1               5                   10                  15

<210> SEQ ID NO 66
<211> LENGTH: 17
<212> TYPE: PRT
<213> ORGANISM: Mus sp.
```

-continued

<400> SEQUENCE: 66

Arg Ile Asp Pro Ala Asn Gly Asn Thr Lys Tyr Asp Pro Arg Phe Gln
1               5                   10                  15

Asp

<210> SEQ ID NO 67
<211> LENGTH: 10
<212> TYPE: PRT
<213> ORGANISM: Mus sp.

<400> SEQUENCE: 67

Val Tyr Phe Gly Asn Pro Trp Phe Ala Tyr
1               5                   10

<210> SEQ ID NO 68
<211> LENGTH: 16
<212> TYPE: PRT
<213> ORGANISM: Mus sp.

<400> SEQUENCE: 68

Thr Lys Asn Phe Tyr Ser Ser Tyr Ser Tyr Asp Asp Ala Met Asp Tyr
1               5                   10                  15

<210> SEQ ID NO 69
<211> LENGTH: 15
<212> TYPE: PRT
<213> ORGANISM: Mus sp.

<400> SEQUENCE: 69

Ser Phe Pro Asn Asn Tyr Tyr Ser Tyr Asp Asp Ala Phe Ala Tyr
1               5                   10                  15

<210> SEQ ID NO 70
<211> LENGTH: 10
<212> TYPE: PRT
<213> ORGANISM: Mus sp.

<400> SEQUENCE: 70

Gln Ile Tyr Tyr Ser Thr Leu Val Asp Tyr
1               5                   10

<210> SEQ ID NO 71
<211> LENGTH: 12
<212> TYPE: PRT
<213> ORGANISM: Mus sp.

<400> SEQUENCE: 71

Gly Thr Gly Thr Gly Phe Tyr Tyr Ala Met Asp Tyr
1               5                   10

<210> SEQ ID NO 72
<211> LENGTH: 10
<212> TYPE: PRT
<213> ORGANISM: Mus sp.

<400> SEQUENCE: 72

Val Phe Tyr Gly Glu Pro Tyr Phe Pro Tyr
1               5                   10

<210> SEQ ID NO 73
<211> LENGTH: 11
<212> TYPE: PRT
<213> ORGANISM: Mus sp.

-continued

<400> SEQUENCE: 73

Lys Gly Gly Tyr Ser Gly Ser Trp Phe Ala Tyr
1               5                   10

<210> SEQ ID NO 74
<211> LENGTH: 9
<212> TYPE: PRT
<213> ORGANISM: Mus sp.

<400> SEQUENCE: 74

Met Asp Trp Asp Asp Phe Phe Asp Tyr
1               5

<210> SEQ ID NO 75
<211> LENGTH: 15
<212> TYPE: PRT
<213> ORGANISM: Mus sp.

<400> SEQUENCE: 75

Ser Phe Pro Asp Asn Tyr Tyr Ser Tyr Asp Asp Ala Phe Ala Tyr
1               5                   10                  15

<210> SEQ ID NO 76
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

Glu Ile Val Leu Thr Gln Ser Pro Gly Thr Leu Ser Leu Ser Pro Gly
1               5                   10                  15

Glu Arg Ala Thr Met Ser Cys Thr Ala Ser Ser Ser Val Ser Ser Ser
            20                  25                  30

Tyr Phe His Trp Tyr Gln Gln Lys Pro Gly Gln Ala Pro Arg Leu Leu
        35                  40                  45

Ile Tyr Arg Thr Ser Thr Leu Ala Ser Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Ala Ala Thr Tyr Tyr Cys His Gln Phe His Arg Ser Pro
                85                  90                  95

Leu Thr Phe Gly Gln Gly Thr Lys Leu Glu Ile Lys
            100                 105

<210> SEQ ID NO 77
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 77

Glu Ile Val Leu Thr Gln Ser Pro Gly Thr Leu Ser Leu Ser Pro Gly
1               5                   10                  15

Glu Arg Ala Thr Met Ser Cys Thr Ala Ser Ser Ser Val Ser Ser Ser
            20                  25                  30

Tyr Phe His Trp Tyr Gln Gln Lys Pro Gly Gln Ala Pro Arg Leu Leu
        35                  40                  45

```
Ile Tyr Arg Thr Ser Ile Leu Ala Ser Gly Val Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Thr Tyr Tyr Cys His Gln Phe His Arg Ser Pro
                85                  90                  95

Leu Thr Phe Gly Gln Gly Thr Lys Leu Glu Ile Lys
                100                 105

<210> SEQ ID NO 78
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 78

Glu Ile Val Leu Thr Gln Ser Pro Gly Thr Leu Ser Leu Ser Pro Gly
1               5                   10                  15

Glu Arg Ala Thr Met Ser Cys Thr Ala Ser Ser Ser Val Ser Ser Ser
                20                  25                  30

Tyr Phe His Trp Tyr Gln Gln Lys Pro Gly Gln Ala Pro Arg Leu Trp
            35                  40                  45

Ile Tyr Arg Thr Ser Arg Leu Ala Ser Gly Val Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Ala Ala Thr Tyr Tyr Cys His Gln Phe His Arg Ser Pro
                85                  90                  95

Leu Thr Phe Gly Gln Gly Thr Lys Leu Glu Ile Lys
                100                 105

<210> SEQ ID NO 79
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 79

Glu Ile Val Leu Thr Gln Ser Pro Gly Thr Leu Ser Leu Ser Pro Gly
1               5                   10                  15

Glu Arg Ala Thr Met Thr Cys Thr Ala Ser Ser Ser Val Ser Ser Ser
                20                  25                  30

Tyr Phe His Trp Tyr Gln Gln Lys Pro Gly Gln Ala Pro Arg Leu Leu
            35                  40                  45

Ile Tyr Arg Thr Ser Arg Leu Ala Ser Gly Val Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys His Gln Phe His Arg Ser Pro
                85                  90                  95

Leu Thr Phe Gly Gln Gly Thr Lys Leu Glu Ile Lys
                100                 105

<210> SEQ ID NO 80
```

-continued

```
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 80

Gln Ile Val Leu Thr Gln Ser Pro Gly Thr Leu Ser Leu Ser Pro Gly
1               5                   10                  15

Glu Arg Ala Thr Met Thr Cys Thr Ala Ser Ser Ser Val Ser Ser Ser
            20                  25                  30

Tyr Phe His Trp Tyr Gln Gln Lys Pro Gly Gln Ala Pro Arg Leu Trp
        35                  40                  45

Ile Tyr Arg Thr Ser Arg Leu Ala Ser Gly Val Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Ala Ala Thr Tyr Tyr Cys His Gln Phe His Arg Ser Pro
                85                  90                  95

Leu Thr Phe Gly Ala Gly Thr Lys Leu Glu Ile Lys
            100                 105

<210> SEQ ID NO 81
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 81

Gln Ile Val Leu Thr Gln Ser Pro Gly Thr Leu Ser Leu Ser Pro Gly
1               5                   10                  15

Glu Arg Val Thr Met Ser Cys Thr Ala Ser Ser Ser Val Ser Ser Ser
            20                  25                  30

Tyr Phe His Trp Tyr Gln Gln Lys Pro Gly Gln Ala Pro Arg Leu Leu
        35                  40                  45

Ile Tyr Arg Thr Ser Gln Leu Ala Ser Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Ala Ala Thr Tyr Tyr Cys His Gln Phe His Arg Ser Pro
                85                  90                  95

Leu Thr Phe Gly Gln Gly Thr Lys Leu Glu Ile Lys
            100                 105

<210> SEQ ID NO 82
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 82

Gln Ile Val Leu Thr Gln Ser Pro Gly Thr Leu Ser Leu Ser Pro Gly
1               5                   10                  15

Glu Arg Ala Thr Met Thr Cys Thr Ala Ser Ser Ser Val Ser Ser Ser
            20                  25                  30
```

```
Tyr Phe His Trp Tyr Gln Gln Lys Pro Gly Gln Ala Pro Arg Leu Leu
        35              40              45

Ile Tyr Arg Thr Ser Lys Leu Ala Ser Gly Val Pro Asp Arg Phe Ser
    50              55              60

Gly Ser Gly Ser Gly Thr Asp Phe Thr Leu Thr Ile Ser Arg Leu Glu
65              70              75              80

Pro Glu Asp Phe Ala Thr Tyr Tyr Cys His Gln Phe His Arg Ser Pro
                85              90              95

Leu Thr Phe Gly Gln Gly Thr Lys Leu Glu Ile Lys
        100             105
```

```
<210> SEQ ID NO 83
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 83

Glu Ile Val Leu Thr Gln Ser Pro Gly Thr Leu Ser Leu Ser Pro Gly
1               5               10              15

Glu Arg Ala Thr Met Ser Cys Thr Ala Ser Ser Ser Val Ser Ser Ser
            20              25              30

Tyr Phe His Trp Tyr Gln Gln Lys Pro Gly Gln Ala Pro Arg Leu Leu
        35              40              45

Ile Tyr Arg Thr Ser His Leu Ala Ser Gly Ile Pro Gly Arg Phe Ser
    50              55              60

Gly Ser Gly Ser Gly Thr Asp Phe Thr Leu Thr Ile Ser Arg Leu Glu
65              70              75              80

Pro Glu Asp Ala Ala Val Tyr Tyr Cys His Gln Phe His Arg Ser Pro
                85              90              95

Leu Thr Phe Gly Gln Gly Thr Lys Leu Glu Ile Lys
        100             105
```

```
<210> SEQ ID NO 84
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 84

Glu Ile Val Met Thr Gln Ser Pro Ala Thr Leu Ser Val Ser Pro Gly
1               5               10              15

Val Arg Ala Thr Leu Ser Cys Lys Ala Ser Gln Asp Val Gly Thr Asn
            20              25              30

Val Leu Trp Tyr Gln Gln Lys Pro Gly Gln Ala Pro Arg Pro Leu Ile
        35              40              45

Tyr Ser Ala Ser Tyr Arg His Ser Gly Ile Pro Asp Arg Phe Ser Gly
    50              55              60

Ser Gly Ser Gly Thr Glu Phe Thr Leu Thr Ile Ser Ser Leu Gln Ser
65              70              75              80

Glu Asp Phe Ala Glu Tyr Phe Cys Gln Gln Tyr Ser Arg Tyr Pro Leu
                85              90              95

Thr Phe Gly Gln Gly Thr Lys Leu Glu Ile Lys
        100             105
```

-continued

<210> SEQ ID NO 85
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 85

Glu Ile Val Met Thr Gln Ser Pro Ala Thr Leu Ser Val Ser Pro Gly
1               5                   10                  15

Val Arg Ala Thr Leu Ser Cys Lys Ala Ser Gln Asp Val Gly Thr Asn
            20                  25                  30

Val Leu Trp Tyr Gln Gln Lys Pro Gly Gln Ala Pro Arg Pro Leu Ile
        35                  40                  45

Tyr Ser Ala Ser Tyr Arg His Ser Gly Ile Pro Asp Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Ser Arg Tyr Pro Leu
                85                  90                  95

Thr Phe Gly Gln Gly Thr Lys Leu Glu Ile Lys
            100                 105

<210> SEQ ID NO 86
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 86

Glu Ile Val Met Thr Gln Ser Pro Ala Thr Leu Ser Val Ser Pro Gly
1               5                   10                  15

Val Arg Ala Thr Leu Ser Cys Lys Ala Ser Gln Asp Val Gly Thr Asn
            20                  25                  30

Val Leu Trp Tyr Gln Gln Lys Pro Gly Gln Ala Pro Arg Pro Leu Ile
        35                  40                  45

Tyr Ser Ala Ser Tyr Arg His Ser Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Glu Tyr Tyr Cys Gln Gln Tyr Ser Arg Tyr Pro Leu
                85                  90                  95

Thr Phe Gly Gln Gly Thr Lys Leu Glu Ile Lys
            100                 105

<210> SEQ ID NO 87
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 87

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Ser Ser

-continued

```
               20              25              30

Trp Ile His Trp Val Arg Gln Ala Pro Gly Gln Gly Leu Glu Trp Ile
           35              40              45

Gly Glu Ile Asn Pro Gly Asn Val Arg Thr Asn Tyr Asn Glu Asn Phe
       50              55              60

Arg Asn Lys Ala Thr Met Thr Val Asp Thr Ser Ile Ser Thr Ala Tyr
65              70              75              80

Met Glu Leu Ser Arg Leu Arg Ser Asp Asp Thr Ala Val Tyr Tyr Cys
               85              90              95

Ala Val Val Phe Tyr Gly Glu Pro Tyr Phe Pro Tyr Trp Gly Gln Gly
              100             105             110

Thr Leu Val Thr Val Ser Ser
           115
```

```
<210> SEQ ID NO 88
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 88

Gln Val Gln Leu Val Gln Ser Gly Ala Glu Val Lys Lys Pro Gly Ala
1               5               10              15

Ser Val Lys Val Ser Cys Lys Ala Ser Gly Tyr Ser Phe Thr Ser Ser
               20              25              30

Trp Ile His Trp Val Arg Gln Arg Pro Gly Gln Gly Leu Glu Trp Ile
           35              40              45

Gly Glu Ile Asn Pro Gly Asn Val Arg Thr Asn Tyr Asn Glu Asn Phe
       50              55              60

Arg Asn Arg Val Thr Met Thr Val Asp Thr Ser Ile Ser Thr Ala Tyr
65              70              75              80

Met Glu Leu Ser Arg Leu Arg Ser Asp Asp Thr Ala Val Tyr Tyr Cys
               85              90              95

Thr Val Val Phe Tyr Gly Glu Pro Tyr Phe Pro Tyr Trp Gly Gln Gly
              100             105             110

Thr Leu Val Thr Val Ser Ser
           115
```

```
<210> SEQ ID NO 89
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 89

Gln Val Gln Leu Val Gln Ser Gly Ala Glu Val Lys Lys Pro Gly Ala
1               5               10              15

Ser Val Lys Val Ser Cys Lys Ala Ser Gly Tyr Ser Phe Thr Ser Ser
               20              25              30

Trp Ile His Trp Val Lys Gln Ala Pro Gly Gln Gly Leu Glu Trp Met
           35              40              45

Gly Glu Ile Asn Pro Gly Asn Val Arg Thr Asn Tyr Asn Glu Asn Phe
       50              55              60

Arg Asn Lys Val Thr Met Thr Val Asp Thr Ser Ile Ser Thr Ala Tyr
```

-continued

```
65                  70                  75                  80

Met Glu Leu Ser Arg Leu Arg Ser Asp Asp Thr Ala Val Tyr Tyr Cys
                85                  90                  95

Thr Val Val Phe Tyr Gly Glu Pro Tyr Phe Pro Tyr Trp Gly Gln Gly
            100                 105                 110

Thr Leu Val Thr Val Ser Ser
        115

<210> SEQ ID NO 90
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 90

Gln Val Gln Leu Val Gln Ser Gly Ala Glu Val Lys Lys Pro Gly Ala
1                   5                   10                  15

Ser Val Lys Val Ser Cys Lys Ala Ser Gly Tyr Ser Phe Thr Ser Ser
                20                  25                  30

Trp Ile His Trp Val Arg Gln Arg Pro Gly Gln Gly Leu Glu Trp Met
            35                  40                  45

Gly Glu Ile Asn Pro Gly Asn Val Arg Thr Asn Tyr Asn Glu Asn Phe
        50                  55                  60

Arg Asn Arg Ala Thr Leu Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Val Val Phe Tyr Gly Glu Pro Tyr Phe Pro Tyr Trp Gly Gln Gly
            100                 105                 110

Thr Leu Val Thr Val Ser Ser
        115

<210> SEQ ID NO 91
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 91

Gln Val Gln Leu Val Gln Ser Gly Ala Glu Val Lys Lys Pro Gly Ala
1                   5                   10                  15

Ser Val Lys Val Ser Cys Lys Ala Ser Gly Tyr Ser Phe Thr Ser Ser
                20                  25                  30

Trp Ile His Trp Val Arg Gln Arg Pro Gly Gln Gly Leu Glu Trp Met
            35                  40                  45

Gly Glu Ile Leu Pro Gly Val Val Arg Thr Asn Tyr Asn Glu Asn Phe
        50                  55                  60

Arg Asn Lys Val Thr Met Thr Val Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Thr Val Val Phe Tyr Gly Glu Pro Tyr Phe Pro Tyr Trp Gly Gln Gly
            100                 105                 110

Thr Leu Val Thr Val Ser Ser
```

-continued

```
                    115

<210> SEQ ID NO 92
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 92

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Ser Ser
                20                  25                  30

Trp Ile His Trp Val Arg Gln Arg Pro Gly Gln Gly Leu Glu Trp Ile
            35                  40                  45

Gly Glu Ile Asn Pro Gly Ala Val Arg Thr Asn Tyr Asn Glu Asn Phe
        50                  55                  60

Arg Asn Arg Val Thr Met Thr Val Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Thr Val Val Phe Tyr Gly Glu Pro Tyr Phe Pro Tyr Trp Gly Gln Gly
            100                 105                 110

Thr Leu Val Thr Val Ser Ser
        115

<210> SEQ ID NO 93
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 93

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Ser Ser
                20                  25                  30

Trp Ile His Trp Val Arg Gln Ala Pro Gly Gln Gly Leu Glu Trp Ile
            35                  40                  45

Gly Glu Ile Asn Pro Gly Leu Val Arg Thr Asn Tyr Asn Glu Asn Phe
        50                  55                  60

Arg Asn Lys Val Thr Met Thr Val Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Val Val Phe Tyr Gly Glu Pro Tyr Phe Pro Tyr Trp Gly Gln Gly
            100                 105                 110

Thr Leu Val Thr Val Ser Ser
        115

<210> SEQ ID NO 94
<211> LENGTH: 119
<212> TYPE: PRT
<213> ORGANISM: Artificial Sequence
<220> FEATURE:
<223> OTHER INFORMATION: Description of Artificial Sequence: Synthetic
```

-continued

```
        polypeptide

<400> SEQUENCE: 94

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Ser Ser
            20                  25                  30

Trp Ile His Trp Val Arg Gln Ala Pro Gly Gln Gly Leu Glu Trp Ile
        35                  40                  45

Gly Glu Ile Asn Pro Gly Ala Val Arg Thr Asn Tyr Asn Glu Asn Phe
    50                  55                  60

Arg Asn Lys Val Thr Met Thr Val Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Val Val Phe Tyr Gly Glu Pro Tyr Phe Pro Tyr Trp Gly Gln Gly
            100                 105                 110

Thr Leu Val Thr Val Ser Ser
        115

<210> SEQ ID NO 95
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 95

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Ser Ser
            20                  25                  30

Trp Ile His Trp Val Arg Gln Ala Pro Gly Gln Gly Leu Glu Trp Ile
        35                  40                  45

Gly Glu Ile Asn Pro Gly Ser Val Arg Thr Asn Tyr Asn Glu Asn Phe
    50                  55                  60

Arg Asn Lys Ala Thr Met Thr Val Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Val Val Phe Tyr Gly Glu Pro Tyr Phe Pro Tyr Trp Gly Gln Gly
            100                 105                 110

Thr Leu Val Thr Val Ser Ser
        115

<210> SEQ ID NO 96
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 96

Gln Val Gln Leu Gln Glu Ser Gly Pro Gly Leu Val Lys Pro Ser Glu
1               5                   10                  15

Thr Leu Ser Ile Thr Cys Thr Val Ser Gly Phe Ser Leu Thr Asp Tyr
            20                  25                  30
```

-continued

```
Ala Val His Trp Ile Arg Gln Pro Pro Gly Lys Gly Leu Glu Trp Ile
        35                  40                  45

Gly Val Ile Trp Ser Asp Gly Ser Thr Asp Tyr Asn Ala Pro Phe Lys
    50                  55                  60

Ser Arg Val Thr Ile Asn Lys Asp Thr Ser Lys Ser Gln Val Ser Phe
65                  70                  75                  80

Lys Met Ser Ser Val Gln Ala Ala Asp Thr Ala Val Tyr Tyr Cys Ala
                85                  90                  95

Arg Lys Gly Gly Tyr Ser Gly Ser Trp Phe Ala Tyr Trp Gly Gln Gly
                100                 105                 110

Thr Leu Val Thr Val Ser Ser
        115

<210> SEQ ID NO 97
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 97

Gln Val Gln Leu Gln Glu Ser Gly Pro Gly Leu Val Lys Pro Ser Glu
1               5                   10                  15

Thr Leu Ser Ile Thr Cys Thr Val Ser Gly Phe Ser Leu Thr Asp Tyr
                20                  25                  30

Ala Val His Trp Ile Arg Gln Pro Pro Gly Lys Gly Leu Glu Trp Ile
        35                  40                  45

Gly Val Ile Trp Ser Asp Gly Ser Thr Asp Tyr Asn Ala Pro Phe Lys
    50                  55                  60

Ser Arg Val Thr Ile Ser Lys Asp Thr Ser Lys Asn Gln Val Ser Leu
65                  70                  75                  80

Lys Met Asn Ser Leu Thr Thr Asp Asp Thr Ala Val Tyr Tyr Cys Ala
                85                  90                  95

Arg Lys Gly Gly Tyr Ser Gly Ser Trp Phe Ala Tyr Trp Gly Gln Gly
                100                 105                 110

Thr Leu Val Thr Val Ser Ser
        115

<210> SEQ ID NO 98
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 98

Gln Val Gln Leu Gln Glu Ser Gly Pro Gly Leu Val Lys Pro Ser Glu
1               5                   10                  15

Thr Leu Ser Ile Thr Cys Thr Val Ser Gly Phe Ser Leu Thr Asp Tyr
                20                  25                  30

Ala Val His Trp Ile Arg Gln Pro Pro Gly Lys Gly Leu Glu Trp Ile
        35                  40                  45

Gly Val Ile Trp Ser Asp Gly Ser Thr Asp Tyr Asn Ala Pro Phe Lys
    50                  55                  60

Ser Arg Val Thr Ile Ser Lys Asp Asn Ser Lys Ser Gln Val Ser Leu
65                  70                  75                  80
```

```
Lys Met Asn Ser Val Thr Val Ala Asp Thr Ala Val Tyr Tyr Cys Ala
                85                  90                  95

Arg Lys Gly Gly Tyr Ser Gly Ser Trp Phe Ala Tyr Trp Gly Gln Gly
            100                 105                 110

Thr Leu Val Thr Val Ser Ser
        115

<210> SEQ ID NO 99
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 99

Gln Val Gln Leu Gln Glu Ser Gly Pro Gly Leu Val Lys Pro Ser Glu
1               5                   10                  15

Thr Leu Ser Ile Thr Cys Thr Val Ser Gly Phe Ser Leu Thr Asp Tyr
                20                  25                  30

Ala Val His Trp Val Arg Gln Pro Pro Gly Lys Gly Leu Glu Trp Ile
            35                  40                  45

Gly Val Ile Trp Ser Asp Gly Ser Thr Asp Tyr Asn Ala Pro Phe Lys
        50                  55                  60

Ser Arg Val Thr Ile Ser Lys Asp Thr Ser Lys Asn Gln Val Ser Phe
65                  70                  75                  80

Lys Leu Ser Ser Val Thr Val Asp Asp Thr Ala Val Tyr Tyr Cys Ala
                85                  90                  95

Arg Lys Gly Gly Tyr Ser Gly Ser Trp Phe Ala Tyr Trp Gly Gln Gly
            100                 105                 110

Thr Leu Val Thr Val Ser Ser
        115

<210> SEQ ID NO 100
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 100

Gln Val Gln Leu Gln Glu Ser Gly Pro Gly Leu Val Ala Pro Ser Glu
1               5                   10                  15

Thr Leu Ser Leu Thr Cys Thr Val Ser Gly Phe Ser Leu Thr Asp Tyr
                20                  25                  30

Ala Val His Trp Ile Arg Gln Phe Pro Gly Lys Gly Leu Glu Trp Ile
            35                  40                  45

Gly Val Ile Trp Ser Asp Gly Ser Thr Asp Phe Asn Ala Pro Phe Lys
        50                  55                  60

Ser Arg Val Thr Ile Ser Lys Asp Thr Ser Lys Asn Gln Val Ser Phe
65                  70                  75                  80

Lys Leu Ser Ser Val Thr Thr Asp Asp Thr Ala Val Tyr Tyr Cys Ala
                85                  90                  95

Arg Lys Gly Gly Tyr Ser Gly Ser Trp Phe Ala Tyr Trp Gly Gln Gly
            100                 105                 110

Thr Leu Val Thr Val Ser Ser
        115
```

```
<210> SEQ ID NO 101
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 101

Gln Val Gln Leu Gln Glu Ser Gly Pro Gly Leu Val Lys Pro Ser Glu
1               5                   10                  15

Thr Leu Ser Ile Thr Cys Thr Val Ser Gly Phe Ser Leu Thr Asp Tyr
            20                  25                  30

Ala Val His Trp Ile Arg Gln Pro Pro Gly Lys Gly Leu Glu Trp Ile
        35                  40                  45

Gly Val Ile Trp Ser Asp Gly Ser Thr Asp Tyr Asn Ala Pro Phe Lys
    50                  55                  60

Ser Arg Val Thr Ile Ser Lys Asp Asn Ser Lys Ser Gln Val Ser Phe
65                  70                  75                  80

Lys Met Ser Ser Val Thr Ala Asp Asp Thr Ala Val Tyr Tyr Cys Ala
                85                  90                  95

Arg Lys Gly Gly Tyr Ser Gly Ser Trp Phe Ala Tyr Trp Gly Gln Gly
            100                 105                 110

Thr Leu Val Thr Val Ser Ser
        115

<210> SEQ ID NO 102
<211> LENGTH: 7
<212> TYPE: PRT
<213> ORGANISM: Mus sp.

<400> SEQUENCE: 102

Arg Thr Ser Thr Leu Ala Ser
1               5

<210> SEQ ID NO 103
<211> LENGTH: 7
<212> TYPE: PRT
<213> ORGANISM: Mus sp.

<400> SEQUENCE: 103

Arg Thr Ser Ile Leu Ala Ser
1               5

<210> SEQ ID NO 104
<211> LENGTH: 7
<212> TYPE: PRT
<213> ORGANISM: Mus sp.

<400> SEQUENCE: 104

Arg Thr Ser Arg Leu Ala Ser
1               5

<210> SEQ ID NO 105
<211> LENGTH: 7
<212> TYPE: PRT
<213> ORGANISM: Mus sp.

<400> SEQUENCE: 105

Arg Thr Ser Gln Leu Ala Ser
1               5
```

-continued

```
<210> SEQ ID NO 106
<211> LENGTH: 7
<212> TYPE: PRT
<213> ORGANISM: Mus sp.

<400> SEQUENCE: 106

Arg Thr Ser Lys Leu Ala Ser
1               5

<210> SEQ ID NO 107
<211> LENGTH: 10
<212> TYPE: PRT
<213> ORGANISM: Mus sp.

<400> SEQUENCE: 107

Gly Phe Ser Leu Thr Asp Tyr Ala Val His
1               5                   10

<210> SEQ ID NO 108
<211> LENGTH: 15
<212> TYPE: PRT
<213> ORGANISM: Mus sp.

<400> SEQUENCE: 108

Glu Ile Leu Pro Gly Val Val Arg Thr Asn Tyr Asn Glu Asn Phe
1               5                   10                  15

<210> SEQ ID NO 109
<211> LENGTH: 15
<212> TYPE: PRT
<213> ORGANISM: Mus sp.

<400> SEQUENCE: 109

Glu Ile Asn Pro Gly Ala Val Arg Thr Asn Tyr Asn Glu Asn Phe
1               5                   10                  15

<210> SEQ ID NO 110
<211> LENGTH: 15
<212> TYPE: PRT
<213> ORGANISM: Mus sp.

<400> SEQUENCE: 110

Glu Ile Asn Pro Gly Leu Val Arg Thr Asn Tyr Asn Glu Asn Phe
1               5                   10                  15

<210> SEQ ID NO 111
<211> LENGTH: 15
<212> TYPE: PRT
<213> ORGANISM: Mus sp.

<400> SEQUENCE: 111

Glu Ile Asn Pro Gly Ser Val Arg Thr Asn Tyr Asn Glu Asn Phe
1               5                   10                  15

<210> SEQ ID NO 112
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 112

Ala Ser Thr Lys Gly Pro Ser Val Phe Pro Leu Ala Pro Ser Ser Lys
```

-continued

```
1               5                    10                   15

Ser Thr Ser Gly Gly Thr Ala Ala Leu Gly Cys Leu Val Lys Asp Tyr
            20              25              30

Phe Pro Glu Pro Val Thr Val Ser Trp Asn Ser Gly Ala Leu Thr Ser
            35              40              45

Gly Val His Thr Phe Pro Ala Val Leu Gln Ser Ser Gly Leu Tyr Ser
    50              55              60

Leu Ser Ser Val Val Thr Val Pro Ser Ser Ser Leu Gly Thr Gln Thr
65              70              75              80

Tyr Ile Cys Asn Val Asn His Lys Pro Ser Asn Thr Lys Val Asp Lys
                85              90              95

Arg Val Glu Pro Lys Ser Cys Asp Lys Thr His Thr Cys Pro Pro Cys
            100             105             110

Pro Ala Pro Glu Ala Ala Gly Gly Pro Ser Val Phe Leu Phe Pro Pro
            115             120             125

Lys Pro Lys Asp Thr Leu Met Ile Ser Arg Thr Pro Glu Val Thr Cys
    130             135             140

Val Val Val Asp Val Ser His Glu Asp Pro Glu Val Lys Phe Asn Trp
145             150             155             160

Tyr Val Asp Gly Val Glu Val His Asn Ala Lys Thr Lys Pro Arg Glu
                165             170             175

Glu Gln Tyr Asn Ser Thr Tyr Arg Val Val Ser Val Leu Thr Val Leu
            180             185             190

His Gln Asp Trp Leu Asn Gly Lys Glu Tyr Lys Cys Lys Val Ser Asn
            195             200             205

Lys Ala Leu Pro Ala Pro Ile Glu Lys Thr Ile Ser Lys Ala Lys Gly
    210             215             220

Gln Pro Arg Glu Pro Gln Val Tyr Thr Leu Pro Pro Ser Arg Glu Glu
225             230             235             240

Met Thr Lys Asn Gln Val Ser Leu Thr Cys Leu Val Lys Gly Phe Tyr
                245             250             255

Pro Ser Asp Ile Ala Val Glu Trp Glu Ser Asn Gly Gln Pro Glu Asn
            260             265             270

Asn Tyr Lys Thr Thr Pro Pro Val Leu Asp Ser Asp Gly Ser Phe Phe
            275             280             285

Leu Tyr Ser Lys Leu Thr Val Asp Lys Ser Arg Trp Gln Gln Gly Asn
    290             295             300

Val Phe Ser Cys Ser Val Met His Glu Ala Leu His Asn His Tyr Thr
305             310             315             320

Gln Lys Ser Leu Ser Leu Ser Pro Gly Lys
            325             330
```

```
<210> SEQ ID NO 113
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 113

Arg Thr Val Ala Ala Pro Ser Val Phe Ile Phe Pro Pro Ser Asp Glu
1               5                    10                   15

Gln Leu Lys Ser Gly Thr Ala Ser Val Val Cys Leu Leu Asn Asn Phe
            20              25              30
```

```
Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
        50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```

<210> SEQ ID NO 114
<211> LENGTH: 215
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 114

```
Glu Ile Val Leu Thr Gln Ser Pro Gly Thr Leu Ser Leu Ser Pro Gly
1               5                   10                  15

Glu Arg Ala Thr Met Ser Cys Thr Ala Ser Ser Ser Val Ser Ser Ser
                20                  25                  30

Tyr Phe His Trp Tyr Gln Gln Lys Pro Gly Gln Ala Pro Arg Leu Leu
            35                  40                  45

Ile Tyr Arg Thr Ser Thr Leu Ala Ser Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Ala Ala Thr Tyr Tyr Cys His Gln Phe His Arg Ser Pro
                85                  90                  95

Leu Thr Phe Gly Gln Gly Thr Lys Leu Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
        130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215
```

<210> SEQ ID NO 115
<211> LENGTH: 215
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 115

-continued

```
Glu Ile Val Leu Thr Gln Ser Pro Gly Thr Leu Ser Leu Ser Pro Gly
1               5                   10                  15

Glu Arg Ala Thr Met Ser Cys Thr Ala Ser Ser Ser Val Ser Ser Ser
            20                  25                  30

Tyr Phe His Trp Tyr Gln Gln Lys Pro Gly Gln Ala Pro Arg Leu Leu
        35                  40                  45

Ile Tyr Arg Thr Ser Ile Leu Ala Ser Gly Val Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Thr Tyr Tyr Cys His Gln Phe His Arg Ser Pro
                85                  90                  95

Leu Thr Phe Gly Gln Gly Thr Lys Leu Glu Ile Lys Arg Thr Val Ala
            100                 105                 110

Ala Pro Ser Val Phe Ile Phe Pro Pro Ser Asp Glu Gln Leu Lys Ser
            115                 120                 125

Gly Thr Ala Ser Val Val Cys Leu Leu Asn Asn Phe Tyr Pro Arg Glu
        130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
            165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
            195                 200                 205

Ser Phe Asn Arg Gly Glu Cys
    210                 215

<210> SEQ ID NO 116
<211> LENGTH: 215
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 116

Glu Ile Val Leu Thr Gln Ser Pro Gly Thr Leu Ser Leu Ser Pro Gly
1               5                   10                  15

Glu Arg Ala Thr Met Ser Cys Thr Ala Ser Ser Ser Val Ser Ser Ser
            20                  25                  30

Tyr Phe His Trp Tyr Gln Gln Lys Pro Gly Gln Ala Pro Arg Leu Trp
        35                  40                  45

Ile Tyr Arg Thr Ser Arg Leu Ala Ser Gly Val Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Ala Ala Thr Tyr Tyr Cys His Gln Phe His Arg Ser Pro
                85                  90                  95

Leu Thr Phe Gly Gln Gly Thr Lys Leu Glu Ile Lys Arg Thr Val Ala
            100                 105                 110

Ala Pro Ser Val Phe Ile Phe Pro Pro Ser Asp Glu Gln Leu Lys Ser
            115                 120                 125

Gly Thr Ala Ser Val Val Cys Leu Leu Asn Asn Phe Tyr Pro Arg Glu
        130                 135                 140
```

-continued

```
Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 117
<211> LENGTH: 215
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 117

Glu Ile Val Leu Thr Gln Ser Pro Gly Thr Leu Ser Leu Ser Pro Gly
1               5                   10                  15

Glu Arg Ala Thr Met Thr Cys Thr Ala Ser Ser Ser Val Ser Ser Ser
                20                  25                  30

Tyr Phe His Trp Tyr Gln Gln Lys Pro Gly Gln Ala Pro Arg Leu Leu
            35                  40                  45

Ile Tyr Arg Thr Ser Arg Leu Ala Ser Gly Val Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys His Gln Phe His Arg Ser Pro
                85                  90                  95

Leu Thr Phe Gly Gln Gly Thr Lys Leu Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 118
<211> LENGTH: 215
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 118
```

-continued

```
Gln Ile Val Leu Thr Gln Ser Pro Gly Thr Leu Ser Leu Ser Pro Gly
1               5                  10                 15

Glu Arg Ala Thr Met Thr Cys Thr Ala Ser Ser Ser Val Ser Ser Ser
            20                  25                 30

Tyr Phe His Trp Tyr Gln Gln Lys Pro Gly Gln Ala Pro Arg Leu Trp
        35                  40                 45

Ile Tyr Arg Thr Ser Arg Leu Ala Ser Gly Val Pro Asp Arg Phe Ser
    50                  55                 60

Gly Ser Gly Ser Gly Thr Asp Phe Thr Leu Thr Ile Ser Arg Leu Glu
65                  70                 75                 80

Pro Glu Asp Ala Ala Thr Tyr Tyr Cys His Gln Phe His Arg Ser Pro
                85                  90                 95

Leu Thr Phe Gly Ala Gly Thr Lys Leu Glu Ile Lys Arg Thr Val Ala
            100                 105                110

Ala Pro Ser Val Phe Ile Phe Pro Pro Ser Asp Glu Gln Leu Lys Ser
        115                 120                125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                160

Gln Glu Ser Val Thr Glu Gln Asp Ser Lys Asp Ser Thr Tyr Ser Leu
            165                 170                175

Ser Ser Thr Leu Thr Leu Ser Lys Ala Asp Tyr Glu Lys His Lys Val
            180                 185                190

Tyr Ala Cys Glu Val Thr His Gln Gly Leu Ser Ser Pro Val Thr Lys
        195                 200                205

Ser Phe Asn Arg Gly Glu Cys
    210                 215
```

```
<210> SEQ ID NO 119
<211> LENGTH: 215
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 119
```

```
Gln Ile Val Leu Thr Gln Ser Pro Gly Thr Leu Ser Leu Ser Pro Gly
1               5                  10                 15

Glu Arg Val Thr Met Ser Cys Thr Ala Ser Ser Ser Val Ser Ser Ser
            20                  25                 30

Tyr Phe His Trp Tyr Gln Gln Lys Pro Gly Gln Ala Pro Arg Leu Leu
        35                  40                 45

Ile Tyr Arg Thr Ser Gln Leu Ala Ser Gly Ile Pro Asp Arg Phe Ser
    50                  55                 60

Gly Ser Gly Ser Gly Thr Asp Phe Thr Leu Thr Ile Ser Arg Leu Glu
65                  70                 75                 80

Pro Glu Asp Ala Ala Thr Tyr Tyr Cys His Gln Phe His Arg Ser Pro
                85                  90                 95

Leu Thr Phe Gly Gln Gly Thr Lys Leu Glu Ile Lys Arg Thr Val Ala
            100                 105                110

Ala Pro Ser Val Phe Ile Phe Pro Pro Ser Asp Glu Gln Leu Lys Ser
        115                 120                125

Gly Thr Ala Ser Val Val Cys Leu Leu Asn Asn Phe Tyr Pro Arg Glu
```

-continued

```
     130             135             140

Ala Lys Val Gln Trp Lys Val Asp Asn Ala Leu Gln Ser Gly Asn Ser
145             150             155             160

Gln Glu Ser Val Thr Glu Gln Asp Ser Lys Asp Ser Thr Tyr Ser Leu
                165             170             175

Ser Ser Thr Leu Thr Leu Ser Lys Ala Asp Tyr Glu Lys His Lys Val
            180             185             190

Tyr Ala Cys Glu Val Thr His Gln Gly Leu Ser Ser Pro Val Thr Lys
        195             200             205

Ser Phe Asn Arg Gly Glu Cys
    210             215

<210> SEQ ID NO 120
<211> LENGTH: 215
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 120

Gln Ile Val Leu Thr Gln Ser Pro Gly Thr Leu Ser Leu Ser Pro Gly
1               5               10              15

Glu Arg Ala Thr Met Thr Cys Thr Ala Ser Ser Ser Val Ser Ser Ser
            20              25              30

Tyr Phe His Trp Tyr Gln Gln Lys Pro Gly Gln Ala Pro Arg Leu Leu
        35              40              45

Ile Tyr Arg Thr Ser Lys Leu Ala Ser Gly Val Pro Asp Arg Phe Ser
    50              55              60

Gly Ser Gly Ser Gly Thr Asp Phe Thr Leu Thr Ile Ser Arg Leu Glu
65              70              75              80

Pro Glu Asp Phe Ala Thr Tyr Tyr Cys His Gln Phe His Arg Ser Pro
            85              90              95

Leu Thr Phe Gly Gln Gly Thr Lys Leu Glu Ile Lys Arg Thr Val Ala
            100             105             110

Ala Pro Ser Val Phe Ile Phe Pro Pro Ser Asp Glu Gln Leu Lys Ser
        115             120             125

Gly Thr Ala Ser Val Val Cys Leu Leu Asn Asn Phe Tyr Pro Arg Glu
    130             135             140

Ala Lys Val Gln Trp Lys Val Asp Asn Ala Leu Gln Ser Gly Asn Ser
145             150             155             160

Gln Glu Ser Val Thr Glu Gln Asp Ser Lys Asp Ser Thr Tyr Ser Leu
                165             170             175

Ser Ser Thr Leu Thr Leu Ser Lys Ala Asp Tyr Glu Lys His Lys Val
            180             185             190

Tyr Ala Cys Glu Val Thr His Gln Gly Leu Ser Ser Pro Val Thr Lys
        195             200             205

Ser Phe Asn Arg Gly Glu Cys
    210             215

<210> SEQ ID NO 121
<211> LENGTH: 215
<212> TYPE: PRT
<213> ORGANISM: Artificial Sequence
<220> FEATURE:
<223> OTHER INFORMATION: Description of Artificial Sequence: Synthetic
      polypeptide
```

-continued

```
<400> SEQUENCE: 121

Glu Ile Val Leu Thr Gln Ser Pro Gly Thr Leu Ser Leu Ser Pro Gly
1               5                   10                  15

Glu Arg Ala Thr Met Ser Cys Thr Ala Ser Ser Ser Val Ser Ser Ser
                20                  25                  30

Tyr Phe His Trp Tyr Gln Gln Lys Pro Gly Gln Ala Pro Arg Leu Leu
            35                  40                  45

Ile Tyr Arg Thr Ser His Leu Ala Ser Gly Ile Pro Gly Arg Phe Ser
        50                  55                  60

Gly Ser Gly Ser Gly Thr Asp Phe Thr Leu Thr Ile Ser Arg Leu Glu
65                  70                  75                  80

Pro Glu Asp Ala Ala Val Tyr Tyr Cys His Gln Phe His Arg Ser Pro
                85                  90                  95

Leu Thr Phe Gly Gln Gly Thr Lys Leu Glu Ile Lys Arg Thr Val Ala
                100                 105                 110

Ala Pro Ser Val Phe Ile Phe Pro Pro Ser Asp Glu Gln Leu Lys Ser
            115                 120                 125

Gly Thr Ala Ser Val Val Cys Leu Leu Asn Asn Phe Tyr Pro Arg Glu
        130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 122
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 122

Glu Ile Val Met Thr Gln Ser Pro Ala Thr Leu Ser Val Ser Pro Gly
1               5                   10                  15

Val Arg Ala Thr Leu Ser Cys Lys Ala Ser Gln Asp Val Gly Thr Asn
                20                  25                  30

Val Leu Trp Tyr Gln Gln Lys Pro Gly Gln Ala Pro Arg Pro Leu Ile
            35                  40                  45

Tyr Ser Ala Ser Tyr Arg His Ser Gly Ile Pro Asp Arg Phe Ser Gly
        50                  55                  60

Ser Gly Ser Gly Thr Glu Phe Thr Leu Thr Ile Ser Ser Leu Gln Ser
65                  70                  75                  80

Glu Asp Phe Ala Glu Tyr Phe Cys Gln Gln Tyr Ser Arg Tyr Pro Leu
                85                  90                  95

Thr Phe Gly Gln Gly Thr Lys Leu Glu Ile Lys Arg Thr Val Ala Ala
                100                 105                 110

Pro Ser Val Phe Ile Phe Pro Pro Ser Asp Glu Gln Leu Lys Ser Gly
            115                 120                 125
```

-continued

```
Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210
```

```
<210> SEQ ID NO 123
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 123

Glu Ile Val Met Thr Gln Ser Pro Ala Thr Leu Ser Val Ser Pro Gly
1               5                   10                  15

Val Arg Ala Thr Leu Ser Cys Lys Ala Ser Gln Asp Val Gly Thr Asn
            20                  25                  30

Val Leu Trp Tyr Gln Gln Lys Pro Gly Gln Ala Pro Arg Pro Leu Ile
        35                  40                  45

Tyr Ser Ala Ser Tyr Arg His Ser Gly Ile Pro Asp Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Ser Arg Tyr Pro Leu
            85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210
```

```
<210> SEQ ID NO 124
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 124

```
Glu Ile Val Met Thr Gln Ser Pro Ala Thr Leu Ser Val Ser Pro Gly
1               5                   10                  15

Val Arg Ala Thr Leu Ser Cys Lys Ala Ser Gln Asp Val Gly Thr Asn
            20                  25                  30

Val Leu Trp Tyr Gln Gln Lys Pro Gly Gln Ala Pro Arg Pro Leu Ile
        35                  40                  45

Tyr Ser Ala Ser Tyr Arg His Ser Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Glu Tyr Tyr Cys Gln Gln Tyr Ser Arg Tyr Pro Leu
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
        210
```

<210> SEQ ID NO 125
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 125

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Ser Ser
            20                  25                  30

Trp Ile His Trp Val Arg Gln Ala Pro Gly Gln Gly Leu Glu Trp Ile
        35                  40                  45

Gly Glu Ile Asn Pro Gly Asn Val Arg Thr Asn Tyr Asn Glu Asn Phe
    50                  55                  60

Arg Asn Lys Ala Thr Met Thr Val Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Val Val Phe Tyr Gly Glu Pro Tyr Phe Pro Tyr Trp Gly Gln Gly
            100                 105                 110

Thr Leu Val Thr Val Ser Ser Ala Ser Thr Lys Gly Pro Ser Val Phe
            115                 120                 125
```

-continued

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
            195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
                275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Glu Glu Met Thr Lys Asn Gln Val Ser Leu Thr
                355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
            435                 440                 445

Lys

<210> SEQ ID NO 126
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 126

Gln Val Gln Leu Val Gln Ser Gly Ala Glu Val Lys Lys Pro Gly Ala
1                 5                   10                  15

Ser Val Lys Val Ser Cys Lys Ala Ser Gly Tyr Ser Phe Thr Ser Ser
                20                  25                  30

-continued

```
Trp Ile His Trp Val Arg Gln Arg Pro Gly Gln Gly Leu Glu Trp Ile
        35                  40                  45

Gly Glu Ile Asn Pro Gly Asn Val Arg Thr Asn Tyr Asn Glu Asn Phe
        50                  55                  60

Arg Asn Arg Val Thr Met Thr Val Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Thr Val Val Phe Tyr Gly Glu Pro Tyr Phe Pro Tyr Trp Gly Gln Gly
                100                 105                 110

Thr Leu Val Thr Val Ser Ser Ala Ser Thr Lys Gly Pro Ser Val Phe
                115                 120                 125

Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
                195                 200                 205

Ser Asn Thr Lys Val Asp Lys Arg Val Glu Pro Lys Ser Cys Asp Lys
        210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
                275                 280                 285

Ala Lys Thr Lys Pro Arg Glu Glu Gln Tyr Asn Ser Thr Tyr Arg Val
        290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Glu Glu Met Thr Lys Asn Gln Val Ser Leu Thr
                355                 360                 365

Cys Leu Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
        435                 440                 445
```

-continued

Lys

<210> SEQ ID NO 127
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 127

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Ser Ser
            20                  25                  30

Trp Ile His Trp Val Lys Gln Ala Pro Gly Gln Gly Leu Glu Trp Met
        35                  40                  45

Gly Glu Ile Asn Pro Gly Asn Val Arg Thr Asn Tyr Asn Glu Asn Phe
    50                  55                  60

Arg Asn Lys Val Thr Met Thr Val Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Thr Val Val Phe Tyr Gly Glu Pro Tyr Phe Pro Tyr Trp Gly Gln Gly
                100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
        180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
        340                 345                 350

-continued

```
Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
        435                 440                 445

Lys
```

```
<210> SEQ ID NO 128
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 128
```

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Ser Ser
            20                  25                  30

Trp Ile His Trp Val Arg Gln Arg Pro Gly Gln Gly Leu Glu Trp Met
        35                  40                  45

Gly Glu Ile Asn Pro Gly Asn Val Arg Thr Asn Tyr Asn Glu Asn Phe
        50                  55                  60

Arg Asn Arg Ala Thr Leu Thr Arg Asp Thr Ser Ile Ser Thr Ala Tyr
65              70                  75                  80

Met Glu Leu Ser Arg Leu Arg Ser Asp Asp Thr Ala Val Tyr Tyr Cys
                85                  90                  95

Ala Val Val Phe Tyr Gly Glu Pro Tyr Phe Pro Tyr Trp Gly Gln Gly
                100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
        210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255
```

-continued

```
Arg Thr Pro Glu Val Thr Cys Val Val Val Asp Val Ser His Glu Asp
            260             265             270

Pro Glu Val Lys Phe Asn Trp Tyr Val Asp Gly Val Glu Val His Asn
            275             280             285

Ala Lys Thr Lys Pro Arg Glu Glu Gln Tyr Asn Ser Thr Tyr Arg Val
    290             295             300

Val Ser Val Leu Thr Val Leu His Gln Asp Trp Leu Asn Gly Lys Glu
305             310             315             320

Tyr Lys Cys Lys Val Ser Asn Lys Ala Leu Pro Ala Pro Ile Glu Lys
            325             330             335

Thr Ile Ser Lys Ala Lys Gly Gln Pro Arg Glu Pro Gln Val Tyr Thr
            340             345             350

Leu Pro Pro Ser Arg Glu Glu Met Thr Lys Asn Gln Val Ser Leu Thr
            355             360             365

Cys Leu Val Lys Gly Phe Tyr Pro Ser Asp Ile Ala Val Glu Trp Glu
    370             375             380

Ser Asn Gly Gln Pro Glu Asn Asn Tyr Lys Thr Thr Pro Pro Val Leu
385             390             395             400

Asp Ser Asp Gly Ser Phe Phe Leu Tyr Ser Lys Leu Thr Val Asp Lys
            405             410             415

Ser Arg Trp Gln Gln Gly Asn Val Phe Ser Cys Ser Val Met His Glu
            420             425             430

Ala Leu His Asn His Tyr Thr Gln Lys Ser Leu Ser Leu Ser Pro Gly
            435             440             445

Lys
```

```
<210> SEQ ID NO 129
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 129
```

```
Gln Val Gln Leu Val Gln Ser Gly Ala Glu Val Lys Lys Pro Gly Ala
1               5               10              15

Ser Val Lys Val Ser Cys Lys Ala Ser Gly Tyr Ser Phe Thr Ser Ser
            20              25              30

Trp Ile His Trp Val Arg Gln Arg Pro Gly Gln Gly Leu Glu Trp Met
            35              40              45

Gly Glu Ile Leu Pro Gly Val Val Arg Thr Asn Tyr Asn Glu Asn Phe
    50              55              60

Arg Asn Lys Val Thr Met Thr Val Asp Thr Ser Ile Ser Thr Ala Tyr
65              70              75              80

Met Glu Leu Ser Arg Leu Arg Ser Asp Asp Thr Ala Val Tyr Tyr Cys
            85              90              95

Thr Val Val Phe Tyr Gly Glu Pro Tyr Phe Pro Tyr Trp Gly Gln Gly
            100             105             110

Thr Leu Val Thr Val Ser Ser Ala Ser Thr Lys Gly Pro Ser Val Phe
            115             120             125

Pro Leu Ala Pro Ser Ser Lys Ser Thr Ser Gly Gly Thr Ala Ala Leu
    130             135             140

Gly Cys Leu Val Lys Asp Tyr Phe Pro Glu Pro Val Thr Val Ser Trp
145             150             155             160
```

-continued

```
Asn Ser Gly Ala Leu Thr Ser Gly Val His Thr Phe Pro Ala Val Leu
            165                     170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
            325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
            355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys
```

```
<210> SEQ ID NO 130
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 130
```

```
Gln Val Gln Leu Val Gln Ser Gly Ala Glu Val Lys Lys Pro Gly Ala
1                   5                   10                  15

Ser Val Lys Val Ser Cys Lys Ala Ser Gly Tyr Ser Phe Thr Ser Ser
            20                  25                  30

Trp Ile His Trp Val Arg Gln Arg Pro Gly Gln Gly Leu Glu Trp Ile
            35                  40                  45

Gly Glu Ile Asn Pro Gly Ala Val Arg Thr Asn Tyr Asn Glu Asn Phe
    50                  55                  60
```

-continued

```
Arg Asn Arg Val Thr Met Thr Val Asp Thr Ser Ile Ser Thr Ala Tyr
65              70              75              80

Met Glu Leu Ser Arg Leu Arg Ser Asp Asp Thr Ala Val Tyr Tyr Cys
                85              90              95

Thr Val Val Phe Tyr Gly Glu Pro Tyr Phe Pro Tyr Trp Gly Gln Gly
            100             105             110

Thr Leu Val Thr Val Ser Ser Ala Ser Thr Lys Gly Pro Ser Val Phe
            115             120             125

Pro Leu Ala Pro Ser Ser Lys Ser Thr Ser Gly Gly Thr Ala Ala Leu
    130             135             140

Gly Cys Leu Val Lys Asp Tyr Phe Pro Glu Pro Val Thr Val Ser Trp
145             150             155             160

Asn Ser Gly Ala Leu Thr Ser Gly Val His Thr Phe Pro Ala Val Leu
                165             170             175

Gln Ser Ser Gly Leu Tyr Ser Leu Ser Ser Val Val Thr Val Pro Ser
            180             185             190

Ser Ser Leu Gly Thr Gln Thr Tyr Ile Cys Asn Val Asn His Lys Pro
            195             200             205

Ser Asn Thr Lys Val Asp Lys Arg Val Glu Pro Lys Ser Cys Asp Lys
    210             215             220

Thr His Thr Cys Pro Pro Cys Pro Ala Pro Glu Ala Ala Gly Gly Pro
225             230             235             240

Ser Val Phe Leu Phe Pro Pro Lys Pro Lys Asp Thr Leu Met Ile Ser
                245             250             255

Arg Thr Pro Glu Val Thr Cys Val Val Val Asp Val Ser His Glu Asp
            260             265             270

Pro Glu Val Lys Phe Asn Trp Tyr Val Asp Gly Val Glu Val His Asn
            275             280             285

Ala Lys Thr Lys Pro Arg Glu Glu Gln Tyr Asn Ser Thr Tyr Arg Val
    290             295             300

Val Ser Val Leu Thr Val Leu His Gln Asp Trp Leu Asn Gly Lys Glu
305             310             315             320

Tyr Lys Cys Lys Val Ser Asn Lys Ala Leu Pro Ala Pro Ile Glu Lys
                325             330             335

Thr Ile Ser Lys Ala Lys Gly Gln Pro Arg Glu Pro Gln Val Tyr Thr
            340             345             350

Leu Pro Pro Ser Arg Glu Glu Met Thr Lys Asn Gln Val Ser Leu Thr
            355             360             365

Cys Leu Val Lys Gly Phe Tyr Pro Ser Asp Ile Ala Val Glu Trp Glu
    370             375             380

Ser Asn Gly Gln Pro Glu Asn Asn Tyr Lys Thr Thr Pro Pro Val Leu
385             390             395             400

Asp Ser Asp Gly Ser Phe Phe Leu Tyr Ser Lys Leu Thr Val Asp Lys
                405             410             415

Ser Arg Trp Gln Gln Gly Asn Val Phe Ser Cys Ser Val Met His Glu
            420             425             430

Ala Leu His Asn His Tyr Thr Gln Lys Ser Leu Ser Leu Ser Pro Gly
            435             440             445

Lys
```

<210> SEQ ID NO 131
<211> LENGTH: 449
<212> TYPE: PRT
<213> ORGANISM: Artificial Sequence -continued
<220> FEATURE:
<223> OTHER INFORMATION: Description of Artificial Sequence: Synthetic
      polypeptide

<400> SEQUENCE: 131

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Ser Ser
                20                  25                  30

Trp Ile His Trp Val Arg Gln Ala Pro Gly Gln Gly Leu Glu Trp Ile
            35                  40                  45

Gly Glu Ile Asn Pro Gly Leu Val Arg Thr Asn Tyr Asn Glu Asn Phe
        50                  55                  60

Arg Asn Lys Val Thr Met Thr Val Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Val Val Phe Tyr Gly Glu Pro Tyr Phe Pro Tyr Trp Gly Gln Gly
            100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Arg Val Glu Pro Lys Ser Cys Asp Lys
        210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
        290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Glu Glu Met Thr Lys Asn Gln Val Ser Leu Thr
            355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
```

-continued

```
385              390              395              400

Asp Ser Asp Gly Ser Phe Phe Leu Tyr Ser Lys Leu Thr Val Asp Lys
            405              410              415

Ser Arg Trp Gln Gln Gly Asn Val Phe Ser Cys Ser Val Met His Glu
            420              425              430

Ala Leu His Asn His Tyr Thr Gln Lys Ser Leu Ser Leu Ser Pro Gly
        435              440              445

Lys

<210> SEQ ID NO 132
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 132

Gln Val Gln Leu Val Gln Ser Gly Ala Glu Val Lys Lys Pro Gly Ala
1               5               10              15

Ser Val Lys Val Ser Cys Lys Ala Ser Gly Tyr Ser Phe Thr Ser Ser
            20              25              30

Trp Ile His Trp Val Arg Gln Ala Pro Gly Gln Gly Leu Glu Trp Ile
        35              40              45

Gly Glu Ile Asn Pro Gly Ala Val Arg Thr Asn Tyr Asn Glu Asn Phe
    50              55              60

Arg Asn Lys Val Thr Met Thr Val Asp Thr Ser Ile Ser Thr Ala Tyr
65              70              75              80

Met Glu Leu Ser Arg Leu Arg Ser Asp Asp Thr Ala Val Tyr Tyr Cys
            85              90              95

Ala Val Val Phe Tyr Gly Glu Pro Tyr Phe Pro Tyr Trp Gly Gln Gly
            100             105             110

Thr Leu Val Thr Val Ser Ser Ala Ser Thr Lys Gly Pro Ser Val Phe
        115             120             125

Pro Leu Ala Pro Ser Ser Lys Ser Thr Ser Gly Gly Thr Ala Ala Leu
    130             135             140

Gly Cys Leu Val Lys Asp Tyr Phe Pro Glu Pro Val Thr Val Ser Trp
145             150             155             160

Asn Ser Gly Ala Leu Thr Ser Gly Val His Thr Phe Pro Ala Val Leu
            165             170             175

Gln Ser Ser Gly Leu Tyr Ser Leu Ser Ser Val Val Thr Val Pro Ser
        180             185             190

Ser Ser Leu Gly Thr Gln Thr Tyr Ile Cys Asn Val Asn His Lys Pro
        195             200             205

Ser Asn Thr Lys Val Asp Lys Arg Val Glu Pro Lys Ser Cys Asp Lys
    210             215             220

Thr His Thr Cys Pro Pro Cys Pro Ala Pro Glu Ala Ala Gly Gly Pro
225             230             235             240

Ser Val Phe Leu Phe Pro Pro Lys Pro Lys Asp Thr Leu Met Ile Ser
            245             250             255

Arg Thr Pro Glu Val Thr Cys Val Val Val Asp Val Ser His Glu Asp
            260             265             270

Pro Glu Val Lys Phe Asn Trp Tyr Val Asp Gly Val Glu Val His Asn
        275             280             285

Ala Lys Thr Lys Pro Arg Glu Glu Gln Tyr Asn Ser Thr Tyr Arg Val
```

-continued

```
          290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Glu Glu Met Thr Lys Asn Gln Val Ser Leu Thr
                355                 360                 365

Cys Leu Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
        435                 440                 445

Lys
```

```
<210> SEQ ID NO 133
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 133

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Ser Ser
                20                  25                  30

Trp Ile His Trp Val Arg Gln Ala Pro Gly Gln Gly Leu Glu Trp Ile
            35                  40                  45

Gly Glu Ile Asn Pro Gly Ser Val Arg Thr Asn Tyr Asn Glu Asn Phe
        50                  55                  60

Arg Asn Lys Ala Thr Met Thr Val Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Val Val Phe Tyr Gly Glu Pro Tyr Phe Pro Tyr Trp Gly Gln Gly
                100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
```

-continued

```
            195                 200                 205
Ser Asn Thr Lys Val Asp Lys Arg Val Glu Pro Lys Ser Cys Asp Lys
    210                 215                 220
Thr His Thr Cys Pro Pro Cys Pro Ala Pro Glu Ala Ala Gly Gly Pro
225                 230                 235                 240
Ser Val Phe Leu Phe Pro Pro Lys Pro Lys Asp Thr Leu Met Ile Ser
                    245                 250                 255
Arg Thr Pro Glu Val Thr Cys Val Val Val Asp Val Ser His Glu Asp
                260                 265                 270
Pro Glu Val Lys Phe Asn Trp Tyr Val Asp Gly Val Glu Val His Asn
            275                 280                 285
Ala Lys Thr Lys Pro Arg Glu Glu Gln Tyr Asn Ser Thr Tyr Arg Val
        290                 295                 300
Val Ser Val Leu Thr Val Leu His Gln Asp Trp Leu Asn Gly Lys Glu
305                 310                 315                 320
Tyr Lys Cys Lys Val Ser Asn Lys Ala Leu Pro Ala Pro Ile Glu Lys
                    325                 330                 335
Thr Ile Ser Lys Ala Lys Gly Gln Pro Arg Glu Pro Gln Val Tyr Thr
                340                 345                 350
Leu Pro Pro Ser Arg Glu Glu Met Thr Lys Asn Gln Val Ser Leu Thr
            355                 360                 365
Cys Leu Val Lys Gly Phe Tyr Pro Ser Asp Ile Ala Val Glu Trp Glu
        370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Tyr Ser Lys Leu Thr Val Asp Lys
                    405                 410                 415
Ser Arg Trp Gln Gln Gly Asn Val Phe Ser Cys Ser Val Met His Glu
                420                 425                 430
Ala Leu His Asn His Tyr Thr Gln Lys Ser Leu Ser Leu Ser Pro Gly
            435                 440                 445
Lys
```

```
<210> SEQ ID NO 134
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 134
```

```
Gln Val Gln Leu Gln Glu Ser Gly Pro Gly Leu Val Lys Pro Ser Glu
1               5                   10                  15
Thr Leu Ser Ile Thr Cys Thr Val Ser Gly Phe Ser Leu Thr Asp Tyr
                20                  25                  30
Ala Val His Trp Ile Arg Gln Pro Pro Gly Lys Gly Leu Glu Trp Ile
            35                  40                  45
Gly Val Ile Trp Ser Asp Gly Ser Thr Asp Tyr Asn Ala Pro Phe Lys
        50                  55                  60
Ser Arg Val Thr Ile Asn Lys Asp Thr Ser Lys Ser Gln Val Ser Phe
65                  70                  75                  80
Lys Met Ser Ser Val Gln Ala Ala Asp Thr Ala Val Tyr Tyr Cys Ala
                85                  90                  95
Arg Lys Gly Gly Tyr Ser Gly Ser Trp Phe Ala Tyr Trp Gly Gln Gly
```

-continued

```
              100                 105                 110
Thr Leu Val Thr Val Ser Ser Ala Ser Thr Lys Gly Pro Ser Val Phe
        115                 120                 125
Pro Leu Ala Pro Ser Ser Lys Ser Thr Ser Gly Gly Thr Ala Ala Leu
        130                 135                 140
Gly Cys Leu Val Lys Asp Tyr Phe Pro Glu Pro Val Thr Val Ser Trp
145                 150                 155                 160
Asn Ser Gly Ala Leu Thr Ser Gly Val His Thr Phe Pro Ala Val Leu
                165                 170                 175
Gln Ser Ser Gly Leu Tyr Ser Leu Ser Ser Val Val Thr Val Pro Ser
                180                 185                 190
Ser Ser Leu Gly Thr Gln Thr Tyr Ile Cys Asn Val Asn His Lys Pro
        195                 200                 205
Ser Asn Thr Lys Val Asp Lys Arg Val Glu Pro Lys Ser Cys Asp Lys
        210                 215                 220
Thr His Thr Cys Pro Pro Cys Pro Ala Pro Glu Ala Ala Gly Gly Pro
225                 230                 235                 240
Ser Val Phe Leu Phe Pro Pro Lys Pro Lys Asp Thr Leu Met Ile Ser
                245                 250                 255
Arg Thr Pro Glu Val Thr Cys Val Val Val Asp Val Ser His Glu Asp
                260                 265                 270
Pro Glu Val Lys Phe Asn Trp Tyr Val Asp Gly Val Glu Val His Asn
        275                 280                 285
Ala Lys Thr Lys Pro Arg Glu Glu Gln Tyr Asn Ser Thr Tyr Arg Val
        290                 295                 300
Val Ser Val Leu Thr Val Leu His Gln Asp Trp Leu Asn Gly Lys Glu
305                 310                 315                 320
Tyr Lys Cys Lys Val Ser Asn Lys Ala Leu Pro Ala Pro Ile Glu Lys
                325                 330                 335
Thr Ile Ser Lys Ala Lys Gly Gln Pro Arg Glu Pro Gln Val Tyr Thr
                340                 345                 350
Leu Pro Pro Ser Arg Glu Glu Met Thr Lys Asn Gln Val Ser Leu Thr
                355                 360                 365
Cys Leu Val Lys Gly Phe Tyr Pro Ser Asp Ile Ala Val Glu Trp Glu
        370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Tyr Ser Lys Leu Thr Val Asp Lys
                405                 410                 415
Ser Arg Trp Gln Gln Gly Asn Val Phe Ser Cys Ser Val Met His Glu
                420                 425                 430
Ala Leu His Asn His Tyr Thr Gln Lys Ser Leu Ser Leu Ser Pro Gly
        435                 440                 445
Lys
```

<210> SEQ ID NO 135
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 135

Gln Val Gln Leu Gln Glu Ser Gly Pro Gly Leu Val Lys Pro Ser Glu

-continued

```
1               5               10              15

Thr Leu Ser Ile Thr Cys Thr Val Ser Gly Phe Ser Leu Thr Asp Tyr
                20              25              30

Ala Val His Trp Ile Arg Gln Pro Pro Gly Lys Gly Leu Glu Trp Ile
        35              40              45

Gly Val Ile Trp Ser Asp Gly Ser Thr Asp Tyr Asn Ala Pro Phe Lys
    50              55              60

Ser Arg Val Thr Ile Ser Lys Asp Thr Ser Lys Asn Gln Val Ser Leu
65              70              75              80

Lys Met Asn Ser Leu Thr Thr Asp Asp Thr Ala Val Tyr Tyr Cys Ala
            85              90              95

Arg Lys Gly Gly Tyr Ser Gly Ser Trp Phe Ala Tyr Trp Gly Gln Gly
            100             105             110

Thr Leu Val Thr Val Ser Ser Ala Ser Thr Lys Gly Pro Ser Val Phe
        115             120             125

Pro Leu Ala Pro Ser Ser Lys Ser Thr Ser Gly Gly Thr Ala Ala Leu
    130             135             140

Gly Cys Leu Val Lys Asp Tyr Phe Pro Glu Pro Val Thr Val Ser Trp
145             150             155             160

Asn Ser Gly Ala Leu Thr Ser Gly Val His Thr Phe Pro Ala Val Leu
            165             170             175

Gln Ser Ser Gly Leu Tyr Ser Leu Ser Ser Val Val Thr Val Pro Ser
            180             185             190

Ser Ser Leu Gly Thr Gln Thr Tyr Ile Cys Asn Val Asn His Lys Pro
            195             200             205

Ser Asn Thr Lys Val Asp Lys Arg Val Glu Pro Lys Ser Cys Asp Lys
    210             215             220

Thr His Thr Cys Pro Pro Cys Pro Ala Pro Glu Ala Ala Gly Gly Pro
225             230             235             240

Ser Val Phe Leu Phe Pro Pro Lys Pro Lys Asp Thr Leu Met Ile Ser
            245             250             255

Arg Thr Pro Glu Val Thr Cys Val Val Val Asp Val Ser His Glu Asp
            260             265             270

Pro Glu Val Lys Phe Asn Trp Tyr Val Asp Gly Val Glu Val His Asn
            275             280             285

Ala Lys Thr Lys Pro Arg Glu Glu Gln Tyr Asn Ser Thr Tyr Arg Val
    290             295             300

Val Ser Val Leu Thr Val Leu His Gln Asp Trp Leu Asn Gly Lys Glu
305             310             315             320

Tyr Lys Cys Lys Val Ser Asn Lys Ala Leu Pro Ala Pro Ile Glu Lys
            325             330             335

Thr Ile Ser Lys Ala Lys Gly Gln Pro Arg Glu Pro Gln Val Tyr Thr
            340             345             350

Leu Pro Pro Ser Arg Glu Glu Met Thr Lys Asn Gln Val Ser Leu Thr
            355             360             365

Cys Leu Val Lys Gly Phe Tyr Pro Ser Asp Ile Ala Val Glu Trp Glu
    370             375             380

Ser Asn Gly Gln Pro Glu Asn Asn Tyr Lys Thr Thr Pro Pro Val Leu
385             390             395             400

Asp Ser Asp Gly Ser Phe Phe Leu Tyr Ser Lys Leu Thr Val Asp Lys
            405             410             415

Ser Arg Trp Gln Gln Gly Asn Val Phe Ser Cys Ser Val Met His Glu
            420             425             430
```

```
Ala Leu His Asn His Tyr Thr Gln Lys Ser Leu Ser Leu Ser Pro Gly
        435                 440                 445

Lys

<210> SEQ ID NO 136
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 136

Gln Val Gln Leu Gln Glu Ser Gly Pro Gly Leu Val Lys Pro Ser Glu
1               5                   10                  15

Thr Leu Ser Ile Thr Cys Thr Val Ser Gly Phe Ser Leu Thr Asp Tyr
            20                  25                  30

Ala Val His Trp Ile Arg Gln Pro Pro Gly Lys Gly Leu Glu Trp Ile
        35                  40                  45

Gly Val Ile Trp Ser Asp Gly Ser Thr Asp Tyr Asn Ala Pro Phe Lys
    50                  55                  60

Ser Arg Val Thr Ile Ser Lys Asp Asn Ser Lys Ser Gln Val Ser Leu
65                  70                  75                  80

Lys Met Asn Ser Val Thr Val Ala Asp Thr Ala Val Tyr Tyr Cys Ala
                85                  90                  95

Arg Lys Gly Gly Tyr Ser Gly Ser Trp Phe Ala Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335
```

```
Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
            355                 360                 365

Cys Leu Val Lys Gly Phe Tyr Pro Ser Asp Ile Ala Val Glu Trp Glu
            370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys

<210> SEQ ID NO 137
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 137

Gln Val Gln Leu Gln Glu Ser Gly Pro Gly Leu Val Lys Pro Ser Glu
1               5                   10                  15

Thr Leu Ser Ile Thr Cys Thr Val Ser Gly Phe Ser Leu Thr Asp Tyr
                20                  25                  30

Ala Val His Trp Val Arg Gln Pro Pro Gly Lys Gly Leu Glu Trp Ile
            35                  40                  45

Gly Val Ile Trp Ser Asp Gly Ser Thr Asp Tyr Asn Ala Pro Phe Lys
        50                  55                  60

Ser Arg Val Thr Ile Ser Lys Asp Thr Ser Lys Asn Gln Val Ser Phe
65                  70                  75                  80

Lys Leu Ser Ser Val Thr Val Asp Asp Thr Ala Val Tyr Tyr Cys Ala
                85                  90                  95

Arg Lys Gly Gly Tyr Ser Gly Ser Trp Phe Ala Tyr Trp Gly Gln Gly
            100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Arg Val Glu Pro Lys Ser Cys Asp Lys
        210                 215                 220

Thr His Thr Cys Pro Pro Cys Pro Ala Pro Glu Ala Ala Gly Gly Pro
225                 230                 235                 240
```

```
Ser Val Phe Leu Phe Pro Pro Lys Pro Lys Asp Thr Leu Met Ile Ser
            245             250                 255

Arg Thr Pro Glu Val Thr Cys Val Val Val Asp Val Ser His Glu Asp
            260             265                 270

Pro Glu Val Lys Phe Asn Trp Tyr Val Asp Gly Val Glu Val His Asn
            275             280                 285

Ala Lys Thr Lys Pro Arg Glu Glu Gln Tyr Asn Ser Thr Tyr Arg Val
    290             295                 300

Val Ser Val Leu Thr Val Leu His Gln Asp Trp Leu Asn Gly Lys Glu
305             310                 315                 320

Tyr Lys Cys Lys Val Ser Asn Lys Ala Leu Pro Ala Pro Ile Glu Lys
            325             330                 335

Thr Ile Ser Lys Ala Lys Gly Gln Pro Arg Glu Pro Gln Val Tyr Thr
            340             345                 350

Leu Pro Pro Ser Arg Glu Glu Met Thr Lys Asn Gln Val Ser Leu Thr
            355             360                 365

Cys Leu Val Lys Gly Phe Tyr Pro Ser Asp Ile Ala Val Glu Trp Glu
    370             375                 380

Ser Asn Gly Gln Pro Glu Asn Asn Tyr Lys Thr Thr Pro Pro Val Leu
385             390                 395                 400

Asp Ser Asp Gly Ser Phe Phe Leu Tyr Ser Lys Leu Thr Val Asp Lys
            405             410                 415

Ser Arg Trp Gln Gln Gly Asn Val Phe Ser Cys Ser Val Met His Glu
            420             425                 430

Ala Leu His Asn His Tyr Thr Gln Lys Ser Leu Ser Leu Ser Pro Gly
            435             440                 445

Lys
```

```
<210> SEQ ID NO 138
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 138

Gln Val Gln Leu Gln Glu Ser Gly Pro Gly Leu Val Ala Pro Ser Glu
1               5                   10                  15

Thr Leu Ser Leu Thr Cys Thr Val Ser Gly Phe Ser Leu Thr Asp Tyr
            20                  25                  30

Ala Val His Trp Ile Arg Gln Phe Pro Gly Lys Gly Leu Glu Trp Ile
        35                  40                  45

Gly Val Ile Trp Ser Asp Gly Ser Thr Asp Phe Asn Ala Pro Phe Lys
    50                  55                  60

Ser Arg Val Thr Ile Ser Lys Asp Thr Ser Lys Asn Gln Val Ser Phe
65                  70                  75                  80

Lys Leu Ser Ser Val Thr Thr Asp Asp Thr Ala Val Tyr Tyr Cys Ala
            85                  90                  95

Arg Lys Gly Gly Tyr Ser Gly Ser Trp Phe Ala Tyr Trp Gly Gln Gly
            100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
    130                 135                 140
```

```
Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
            355                 360                 365

Cys Leu Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys
```

<210> SEQ ID NO 139
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 139

```
Gln Val Gln Leu Gln Glu Ser Gly Pro Gly Leu Val Lys Pro Ser Glu
1                 5                   10                  15

Thr Leu Ser Ile Thr Cys Thr Val Ser Gly Phe Ser Leu Thr Asp Tyr
                20                  25                  30

Ala Val His Trp Ile Arg Gln Pro Pro Gly Lys Gly Leu Glu Trp Ile
            35                  40                  45
```

```
Gly Val Ile Trp Ser Asp Gly Ser Thr Asp Tyr Asn Ala Pro Phe Lys
    50              55              60

Ser Arg Val Thr Ile Ser Lys Asp Asn Ser Lys Ser Gln Val Ser Phe
65              70              75              80

Lys Met Ser Ser Val Thr Ala Asp Asp Thr Ala Val Tyr Tyr Cys Ala
            85              90              95

Arg Lys Gly Gly Tyr Ser Gly Ser Trp Phe Ala Tyr Trp Gly Gln Gly
            100             105             110

Thr Leu Val Thr Val Ser Ser Ala Ser Thr Lys Gly Pro Ser Val Phe
        115             120             125

Pro Leu Ala Pro Ser Ser Lys Ser Thr Ser Gly Gly Thr Ala Ala Leu
    130             135             140

Gly Cys Leu Val Lys Asp Tyr Phe Pro Glu Pro Val Thr Val Ser Trp
145             150             155             160

Asn Ser Gly Ala Leu Thr Ser Gly Val His Thr Phe Pro Ala Val Leu
            165             170             175

Gln Ser Ser Gly Leu Tyr Ser Leu Ser Ser Val Val Thr Val Pro Ser
        180             185             190

Ser Ser Leu Gly Thr Gln Thr Tyr Ile Cys Asn Val Asn His Lys Pro
        195             200             205

Ser Asn Thr Lys Val Asp Lys Arg Val Glu Pro Lys Ser Cys Asp Lys
    210             215             220

Thr His Thr Cys Pro Pro Cys Pro Ala Pro Glu Ala Ala Gly Gly Pro
225             230             235             240

Ser Val Phe Leu Phe Pro Pro Lys Pro Lys Asp Thr Leu Met Ile Ser
            245             250             255

Arg Thr Pro Glu Val Thr Cys Val Val Val Asp Val Ser His Glu Asp
            260             265             270

Pro Glu Val Lys Phe Asn Trp Tyr Val Asp Gly Val Glu Val His Asn
        275             280             285

Ala Lys Thr Lys Pro Arg Glu Glu Gln Tyr Asn Ser Thr Tyr Arg Val
    290             295             300

Val Ser Val Leu Thr Val Leu His Gln Asp Trp Leu Asn Gly Lys Glu
305             310             315             320

Tyr Lys Cys Lys Val Ser Asn Lys Ala Leu Pro Ala Pro Ile Glu Lys
            325             330             335

Thr Ile Ser Lys Ala Lys Gly Gln Pro Arg Glu Pro Gln Val Tyr Thr
            340             345             350

Leu Pro Pro Ser Arg Glu Glu Met Thr Lys Asn Gln Val Ser Leu Thr
        355             360             365

Cys Leu Val Lys Gly Phe Tyr Pro Ser Asp Ile Ala Val Glu Trp Glu
    370             375             380

Ser Asn Gly Gln Pro Glu Asn Asn Tyr Lys Thr Thr Pro Pro Val Leu
385             390             395             400

Asp Ser Asp Gly Ser Phe Phe Leu Tyr Ser Lys Leu Thr Val Asp Lys
            405             410             415

Ser Arg Trp Gln Gln Gly Asn Val Phe Ser Cys Ser Val Met His Glu
            420             425             430

Ala Leu His Asn His Tyr Thr Gln Lys Ser Leu Ser Leu Ser Pro Gly
        435             440             445

Lys
```

-continued

```
<210> SEQ ID NO 140
<211> LENGTH: 7
<212> TYPE: PRT
<213> ORGANISM: Mus sp.

<400> SEQUENCE: 140

Arg Thr Ser His Leu Ala Ser
1               5
```